United States Patent
Hornbeck et al.

(10) Patent No.: US 8,618,260 B2
(45) Date of Patent: Dec. 31, 2013

(54) TYROSINE, SERINE AND THREONINE PHOSPHORYLATION SITES

(75) Inventors: Peter Hornbeck, Magnolia, MA (US);
Albrecht Moritz, Salem, MA (US);
John Rush, Beverly, MA (US); Steven Gygi, Boston, MA (US)

(73) Assignee: Cell Signaling Technology, Inc., Danvers, MA (US)

( * ) Notice: Subject to any disclaimer, the term of this patent is extended or adjusted under 35 U.S.C. 154(b) by 898 days.

(21) Appl. No.: 12/310,852

(22) PCT Filed: Sep. 8, 2007

(86) PCT No.: PCT/US2007/019488
§ 371 (c)(1),
(2), (4) Date: Feb. 2, 2010

(87) PCT Pub. No.: WO2008/030543
PCT Pub. Date: Mar. 13, 2008

(65) Prior Publication Data
US 2013/0004963 A1      Jan. 3, 2013

Related U.S. Application Data

(60) Provisional application No. 60/843,348, filed on Sep. 8, 2006.

(51) Int. Cl.
*C07K 16/00* (2006.01)

(52) U.S. Cl.
USPC ............................................... 530/387.1

(58) Field of Classification Search
None
See application file for complete search history.

(56) References Cited

PUBLICATIONS

Haldrup et al (JBC, 2000, 275(40): 31211-31218).*

* cited by examiner

*Primary Examiner* — Sean Aeder
(74) *Attorney, Agent, or Firm* — Ryan S. McQuade; J Matthew Jones

(57) ABSTRACT

The invention discloses 155 novel phosphorylation sites identified in carcinoma and leukemia, peptides (including AQUA peptides) comprising a phosphorylation site of the invention, antibodies specifically bind to a novel phosphorylation site of the invention, and diagnostic and therapeutic uses of the above.

9 Claims, 20 Drawing Sheets
(6 of 20 Drawing Sheet(s) Filed in Color)

FIG. 2A

| | Protein Name | Accession No. | Protein Type | Phospho-Residue | Phosphorylation Site Sequence | Disease | Cell Line / Tissue / Patient | SEQ ID NO |
|---|---|---|---|---|---|---|---|---|
| 1 | | | | | | | | |
| 2 | AHNAK | NP_001611.1 | Adaptor/scaffold | T5798 | EFSGPSTPTGtLEFEGGEVSLEGGK | cancer, cervical, adenocarcinoma | HeLa | SEQ ID NO: 1 |
| 3 | PDE4DIP | NP_001002811.1 | Adaptor/scaffold | Y180 | VADSDyEAICKVPR | cancer, leukemia | Jurkat | SEQ ID NO: 2 |
| 4 | RANBP9 | NP_005484.2 | Adaptor/scaffold | S477 | SQDSYPVsPRPFSSPSMSPSHGMNIHNLASGK | cancer, cervical, adenocarcinoma; cancer, leukemia; chronic myelogenous (CML); cancer, lung, small-cell | HeLa; Jurkat; K562 | SEQ ID NO: 3 |
| 5 | RANBP9 | NP_005484.2 | Adaptor/scaffold | S487 | SQDSYPVSPRPFSSPSMsPSHGMNIHNLASGK | cancer, lung, small-cell; cancer, cervical, adenocarcinoma | HeLa | SEQ ID NO: 4 |
| 6 | RIMS1 | NP_055804.2 | Adaptor/scaffold | T:245 | TLCSMHHLVPGGSAPPSPLLtR | adenocarcinoma | HeLa | SEQ ID NO: 5 |
| 7 | SLA | NP_006739.1 | Adaptor/scaffold | Y273 | KSSFFSSPPyFED | cancer, leukemia | Jurkat | SEQ ID NO: 6 |
| 8 | TANC1 | NP_203752.1 | Adaptor/scaffold | Y1827 | TVSHLyQESISK | cancer, leukemia | Jurkat | SEQ ID NO: 7 |
| 9 | TFG | NP_006061.2 | Adaptor/scaffold | Y392 | NRPPFCQQyTQPGPGYR | | Jurkat | SEQ ID NO: 8 |
| 10 | BYSL | NP_004044.3 | Adhesion or extracellular matrix protein | Y49 | GRGTGEAEEyVGPR | cancer, leukemia | Jurkat | SEQ ID NO: 9 |
| 11 | FLRT2 | NP_037363.1 | Adhesion or extracellular matrix protein | S403 | SYTPPTPTTsKLPTIPDWDGR | cancer, cervical, adenocarcinoma | HeLa | SEQ ID NO: 10 |
| 12 | MLLT4 | NP_055927.2 | Adhesion or extracellular | Y1269 | SQEELREDKAyQLER | cancer, leukemia | Jurkat | SEQ ID NO: 11 |
| 13 | SSX2IP | NP_054740.2 | Adhesion or extracellular | S540 | SLPAsPSTSDFCQTR | cancer, leukemia | DMS 153 | SEQ ID NO: 12 |
| 14 | CIAPIN1 | NP_064709.2 | Apoptosis | Y290 | CASCPyLGMPAFKPGEK | cancer, leukemia | Jurkat | SEQ ID NO: 13 |
| 15 | CNNM3 | NP_060093.3 | Cell cycle regulation | Y301 | GGGDPySDLSK | cancer, leukemia | Jurkat | SEQ ID NO: 14 |
| 16 | MDC1 | CAI18195.1 | Cell cycle regulation | T:1548 | TPETVVPRAPELQPSTSTDQPVtPEPTSR | cancer, leukemia, chronic myelogenous (CML); cancer, cervical, adenocarcinoma | HeLa; K562 | SEQ ID NO: 15 |
| 17 | ORC3L | NP_036513.2 | Cell cycle regulation | Y527 | TDLyHLQK | cancer, leukemia | Jurkat | SEQ ID NO: 16 |
| 18 | APRIN | NP_055847.1 | Chromatin, DNA-binding, DNA repair or DNA | S1162 | METVSNAsSSsNPSSPGR | cancer, cervical, adenocarcinoma | HeLa | SEQ ID NO: 17 |
| 19 | APRIN | NP_055847.1 | Chromatin, DNA-binding, DNA repair or DNA | S1159 | METVSNAsSSSNPSSPGR | cancer, cervical, adenocarcinoma | HeLa | SEQ ID NO: 18 |
| 20 | APRIN | NP_055847.1 | Chromatin, DNA-binding, DNA repair or DNA | S1150 | METVSNAsSSNPSSPGR | cancer, cervical, adenocarcinoma | HeLa | SEQ ID NO: 19 |

FIG. 2B

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 21 | HIVEP1 | NP_002105.1 | Chromatin, DNA-binding, DNA repair or DNA | S537 | SSFTPSsPEMVIGDFLLQDR | cancer, colorectal carcinoma | HeLa | SEQ ID NO: 20 |
| 22 | TMPO | NP_001027454.1 | Chromatin, DNA-binding, DNA repair or DNA | Y223 | RVEHNQSySQAGITETEWTSGSSK | cancer, leukemia, chronic myelogenous (CML) | K562 | SEQ ID NO: 21 |
| 23 | TOX | NP_055544.1 | Chromatin, DNA-binding, DNA repair or DNA | Y511 | SGCRNPPPQPVDWNNDyCSSGGMQR | cancer, lung, non-small cell | Jurkat | SEQ ID NO: 22 |
| 24 | ZC3HAV1 | NP_064504.2 | Chromatin, DNA-binding, DNA repair or DNA | Y690 | RPTFVPQWyVQQMK | cancer, leukemia | Jurkat | SEQ ID NO: 23 |
| 25 | ABLIM1 | NP_006711.3 | Cytoskeletal protein | Y199 | SPQHFHRPDQGINIyR | cancer, leukemia | Jurkat | SEQ ID NO: 24 |
| 26 | MAP1A | NP_002364.5 | Cytoskeletal protein | T1834 | NEPtTPSWLADIPPWVPK | cancer, cervical, adenocarcinoma | HeLa | SEQ ID NO: 25 |
| 27 | NDE1 | NP_060138.1 | Cytoskeletal protein | T246 | GLDDStGGTPLtPAAR | cancer, cervical, adenocarcinoma cancer, colorectal carcinoma cancer, leukemia, chronic myelogenous (CML) | HeLa K562 | SEQ ID NO: 26 |
| 28 | KIF1C | NP_006603.2 | Endoplasmic reticulum or golgi | S1026 | RPPSPRRsHHPR | cancer, cervical, adenocarcinoma | HeLa | SEQ ID NO: 27 |
| 29 | KIF1C | NP_006603.2 | Endoplasmic reticulum or golgi | S1022 | RPPsPRRSHHPR | cancer, cervical, adenocarcinoma | HeLa | SEQ ID NO: 28 |
| 30 | B4GALNT4 | NP_846632.2 | Enzyme, misc. | S491 | SGPQSPAPAAPAQPGATLAPPTPPRPRDGGTPRHsR | cancer, cervical, adenocarcinoma | HeLa | SEQ ID NO: 29 |
| 31 | B4GALNT4 | NP_846632.2 | Enzyme, misc. | T478 | SGPQSPAPAAPAQPGATLAPPtPPRPRDGGTPRHSR | cancer, cervical, adenocarcinoma | HeLa | SEQ ID NO: 30 |
| 32 | B4GALNT4 | NP_846632.2 | Enzyme, misc. | S461 | SGPQsPAPAAPAQPGATLAPPTPPRPRDGGTPRHSR | cancer, cervical, adenocarcinoma | HeLa | SEQ ID NO: 31 |
| 33 | DAGLBETA | NP_631918.1 | Enzyme, misc. | Y573 | WSPAySFSSDSPLDSSPK | cancer, leukemia | Jurkat | SEQ ID NO: 32 |

FIG. 2C

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 34 | DOT1L | NP_115871.1 | Enzyme, misc. | S1009 | NSLPASPAHQLSSsPR | cancer, colorectal carcinoma; cancer, leukemia, chronic lymphocytic (CLL); cancer, leukemia, chronic myelogenous (CML); cancer, lung, non-small cell | HeLa; H526; H69 (xenograft); K562 | SEQ ID NO: 33 |
| 35 | EZH2 | NP_004447.2 | Enzyme, misc. | T372 | LPNNSSRPStPTINVLESK | cancer, cervical, adenocarcinoma; cancer, colorectal carcinoma; cancer, leukemia, chronic myelogenous (CML) | HeLa; K562 | SEQ ID NO: 34 |
| 36 | EZH2 | NP_004447.2 | Enzyme, misc. | S368 | LPNNSsRPSTPTINVLESK | cancer, cervical, adenocarcinoma | HeLa; HT29 | SEQ ID NO: 35 |
| 37 | IARS | NP_002152.2 | Enzyme, misc. | S1047 | APLKPYPVsPSDKVLIQEK | cancer, cervical, adenocarcinoma; cancer, leukemia; cancer, lung, small-cell | HeLa; Jurkat | SEQ ID NO: 36 |
| 38 | JMJD1B | NP_057688.2 | Enzyme, misc. | T1307 | DLLHSGPGKLPQPLDTGIPFPPVFSTSSAGVK | cancer, leukemia, chronic myelogenous (CML); cancer, cervical, adenocarcinoma | HeLa; K562 | SEQ ID NO: 37 |
| 39 | PPIL4 | NP_624311.1 | Enzyme, misc. | Y466 | YQtDLyERER | cancer, colorectal carcinoma; cancer, leukemia, chronic myelogenous (CML); cancer, lung, non-small cell | HeLa; HT29 | SEQ ID NO: 38 |
| 40 | ARHGEF11 | NP_055599.1 | G protein or regulator | T668 | SLENPtPPFTPK | cancer, cervical, adenocarcinoma | HeLa; K562 | SEQ ID NO: 39 |

FIG. 2D

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 41 | ARHGEF11 | NP_055599.1 | G protein or regulator | T672 | SLENPTPPFtPK | cancer, colorectal carcinoma | HeLa | SEQ ID NO: 40 |
| 42 | DOCK7 | NP_212132.2 | G protein or regulator | Y169 | QVFESDEAPDGNSyQDDQDDLKRR | cancer, leukemia, chronic myelogenous (CML) | K562 | SEQ ID NO: 41 |
| | | | | | | cancer, lung, non-small cell | Jurkat | |
| 43 | RAB3IL1 | NP_037533.2 | G protein or regulator | S179 | TLVtSTPASPNRELHPQLLsPTK | cancer, cervical; adenocarcinoma | HeLa | SEQ ID NO: 42 |
| | | | | | | cancer, leukemia, chronic myelogenous (CML) | K562 | |
| 44 | RAB3IL1 | NP_037533.2 | G protein or regulator | S168 | TLVtSTPAsPNR | cancer, cervical; adenocarcinoma | HeLa | SEQ ID NO: 43 |
| 45 | RAPGEF6 | NP_057424.2 | G protein or regulator | Y1490 | GLIVyCVTSPK | cancer, leukemia | Jurkat | SEQ ID NO: 44 |
| | | | | | | cancer, colorectal carcinoma | DMS 153 HeLa HT29 | |
| | | | | | | cancer, leukemia, chronic myelogenous (CML) | | |
| | | | | | | cancer, lung, small-cell cancer, cervical; adenocarcinoma | | |
| 46 | SIPA1L1 | NP_056371.1 | G protein or regulator | S161 | FLMPEAYPsSPR | cancer, cervical; adenocarcinoma | K562 | SEQ ID NO: 45 |
| 47 | INPP4A | NP_004018.1 | Phosphatase | Y933 | HYRPPEGTyGKVET | cancer, leukemia | Jurkat | SEQ ID NO: 46 |
| 48 | HGFAC | NP_001519.1 | Protease | S388 | VQLsPDLLATLPEPAsPGR | cancer, cervical; adenocarcinoma | HeLa | SEQ ID NO: 47 |
| 49 | HGFAC | NP_001519.1 | Protease | S376 | VQLsPDILLATLPEPAsPGR | cancer, cervical; adenocarcinoma | HeLa | SEQ ID NO: 48 |
| 50 | MAP2K1 | NP_002746.1 | Protein Kinase, dual-specificity | T388 | RSDAEEVDFAGWLCSTIGLNQPSTPHAAGV | cancer, cervical; adenocarcinoma | HeLa | SEQ ID NO: 49 |
| 51 | CDK10 | NP_003665.2 | Protein Kinase, Ser/Thr (non-receptor) | T167 | AYGVPVKPMtPK | cancer, cervical; adenocarcinoma | HeLa | SEQ ID NO: 50 |
| 52 | DCAMKL1 | NP_004725.1 | Protein Kinase, Ser/Thr (non-receptor) | S334 | SPSPsPTSPGSLRK | cancer, cervical; adenocarcinoma | HeLa | SEQ ID NO: 51 |
| 53 | DCAMKL1 | NP_004725.1 | Protein Kinase, Ser/Thr (non-receptor) | S337 | SPSPSPTsPGSSLRK | cancer, cervical; adenocarcinoma | HeLa | SEQ ID NO: 52 |
| 54 | DCAMKL1 | NP_004725.1 | Protein Kinase, Ser/Thr (non-receptor) | S340 | SPSPSPTSPGsLRK | cancer, cervical; adenocarcinoma | HeLa | SEQ ID NO: 53 |

FIG. 2E

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 55 | HIPK1 | NP_852003.1 | Protein kinase, Ser/Thr (non-receptor) | S806 | GSTIYTGYPLsPTK | cancer, colorectal carcinoma cancer, leukemia, cancer, leukemia, chronic myelogenous (CML) cancer, lung, small-cell cancer, cervical, adenocarcinoma | DMS 153 HeLa Jurkat K562 | SEQ ID NO: 54 |
| 56 | KIAA2002 | XP_370878.2 | Protein kinase, Ser/Thr (non-receptor) | Y463 | GLDIESyDSLERPLRK | cancer, leukemia cancer, cervical, adenocarcinoma | Jurkat | SEQ ID NO: 55 |
| 57 | ABL1 | NP_005148.2 | Protein kinase, Tyr (receptor) | T852 | GSALGtPAAAEPYMPTSK | cancer, colorectal carcinoma cancer, leukemia cancer, cervical, adenocarcinoma cancer, leukemia, chronic myelogenous (CML) | HeLa Jurkat K562 | SEQ ID NO: 56 |
| 58 | ZAP70 | NP_001070.2 | Protein kinase, Tyr (non-receptor) | Y87 | AHCGPAELCEFyRDPDGLPCNLR | cancer, leukemia | Jurkat | SEQ ID NO: 57 |
| 59 | EPHA8 | NP_001006944.1 | Protein kinase, Tyr (receptor) | S444 | NsVPQRPGPPASPASDPSR | cancer, cervical, adenocarcinoma | HeLa | SEQ ID NO: 58 |
| 60 | EPHA8 | NP_001006944.1 | Protein kinase, Tyr (receptor) | S454 | NSVPQRPGPPAsPASDPSR | cancer, cervical, adenocarcinoma | HeLa | SEQ ID NO: 59 |
| 61 | EPHA8 | NP_001006944.1 | Protein kinase, Tyr (receptor) | S460 | NSVPQRPGPPASPASDPsR | cancer, cervical, adenocarcinoma | HeLa | SEQ ID NO: 60 |
| 62 | ABCE1 | NP_002931.2 | Receptor, channel, transporter or cell su | Y594 | KSGNyFLDD | cancer, leukemia | Jurkat | SEQ ID NO: 61 |
| 63 | ABCF3 | NP_060828.1 | Receptor, channel, transporter or cell su | Y100 | ITENyDCGTKLPGLLKR | cancer, leukemia cancer, cervical, adenocarcinoma | Jurkat HeLa | SEQ ID NO: 62 |
| 64 | CACNA1A | NP_075461.1 | Receptor, channel, transporter or cell su | T2290 | RQLPQtPSTPRPHVSYSPVIR | cancer, cervical, adenocarcinoma | HeLa | SEQ ID NO: 63 |
| 65 | CACNA1A | NP_075461.1 | Receptor, channel, transporter or cell su | S2299 | RQLPQTPSTPRPHVsYSPVIR | cancer, cervical, adenocarcinoma | HeLa | SEQ ID NO: 64 |
| 66 | IGSF6 | NP_005840.2 | Receptor, channel, transporter or cell su | S54 | CTFsATGCPSEQPTCLWFR | cancer, cervical, adenocarcinoma | HeLa | SEQ ID NO: 65 |
| 67 | IGSF6 | NP_005840.2 | Receptor, channel, transporter or cell su | T56 | CTFSAtGCPSEQPTCLWFR | cancer, cervical, adenocarcinoma | HeLa | SEQ ID NO: 66 |
| 68 | IGSF6 | NP_005840.2 | Receptor, channel, transporter or cell su | T64 | CTFSATGCPSEQPtCLWFR | cancer, cervical, adenocarcinoma | HeLa | SEQ ID NO: 67 |
| 69 | HNRPD | NP_002129.2 | RNA binding protein | T193 | IFVGGLSPDtPEEK | cancer, colorectal carcinoma cancer, leukemia, chronic myelogenous (CML) cancer, cervical, adenocarcinoma | HeLa K562 | SEQ ID NO: 68 |

FIG 2F

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO. |
| 70 | HNRPH2 | NP_062543.1 | RNA binding protein | | | cancer, cervical, adenocarcinoma cancer, colorectal carcinoma cancer, leukemia, cancer, leukemia, chronic lymphocytic (CLL) cancer, leukemia, chronic myelogenous (CML) cancer, lung, non-small cell cancer, lung, small-cell | HeLa Jurkat | |
| 71 | PCBP1 | NP_006187.1 | RNA binding protein | S104 | HTGPNsPDTANDGFVR | cancer, pancreatic cancer, leukemia | K562 Jurkat | SEQ ID NO: 69 SEQ ID NO: 70 |
| | | | | Y183 | VMTIPyQPMPASSPVICAGGQDR | cancer, cervical, adenocarcinoma cancer, colorectal carcinoma cancer, leukemia cancer, leukemia, chronic myelogenous (CML) | HeLa Jurkat | |
| 72 | SRRM2 | NP_057417.2 | RNA binding protein | T2289 | TAVAPSAVNLADPRHPTAPAVNLAGAR | cancer, leukemia | K562 | SEQ ID NO: 71 |
| 73 | SRRM2 | NP_057417.2 | RNA binding protein | Y1049 | SSTPPGESyFGVSSLQLK | cancer, cervical, adenocarcinoma | Jurkat | SEQ ID NO: 72 |
| 74 | TARBP2 | NP_004169.3 | RNA binding protein | S131 | SPPMELQPPVsPQQSECNPVGALQELVVQK | cancer, colorectal carcinoma cancer, leukemia, chronic myelogenous (CML) | HeLa | SEQ ID NO: 73 |
| 75 | ATF7 | NP_006847.1 | Transcriptional regulator | S97 | AAAGPLDMsLPSTPDIK | cancer, cervical, adenocarcinoma cancer, colorectal carcinoma cancer, leukemia, chronic myelogenous (CML) | HeLa HT29 | SEQ ID NO: 74 |
| 76 | ATF7 | NP_006847.1 | Transcriptional regulator | T101 | AAAGPLDMSLPSlPDIK | cancer, cervical, adenocarcinoma | HeLa K562 | SEQ ID NO: 75 |

FIG. 2G

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 77 | CHD8 | NP_065971.1 | Transcriptional regulator | S2240 | APGYPSsPVTTASGITLR | cancer, cervical, adenocarcinoma, cancer, colorectal carcinoma, cancer, leukemia, cancer, leukemia, chronic lymphocytic (CLL), cancer, leukemia, chronic myelogenous (CML), cancer, lung, non-small cell, cancer, lung, small-cell | HeLa, Jurkat, K562 | SEQ ID NO: 76 |
| 78 | DMAP1 | NP_061973.1 | Transcriptional regulator | T409 | AGVLGGPAtPAsGPGPASAEPAVTEPGLGPDPK | cancer, colorectal carcinoma, cancer, leukemia, cancer, leukemia, chronic myelogenous (CML), cancer, cervical, adenocarcinoma | HeLa, K562 | SEQ ID NO: 77 |
| 79 | DMAP1 | NP_061973.1 | Transcriptional regulator | S412 | AGVLGGPATPAsSPGPASAEPAVTEPGLGPDPK | cancer, cervical, adenocarcinoma | HeLa | SEQ ID NO: 78 |
| 80 | ECD | NP_009196.1 | Transcriptional regulator | Y448 | ESESVSKEEKEQNVDLTEVSESMK | cancer, leukemia | Jurkat | SEQ ID NO: 79 |
| 81 | GTF3C5 | NP_036219.1 | Transcriptional regulator | Y194 | EGvNNPPISGENLIGLSR | cancer, leukemia | Jurkat | SEQ ID NO: 80 |
| 82 | HEXIM2 | NP_653209.1 | Transcriptional regulator | T32 | TSGAPGSPQPPERHDSGGSLPLTPR | cancer, cervical, adenocarcinoma | HeLa | SEQ ID NO: 81 |
| 83 | HEXIM2 | NP_653209.1 | Transcriptional regulator | T46 | TSGAPGSPQTPPERHDSGGSLPLPR | cancer, cervical, adenocarcinoma | HeLa | SEQ ID NO: 82 |
| 84 | MLL2 | NP_003473.1 | Transcriptional regulator | S4547 | IPNSYEVLFPEsPAR | cancer, colorectal carcinoma, cancer, leukemia, chronic myelogenous (CML), cancer, lung, small-cell, cancer, cervical, adenocarcinoma | DMS 153, HeLa, K562 | SEQ ID NO: 83 |
| 85 | PPP1R13L | NP_006354.2 | Transcriptional regulator | Y126 | TPLyLQPDAYGSSLDR | cancer, leukemia | Jurkat | SEQ ID NO: 84 |
| 86 | RB1 | NP_000312.2 | Transcriptional regulator | S794 | SPYKFPsSPLR | cancer, cervical, adenocarcinoma | HeLa, HT29 | SEQ ID NO: 85 |
| 87 | SAP30BP | NP_053036.2 | Transcriptional regulator | T60 | LGLPPLtPEQQEALQK | cancer, colorectal | HeLa | SEQ ID NO: 86 |

FIG. 2H

| | Protein Name | Accession No. | Protein Type | Phospho-Residue | Phosphorylation Site Sequence | Disease | Cell Line / Tissue / Patient | SEQ ID NO |
|---|---|---|---|---|---|---|---|---|
| 88 | SUPT5H | NP_003160.2 | Transcriptional regulator | T1034 | VVSISSEHLEPtPTKNMK | cancer, cervical, adenocarcinoma cancer, leukemia, chronic myelogenous (CML) | HeLa K562 | SEQ ID NO: 87 |
| 89 | SUPT5H | NP_003160.2 | Transcriptional regulator | T1036 | VVSISSEHLEPITPtKNMK | no information cancer, leukemia, chronic myelogenous (CML) | | SEQ ID NO: 88 |
| 90 | YBX1 | NP_004550.2 | Transcriptional regulator | Y238 | RPQYSNPPVQGEVMEGADNQGAGEQGRPVRQNMyR | cancer, cervical, adenocarcinoma | HeLa | SEQ ID NO: 89 |
| 91 | ZNFN1A1 | NP_006651.1 | Transcriptional regulator | Y413 | SGLVLTNHIAPHAR | cancer, leukemia | Jurkat | SEQ ID NO: 90 |
| 92 | EEF1G | NP_001395.1 | Translational regulator | S387 | GQELAFPLsPDKQVDYESYTWR | cancer, lung, small-cell cancer, cervical, adenocarcinoma | DMS 53 HeLa | SEQ ID NO: 91 |
| 93 | CCDC86 | NP_077003.1 | Ubiquitin conjugating system | S21 | RLGGLRPESPEsLTSVSR | cancer, cervical, adenocarcinoma | HeLa | SEQ ID NO: 92 |
| 94 | UFD1L | NP_005650.2 | Ubiquitin conjugating system | Y219 | QVQHEESTEGEADHSGyAGELGFR | cancer, leukemia | Jurkat | SEQ ID NO: 93 |
| 95 | USP11 | NP_004642.2 | Ubiquitin conjugating system | S948 | RLLSPAGSSGAPAsPACSSPPSSEFMDVN | cancer, cervical, adenocarcinoma | HeLa | SEQ ID NO: 94 |
| 96 | USP11 | NP_004642.2 | Ubiquitin conjugating system | S938 | RLLsPAGSSGAPASPACSSPPSSEFMDVN | cancer, cervical, adenocarcinoma | HeLa | SEQ ID NO: 95 |
| 97 | USP15 | AAD41096.1 | Ubiquitin conjugating system | S229 | GPSTPKsPGASNFSTLPK | cancer, leukemia | Jurkat | SEQ ID NO: 96 |
| 98 | ANKRD50 | NP_085070.1 | Unknown function | Y1299 | VLEVEMTQFDRR | cancer, cervical, adenocarcinoma | HeLa | SEQ ID NO: 97 |
| 99 | ASXL2 | NP_060733.3 | Unknown function | T27 | YPNPMSHK | cancer, colorectal carcinoma cancer, lung, small-cell cancer, cervical, adenocarcinoma | HeLa HT29 | SEQ ID NO: 98 |
| 100 | ATXN2L | NP_009176.2 | Unknown function | S684 | STSTPTsPCPR | cancer, cervical, adenocarcinoma | HeLa | SEQ ID NO: 99 |
| 101 | ATXN2L | NP_009176.2 | Unknown function | T683 | STSTPtSPGPR | cancer, cervical, adenocarcinoma | HeLa | SEQ ID NO: 100 |
| 102 | BCORL1 | BAC85922.1 | Unknown function | T161 | SPTPVKPTEPCtPSK | cancer, leukemia | Jurkat | SEQ ID NO: 101 |
| 103 | C11orf2 | NP_037397.2 | Unknown function | Y651 | TFSVySSSR | cancer, cervical, adenocarcinoma | HeLa | SEQ ID NO: 102 |
| 104 | C13orf8 | NP_115812.1 | Unknown function | S389 | SSSsVSPSSWKSPPASPEsWK | cancer, cervical, adenocarcinoma | HeLa | SEQ ID NO: 103 |
| 105 | C13orf8 | NP_115812.1 | Unknown function | S376 | SSSVsPSSWKSPPASPESWK | cancer, cervical, adenocarcinoma | HeLa | SEQ ID NO: 104 |
| 106 | C20orf114 | NP_149974.2 | Unknown function | S483 | DALVLTPASLVKPsSPVsQ | cancer, cervical, adenocarcinoma | HeLa | SEQ ID NO: 105 |
| 107 | C20orf114 | NP_149974.2 | Unknown function | S474 | DALVLTPASLVKPSSPVsQ | cancer, cervical, adenocarcinoma | HeLa | SEQ ID NO: 106 |
| 108 | C20orf114 | NP_149974.2 | Unknown function | S479 | DALVLTPASLVKPsSPVSQ | cancer, cervical, adenocarcinoma | HeLa | SEQ ID NO: 107 |

FIG. 2I

| | A | B | C | D | E | F | G | H |
|---|---|---|---|---|---|---|---|---|
| | Protein Name | Accession No. | Protein Type | Phospho-Residue | Phosphorylation Site Sequence | Disease | Cell Line / Tissue / Patient | SEQ ID NO. |
| 109 | C6orf194 | NP_001007532 | Unknown function | S23 | RSsSGsPPSPQSR | cancer, cervical; adenocarcinoma | HeLa | SEQ ID NO: 108 |
| 110 | C6orf194 | NP_001007532 | Unknown function | S24 | RSSsGSPPSPQSR | cancer, cervical; adenocarcinoma | HeLa | SEQ ID NO: 109 |
| 111 | C6orf194 | NP_001007532 | Unknown function | S26 | RSSSGsPPSPQSR | cancer, cervical; adenocarcinoma | HeLa | SEQ ID NO: 110 |
| 112 | C9orf30 | NP_542386.1 | Unknown function | S274 | EWPVSSFNRPFPNsP | cancer, cervical; adenocarcinoma | HeLa | SEQ ID NO: 111 |
| 113 | DNAJA5 | NP_919259.3 | Unknown function | Y81 | GGFDGEyQDDSLDLLR | cancer, leukemia | Jurkat | SEQ ID NO: 112 |
| 114 | FAM120A | NP_055427.2 | Unknown function | Y431 | HTPLyER | cancer, leukemia | Jurkat | SEQ ID NO: 113 |
| 115 | FAM122A | NP_612206.3 | Unknown function | S76 | HGLLLPAsPVR | cancer, colorectal carcinoma; cancer, leukemia; chronic myelogenous (CML); cancer, lung, small-cell; cancer, cervical; adenocarcinoma | HeLa K562 | SEQ ID NO: 114 |
| 116 | FAM122B | NP_660327.2 | Unknown function | S115 | RIDFTPVsPAPSPTR | cancer, colorectal carcinoma; cancer, leukemia; cancer, leukemia; chronic myelogenous (CML); cancer, lung, non-small cell; cancer, lung, small-cell; cancer, pancreatic; cancer, cervical; adenocarcinoma | DMS 153 H-526 HeLa Jurkat K562 | SEQ ID NO: 115 |
| 117 | FAM122B | NP_660327.2 | Unknown function | S119 | RIDFTPVSPAPsPTR | cancer, colorectal carcinoma; cancer, leukemia; cancer, leukemia; chronic myelogenous (CML); cancer, lung, non-small cell; cancer, lung, small-cell; cancer, pancreatic; cancer, cervical; adenocarcinoma | DMS 153 H-526 HeLa Jurkat K562 | SEQ ID NO: 116 |

FIG. 2J

| | A | B | C | D | E | F | G | H |
|---|---|---|---|---|---|---|---|---|
| | Protein Name | Accession No. | Protein Type | Phospho-Residue | Phosphorylation Site Sequence | Disease | Cell Line / Tissue / Patient | SEQ ID NO. |
| 118 | FAM122B | NP_660327.2 | Unknown function | S137 | MFVSSSGLPPsPVPSPR | cancer, colorectal carcinoma cancer, leukemia, chronic lymphocytic (CLL) cancer, leukemia, chronic myelogenous (CML) cancer, lung, non-small cell cancer, lung, small-cell cancer, pancreatic cancer, cervical, adenocarcinoma | H526 HeLa K562 MO1043 | SEQ ID NO: 117 |
| 119 | FAM122B | NP_660327.2 | Unknown function | S141 | MFVSSSGLPPSPVPsPR | cancer, colorectal carcinoma cancer, leukemia, chronic lymphocytic (CLL) cancer, leukemia, chronic myelogenous (CML) cancer, lung, non-small cell cancer, lung, small-cell cancer, pancreatic cancer, cervical, adenocarcinoma | H526 HeLa K562 | SEQ ID NO: 118 |
| 120 | FBXL20 | NP_116264.2 | Unknown function | T417 | VHAVtAPVMPPPSVCGSR | cancer, colorectal carcinoma cancer, leukemia, chronic myelogenous (CML) cancer, cervical, adenocarcinoma | HeLa | SEQ ID NO: 119 |
| 121 | FLJ14640 | NP_116205.3 | Unknown function | Y157 | GGHSDDLyAVPHR | cancer, leukemia | K562 | SEQ ID NO: 120 |
| 122 | KIAA0692 | XP_931034.1 | Unknown function | Y256 | GICDyFPSPSK | cancer, leukemia | Jurkat | SEQ ID NO: 121 |
| 123 | KIAA1012 | NP_057754.2 | Unknown function | S971 | RPEFFTFGGNTAVLTPLsPSASENCSAYK | cancer, cervical, adenocarcinoma cancer, leukemia, chronic lymphocytic (CLL) cancer, leukemia, chronic myelogenous (CML) cancer, lung, small-cell | DMS 153 DMS 53 DMS 79 HeLa K562 | SEQ ID NO: 122 |

FIG. 2K

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 124 | KIAA1458 | XP_044434.3 | Unknown function | S247 | SSDRNPPLsPQSSIDSELSASELDEDSIGSNYK | cancer, cervical, adenocarcinoma cancer, leukemia, chronic lymphocytic (CLL) | HeLa | SEQ ID NO: 123 |
| 125 | KIDINS220 | NP_065789.1 | Unknown function | S1555 | VPKsPEHSAEPIR | cancer, cervical, adenocarcinoma cancer, leukemia, chronic lymphocytic (CLL) | HeLa | SEQ ID NO: 124 |
| 126 | LEREPO4 | NP_060941.1 | Unknown function | Y358 | FStyTSDKDENKLSEASGGR | cancer, leukemia | K562 | SEQ ID NO: 125 |
| 127 | LMO7 | NP_005349.3 | Unknown function | Y348 | SWASPVyTEADGTFSR | cancer, leukemia | Jurkat | SEQ ID NO: 126 |
| 128 | LOC149950 | NP_001010976.1 | Unknown function | S109 | QIPPPQTPsTDPQTLPLSFRSLLR | cancer, cervical, adenocarcinoma | HeLa | SEQ ID NO: 127 |
| 129 | LOC149950 | NP_001010976.1 | Unknown function | S121 | QIPPPQTPSTDPQTLPLSFRsLLR | cancer, cervical, adenocarcinoma | HeLa | SEQ ID NO: 128 |
| 130 | LOC149950 | NP_001010976.1 | Unknown function | T114 | QIPPPQTPSTDPQtLPLSFRSLLR | cancer, cervical, adenocarcinoma | HeLa | SEQ ID NO: 129 |
| 131 | LOC196752 | NP_001010864.1 | Unknown function | S48 | KQsAGPNSPTGGGGGGGSGGTRMR | cancer, cervical, adenocarcinoma | HeLa | SEQ ID NO: 130 |
| 132 | LOC51255 | NP_057578.1 | Unknown function | Y152 | LENLHGAMyT | cancer, leukemia | Jurkat | SEQ ID NO: 131 |
| 133 | LOXHD1 | NP_653213.4 | Unknown function | S1523 | CLDPHSSFCPPPTPSPGSSGLsMDLVK | cancer, cervical, adenocarcinoma | HeLa | SEQ ID NO: 132 |
| 134 | LOXHD1 | NP_653213.4 | Unknown function | S1519 | CLDPHSSFCPPPTPSPGsGGLSMDLVK | cancer, cervical, adenocarcinoma | HeLa | SEQ ID NO: 133 |
| 135 | LTV1 | NP_116249.2 | Unknown function | Y243 | FTEySMTSSVMR | cancer, leukemia | Jurkat | SEQ ID NO: 134 |
| 136 | MAGEC1 | AAC18937.1 | Unknown function | S266 | TQSTFEGFPGsPLQIPVSR | cancer, lung, small-cell chronic myelogenous (CML) | K562 | SEQ ID NO: 135 |
| 137 | MGC22793 | NP_659467.1 | Unknown function | S87 | LTPPsPVRSEPQPAVPQCELEMPVLK | cancer, colorectal carcinoma cancer, leukemia, chronic myelogenous (CML), cancer, lung, non-small cell | H69 (xenograft) HeLa | SEQ ID NO: 136 |
| 138 | N4BP1 | NP_694574.3 | Unknown function | Y415 | NKGVySSTNELTTDSTPK | cancer, cervical, adenocarcinoma cancer, leukemia | K562 Jurkat | SEQ ID NO: 137 |

FIG. 2L

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 139 | NBEAL2 | XP_291064.5 | Unknown function | T1915 | DNLGEVPLtPTEEASLPLAVTK | cancer, colorectal carcinoma, cancer, leukemia, chronic myelogenous (CML), cancer, cervical, adenocarcinoma | HeLa, K562 | SEQ ID NO: 138 |
| 140 | NIBP | NP_113664.3 | Unknown function | S1051 | MAIQYDKFNFESFPEsRGEKGQFANPK | cancer, leukemia, chronic myelogenous (CML), cancer, lung, small-cell, cancer, cervical, adenocarcinoma | HeLa, K562 | SEQ ID NO: 139 |
| 141 | PHACTR4 | NP_076412.2 | Unknown function | T416 | IQQALTSPLPMtPILEGSHR | cancer, leukemia, chronic myelogenous (CML), cancer, cervical, adenocarcinoma | HeLa, K562 | SEQ ID NO: 140 |
| 142 | RCSD1 | NP_443094.2 | Unknown function | S116 | AMVsPFHSPPSTPSsPGVR | cancer, leukemia, cancer, leukemia, chronic lymphocytic (CLL), cancer, leukemia, chronic myelogenous (CML), cancer, cervical, adenocarcinoma | HeLa, Jurkat, K562 | SEQ ID NO: 141 |
| 143 | RCSD1 | NP_443094.2 | Unknown function | S120 | AMVSPFHsPPSTPSsPGVR | cancer, leukemia, cancer, leukemia, chronic lymphocytic (CLL), cancer, leukemia, chronic myelogenous (CML), cancer, cervical, adenocarcinoma | HeLa, Jurkat, K562 | SEQ ID NO: 142 |
| 144 | RCSD1 | NP_443094.2 | Unknown function | S127 | AMVsPFHsPPSTPSsPGVR | cancer, cervical, adenocarcinoma | HeLa | SEQ ID NO: 143 |
| 145 | RNF168 | NP_699830.2 | Unknown function | Y104 | ASQEsEEVADDyQPVR | cancer, leukemia | Jurkat | SEQ ID NO: 144 |
| 146 | SVH | NP_114111.2 | Unknown function | Y89 | TSQPEDLTDGSyDDVLNAEQLQK | cancer, leukemia | Jurkat | SEQ ID NO: 145 |

FIG. 2M

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 147 | TBC1D16 | NP_061893.2 | Unknown function | T758 | KGPKtPQDGFGFRR | cancer, cervical, adenocarcinoma | HeLa | SEQ ID NO: 146 |
| 148 | THADA | NP_071348.3 | Unknown function | Y1003 | DTNDyFNQAK | cancer, leukemia | Jurkat | SEQ ID NO: 147 |
| 149 | TNRC15 | NP_056390.2 | Unknown function | Y1299 | LNMGEIETLDDy | cancer, leukemia | Jurkat | SEQ ID NO: 148 |
| 150 | VPS13D | NP_056193.2 | Unknown function | S1765 | EVQDKDYPLTPPPsPTVDEPK | cancer, colorectal carcinoma; cancer, leukemia, chronic myelogenous (CML); cancer, cervical, adenocarcinoma | HT29 | SEQ ID NO: 149 |
| 151 | VPS13D | NP_056193.2 | Unknown function | T1761 | EVQDKDYPLPPPSPTVDEPK | cancer, cervical, adenocarcinoma | HeLa K562 | SEQ ID NO: 150 |
| 152 | ZCCHC11 | NP_056084.1 | Unknown function | S104 | FPNsPVKAEK | cancer, cervical, adenocarcinoma; cancer, colorectal carcinoma; cancer, leukemia, chronic myelogenous (CML) | HeLa | SEQ ID NO: 151 |
| 153 | ZNF609 | NP_055857.1 | Unknown function | T823 | LENTTPTQPLPLHyVTQNGAEASSVK | cancer, cervical, adenocarcinoma; cancer, colorectal carcinoma; cancer, leukemia, chronic lymphocytic (CLL); cancer, leukemia, chronic myelogenous (CML); cancer, lung, non-small cell; cancer, lung, small-cell; cancer, pancreatic | HeLa K562 H526 HeLa K562 | SEQ ID NO: 152 |
| 154 | ZNF687 | NP_065883.1 | Unknown function | S140 Y3025 | MQNGFGSPEPSLPGTPHsPAPPSGGTWK QASPETSASPDGSQNLVyETELLR | cancer, cervical, adenocarcinoma | M01043 MEC-1 | SEQ ID NO: 153 SEQ ID NO: 154 |
| 155 | GOLGB1 NISCH | NP_004478.1 NP_039115.2 | Vesicle protein Vesicle protein | Y1307 | MENyELIHSSR | cancer, leukemia | Jurkat | SEQ ID NO: 155 |

TYROSINE, SERINE AND THREONINE PHOSPHORYLATION SITES

RELATED APPLICATIONS

This is a National Stage Application of International Application No. PCT/US07/019488 filed Sep. 8, 2007, which itself claims priority to U.S.S.N. 60/843,348filed Sep. 8, 2006 now abandoned, both disclosures of which are incorporated herein, in their entirety, by reference.

FIELD OF THE INVENTION

The invention relates generally to novel tyrosine, serine and threonine phosphorylation sites, methods and compositions for detecting, quantitating and modulating same.

BACKGROUND OF THE INVENTION

The activation of proteins by post-translational modification is an important cellular mechanism for regulating most aspects of biological organization and control, including growth, development, homeostasis, and cellular communication. Protein phosphorylation, for example, plays a critical role in the etiology of many pathological conditions and diseases, including to mention but a few: cancer, developmental disorders, autoimmune diseases, and diabetes. Yet, in spite of the importance of protein modification, it is not yet well understood at the molecular level, due to the extraordinary complexity of signaling pathways, and the slow development of technology necessary to unravel it.

Protein phosphorylation on a proteome-wide scale is extremely complex as a result of three factors: the large number of modifying proteins, e.g., kinases, encoded in the genome, the much larger number of sites on substrate proteins that are modified by these enzymes, and the dynamic nature of protein expression during growth, development, disease states, and aging. The human genome, for example, encodes over 520 different protein kinases, making them the most abundant class of enzymes known. (Blume-Jensen et al., Nature 411: 355-365 (2001)). Most kinases phosphorylate many different substrate proteins, at distinct tyrosine, serine, and/or threonine residues. Indeed, it is estimated that one-third of all proteins encoded by the human genome are phosphorylated, and many are phosphorylated at multiple sites by different kinases.

Many of these phosphorylation sites regulate critical biological processes and may prove to be important diagnostic or therapeutic targets for molecular medicine. For example, of the more than 100 dominant oncogenes identified to date, 46 are protein kinases. See Blume-Jensen, supra.

Protein kinases are often divided into two groups based on the amino acid residue they phosphorylate. The Ser/Thr kinases, which phosphorylate serine and/or threonine (Ser, S; Thr, T) residues, include cyclic AMP(cAMP-) and cGMP-dependent protein kinases, calcium- and phospholipid-dependent protein kinase C, calmodulin dependent protein kinases, casein kinases, cell division cycle (CDC) protein kinases, and others. These kinases are usually cytoplasmic or associated with the particulate fractions of cells, possibly by anchoring proteins. The second group of kinases, which phosphorylate Tyrosine (Tyr, T) residues, are present in much smaller quantities, but play an equally important role in cell regulation. These kinases include several receptors for molecules such as growth factors and hormones, including epidermal growth factor receptor, insulin receptor, platelet-derived growth factor receptor, and others. Some Ser/Thr kinases are known to be downstream to tyrosine kinases in cell signaling pathways.

Understanding which proteins are modified by these kinases will greatly expand our understanding of the molecular mechanisms underlying oncogenic transformation. Therefore, the identification of, and ability to detect, phosphorylation sites on a wide variety of cellular proteins is crucially important to understanding the key signaling proteins and pathways implicated in the progression of disease states; for example, cancer.

Carcinoma is one of the two main categories of cancer, and is generally characterized by the formation of malignant tumors or cells of epithelial tissue original, such as skin, digestive tract, glands, etc. Carcinomas are malignant by definition, and tend to metastasize to other areas of the body. The most common forms of carcinoma are skin cancer, lung cancer, breast cancer, and colon cancer, as well as other numerous but less prevalent carcinomas. Current estimates show that, collectively, various carcinomas will account for approximately 1.65 million cancer diagnoses in the United States alone, and more than 300,000 people will die from some type of carcinoma during 2005. (Source: American Cancer Society (2005)). The worldwide incidence of carcinoma is much higher.

As with many cancers, deregulation of receptor tyrosine kinases (RTKs) appears to be a central theme in the etiology of carcinomas. Constitutively active RTKs can contribute not only to unrestricted cell proliferation, but also to other important features of malignant tumors, such as evading apoptosis, the ability to promote blood vessel growth, the ability to invade other tissues and build metastases at distant sites (see Blume-Jensen et al., Nature 411: 355-365 (2001)). These effects are mediated not only through aberrant activity of RTKs themselves, but, in turn, by aberrant activity of their downstream signaling molecules and substrates.

The importance of RTKs in carcinoma progression has led to a very active search for pharmacological compounds that can inhibit RTK activity in tumor cells, and more recently to significant efforts aimed at identifying genetic mutations in RTKs that may occur in, and affect progression of, different types of carcinomas (see, e.g., Bardelli et al., Science 300: 949 (2003); Lynch et al., N. Eng. J. Med. 350: 2129-2139 (2004)). For example, non-small cell lung carcinoma patients carrying activating mutations in the epidermal growth factor receptor (EGFR), an RTK, appear to respond better to specific EGFR inhibitors than do patients without such mutations (Lynch et al., supra.; Paez et al., Science 304: 1497-1500 (2004)).

Clearly, identifying activated RTKs and downstream signaling molecules driving the oncogenic phenotype of carcinomas would be highly beneficial for understanding the underlying mechanisms of this prevalent form of cancer, identifying novel drug targets for the treatment of such disease, and for assessing appropriate patient treatment with selective kinase inhibitors of relevant targets when and if they become available. The identification of key signaling mechanisms is highly desirable in many contexts in addition to cancer.

It has also been shown that a number of Ser/Thr kinase family members are involved in tumor growth or cellular transformation by either increasing cellular proliferation or decreasing the rate of apoptosis. For example, the mitogen-activated protein kinases (MAPKs) are Ser/Thr kinases which act as intermediates within the signaling cascades of both growth/survival factors, such as EGF, and death receptors, such as the TNF receptor. Expression of Ser/Thr kinases, such as protein kinase A, protein kinase B and protein kinase C, have been shown be elevated in some tumor cells. Further, cyclin dependent kinases (cdk) are Ser/Thr kinases that play an important role in cell cycle regulation. Increased expression or activation of these kinases may cause uncontrolled cell proliferation leading to tumor growth. (See Cross et al., *Exp. Cell Res.* 256: 34-41, 2000).

Leukemia, another form of cancer in which a number of underlying signal transduction events have been elucidated, has become a disease model for phosphoproteomic research and development efforts. As such, it represent a paradigm leading the way for many other programs seeking to address many classes of diseases (See, *Harrison's Principles of Internal Medicine*, McGraw-Hill, New York, N.Y).

Most varieties of leukemia are generally characterized by genetic alterations e.g., chromosomal translocations, deletions or point mutations resulting in the constitutive activation of protein kinase genes, and their products, particularly tyrosine kinases. The most well known alteration is the oncogenic role of the chimeric BCR-Abl gene (see Nowell, *Science* 132: 1497 (1960)). The resulting BCR-Abl kinase protein is constitutively active and elicits characteristic signaling pathways that have been shown to drive the proliferation and survival of CML cells (see Daley, *Science* 247: 824-830 (1990); Raitano et al., *Biochim. Biophys. Acta*. December 9; 1333(3): F201-16 (1997)).

The recent success of Imanitib (also known as STI571 or Gleevec®), the first molecularly targeted compound designed to specifically inhibit the tyrosine kinase activity of BCR-Abl, provided critical confirmation of the central role of BCR-Abl signaling in the progression of CML (see Schindler et al., *Science* 289: 1938-1942 (2000); Nardi et al., *Curr. Opin. Hematol.* 11: 35-43 (2004)).

The success of Gleevec® now serves as a paradigm for the development of targeted drugs designed to block the activity of other tyrosine kinases known to be involved in many diseases including leukemias and other malignancies (see, e.g., Sawyers, *Curr. Opin. Genet. Dev.* February; 12(1): 111-5 (2002); Druker, *Adv. Cancer Res.* 91:1-30 (2004)). For example, recent studies have demonstrated that mutations in the FLT3 gene occur in one third of adult patients with AML. FLT3 (Fms-like tyrosine kinase 3) is a member of the class III receptor tyrosine kinase (RTK) family including FMS, platelet-derived growth factor receptor (PDGFR) and c-KIT (see Rosnet et al., *Crit. Rev. Oncog.* 4: 595-613 (1993). In 20-27% of patients with AML, internal tandem duplication in the juxta-membrane region of FLT3 can be detected (see Yokota et al., *Leukemia* 11: 1605-1609 (1997)). Another 7% of patients have mutations within the active loop of the second kinase domain, predominantly substitutions of aspartate residue 835 (D835), while additional mutations have been described (see Yamamoto et al., *Blood* 97: 2434-2439 (2001); Abu-Duhier et al., *Br. J. Haematol.* 113: 983-988 (2001)). Expression of mutated FLT3 receptors results in constitutive tyrosine phosphorylation of FLT3, and subsequent phosphorylation and activation of downstream molecules such as STAT5, Akt and MAPK, resulting in factor-independent growth of hematopoietic cell lines.

Altogether, FLT3 is the single most common activated gene in AML known to date. This evidence has triggered an intensive search for FLT3 inhibitors for clinical use leading to at least four compounds in advanced stages of clinical development, including: PKC412 (by Novartis), CEP-701 (by Cephalon), MLN518 (by Millenium Pharmaceuticals), and SU5614 (by Sugen/Pfizer) (see Stone et al., *Blood* 105: 54-60 (2005); Smith et al., *Blood* 103: 3669-3676 (2004); Clark et al., *Blood* 104: 2867-2872 (2004); and Spiekermann et al., *Blood* 101: 1494-1504 (2003)).

There is also evidence indicating that kinases such as FLT3, c-KIT and Abl are implicated in some cases of ALL (see Cools et al., *Cancer Res.* 64: 6385-6389 (2004); Hu, *Nat. Genet.* 36: 453-461 (2004); and Graux et al., *Nat. Genet.* 36-1084-1089 (2004)). In contrast, very little is known regarding any causative role of protein kinases in CLL, except for a high correlation between high expression of the tyrosine kinase ZAP70 and the more aggressive form of the disease (see Rassenti et al., *N. Eng. J. Med.* 351: 893-901 (2004)).

It should also be noted that although most of the research effort has been focused on tyrosine kinases, a small of group of serine/threonine kinases, cyclin dependent kinase (Cdks), Erks, Raf, PI3K, PKB, and Akt, have been identified as major players in cell proliferation, cell division, and anti-apoptotic signaling. Akt/PKB (protein kinase B) kinases mediate signaling pathways downstream of activated tyrosine kinases and phosphatidylinositol 3-kinase. Akt kinases regulate diverse cellular processes including cell proliferation and survival, cell size and response to nutrient availability, tissue invasion and angiogenesis. Many oncoproteins and tumor suppressors implicated in cell signaling/metabolic regulation converge within the Akt signal transduction pathway in an equilibrium that is altered in many human cancers by activating and inactivating mechanisms, respectively, targeting these inter-related proteins.

Despite the identification of a few key signaling molecules involved in cancer and other disease progression, the vast majority of signaling protein changes and signaling pathways underlying these disease types remain unknown. Therefore, there is presently an incomplete and inaccurate understanding of how protein activation within signaling pathways drives various diseases including these complex cancers. Accordingly, there is a continuing and pressing need to unravel the molecular mechanisms of disease progression by identifying the downstream signaling proteins mediating cellular transformation in these diseases.

Presently, diagnosis of many diseases including carcinoma and leukemia is made by tissue biopsy and detection of different cell surface markers. However, misdiagnosis can occur since some disease types can be negative for certain markers and because these markers may not indicate which genes or protein kinases may be deregulated. Although the genetic translocations and/or mutations characteristic of a particular form of a disease including cancer can be sometimes detected, it is clear that other downstream effectors of constitutively active signaling molecules having potential diagnostic, predictive, or therapeutic value, remain to be elucidated.

Accordingly, identification of downstream signaling molecules and phosphorylation sites involved in different types of diseases including for example, carcinoma or leukemia and development of new reagents to detect and quantify these sites and proteins may lead to improved diagnostic/prognostic markers, as well as novel drug targets, for the detection and treatment of many diseases.

SUMMARY OF THE INVENTION

The present invention provides in one aspect novel tyrosine, serine and/or threonine phosphorylation sites (Table 1) identified in carcinoma and leukemia. The novel sites occur in proteins such as: Adaptor/Scaffold proteins, adhesion/extra cellular matrix proteins, apoptosis proteins, calcium binding proteins, cell cycle regulation, proteins, chromatin or DNA binding/repair/proteins, calcium binding proteins, chaperone proteins, cytoskeleton proteins, endoplasmic reticulum or golgi proteins, enzyme proteins, g proteins or regulator proteins, kinases, lipid binding proteins, protein kinases receptor/channel/transporter/cell surface proteins, RNA binding proteins, translational regulators, transcriptional regulators, ubiquitan conjugating proteins, proteins of unknown function and vesicle proteins.

In another aspect, the invention provides peptides comprising the novel phosphorylation sites of the invention, and proteins and peptides that are mutated to eliminate the novel phosphorylation sites.

In another aspect, the invention provides modulators that modulate tyrosine, serine and/or threonine phosphorylation at a novel phosphorylation sites of the invention, including small molecules, peptides comprising a novel phosphorylation site, and binding molecules that specifically bind at a novel phosphorylation site, including but not limited to antibodies or antigen-binding fragments thereof.

In another aspect, the invention provides compositions for detecting, quantitating or modulating a novel phosphorylation site of the invention, including peptides comprising a novel phosphorylation site and antibodies or antigen-binding fragments thereof that specifically bind at a novel phosphorylation site. In certain embodiments, the compositions for detecting, quantitating or modulating a novel phosphorylation site of the invention are Heavy-Isotype Labeled Peptides (AQUA peptides) comprising a novel phosphorylation site.

In another aspect, the invention discloses phosphorylation site specific antibodies or antigen-binding fragments thereof. In one embodiment, the antibodies specifically bind to an amino acid sequence comprising a phosphorylation site identified in Table 1 when the tyrosine, serine and/or threonine identified in Column D is phosphorylated, and do not significantly bind when the tyrosine, serine and/or threonine is not phosphorylated. In another embodiment, the antibodies specifically bind to an amino acid sequence comprising a phosphorylation site when the tyrosine, serine and/or threonine is not phosphorylated, and do not significantly bind when the tyrosine, serine and/or threonine is phosphorylated.

In another aspect, the invention provides a method for making phosphorylation site-specific antibodies.

In another aspect, the invention provides compositions comprising a peptide, protein, or antibody of the invention, including pharmaceutical compositions.

In a further aspect, the invention provides methods of treating or preventing carcinoma in a subject, wherein the carcinoma is associated with the phosphorylation state of a novel phosphorylation site in Table 1, whether phosphorylated or dephosphorylated. In certain embodiments, the methods comprise administering to a subject a therapeutically effective amount of a peptide comprising a novel phosphorylation site of the invention. In certain embodiments, the methods comprise administering to a subject a therapeutically effective amount of an antibody or antigen-binding fragment thereof that specifically binds at a novel phosphorylation site of the invention.

In a further aspect, the invention provides methods for detecting and quantitating phosphorylation at a novel tyrosine, serine and/or threonine phosphorylation site of the invention.

In another aspect, the invention provides a method for identifying an agent that modulates a tyrosine, serine and/or threonine phosphorylation at a novel phosphorylation site of the invention, comprising: contacting a peptide or protein comprising a novel phosphorylation site of the invention with a candidate agent, and determining the phosphorylation state or level at the novel phosphorylation site. A change in the phosphorylation state or level at the specified tyrosine, serine and/or threonine in the presence of the test agent, as compared to a control, indicates that the candidate agent potentially modulates tyrosine, serine and/or threonine phosphorylation at a novel phosphorylation site of the invention.

In another aspect, the invention discloses immunoassays for binding, purifying, quantifying and otherwise generally detecting the phosphorylation of a protein or peptide at a novel phosphorylation site of the invention.

Also provided are pharmaceutical compositions and kits comprising one or more antibodies or peptides of the invention and methods of using them.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A-2M are a table (corresponding to Table 1) summarizing the 155 novel phosphorylation sites of the invention: Column A=the parent proteins from which the phosphorylation sites are derived; Column B=the SwissProt accession number for the human homologue of the identified parent proteins; Column C=the protein type/classification; Column D=the tyrosine, serine and/or threonine residues at which phosphorylation occurs (each number refers to the amino acid residue position of the tyrosine, serine and/or threonine in the parent human protein, according to the published sequence retrieved by the SwissProt accession number); Column E=flanking sequences of the phosphorylatable tyrosine, serine and/or threonine residues; sequences (SEQ ID NOs: 1-155) were identified using Trypsin digestion of the parent proteins; in each sequence, the tyrosine, serine and/or threonine (see corresponding rows in Column D) appears in lowercase; Column F=the type of diseases with which the phosphorylation site is associated; Column G=the cell type(s)/Tissue/Patient Sample in which each of the phosphorylation site was discovered; and Column H=the SEQ ID NOs of the trypsin-digested peptides identified in Column E.

DETAILED DESCRIPTION OF THE INVENTION

The inventors have discovered and disclosed herein novel tyrosine, serine and/or threonine phosphorylation sites in signaling proteins extracted from the cell line/tissue/patient sample listed in column G of FIGS. 2A-2M. The newly discovered phosphorylation sites significantly extend our knowledge of kinase substrates and of the proteins in which the novel sites occur. The disclosure herein of the novel phosphorylation sites and reagents including peptides and antibodies specific for the sites add important new tools for the elucidation of signaling pathways that are associate with a host of biological processes including cell division, growth, differentiation, developmental changes and disease. Their discovery in carcinoma and leukemia cells provides and focuses further elucidation of the disease process. And, the novel sites provide additional diagnostic and therapeutic targets.

1. Novel Phosphorylation Sites in Carcinoma and Leukemia

In one aspect, the invention provides 155 novel tyrosine, serine and/or threonine phosphorylation sites in signaling proteins from cellular extracts from a variety of human carcinoma and leukemia-derived cell lines and tissue samples (such as HeLa, K562 and Jurkat etc., as further described below in Examples), identified using the techniques described in "Immunoaffinity Isolation of Modified Peptides From Complex Mixtures," U.S. Patent Publication No. 20030044848, Rush et al., using Table 1 summarizes the identified novel phosphorylation sites.

These phosphorylation sites thus occur in proteins found in carcinoma and leukemia. The sequences of the human homologues are publicly available in SwissProt database and their Accession numbers listed in Column B of Table 1. The novel sites occur in proteins such as: adaptor/scaffold proteins, protein kinases, enzyme proteins, ubiquitan conjugating system proteins, chromatin or DNA binding/repair proteins, g proteins or regulator proteins, receptor/channel/transporter/cell surface proteins, RNA binding proteins, transcriptional regulators and adhesion/extra-cellular matrix proteins. (see Column C of Table 1).

Figure 1:
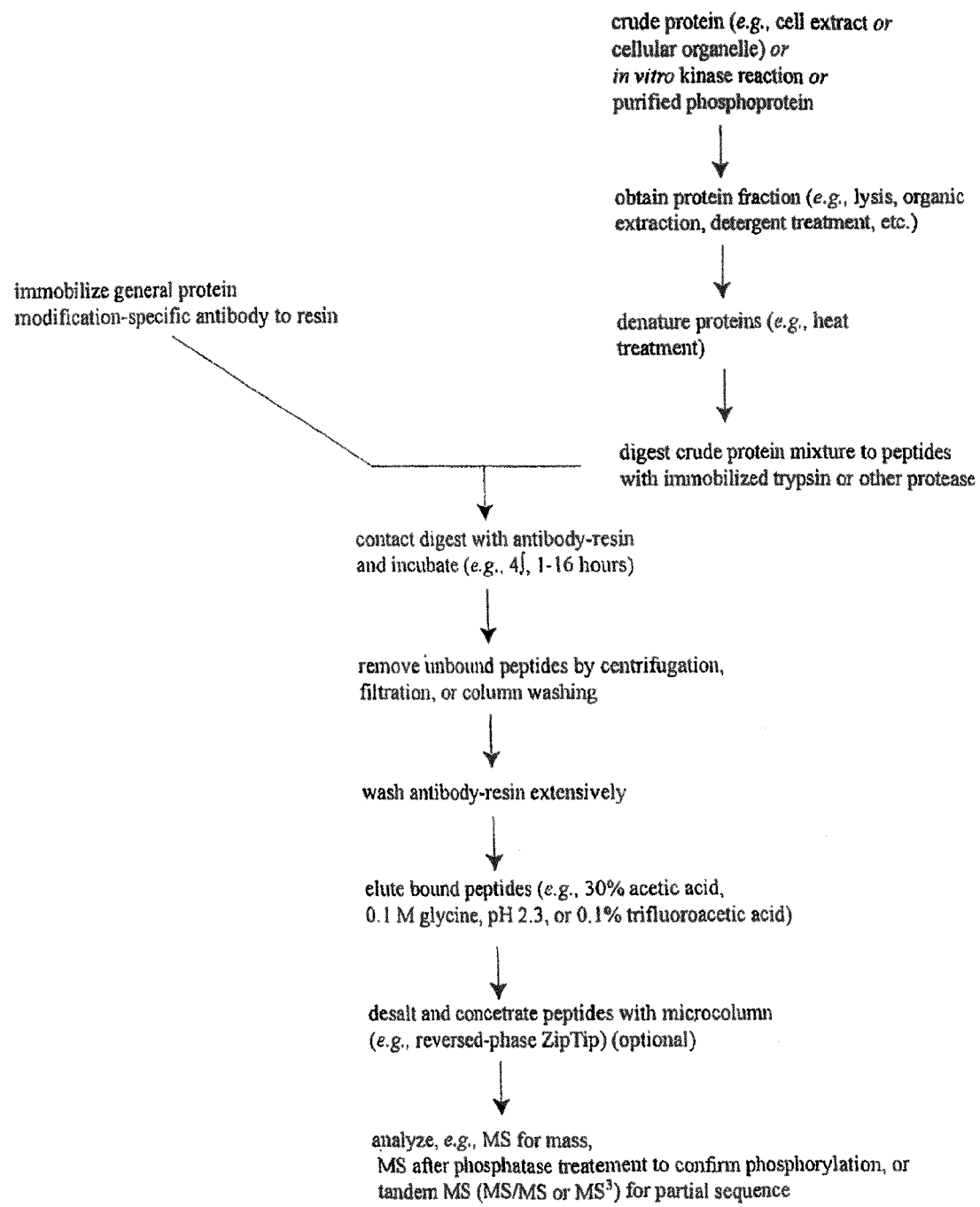
FIG. 1 is a diagram depicting the immuno-affinity isolation and mass-spectrometric characterization methodology (IAP) used in the Examples to identify the novel phosphorylation sites disclosed herein.
Figure 3:
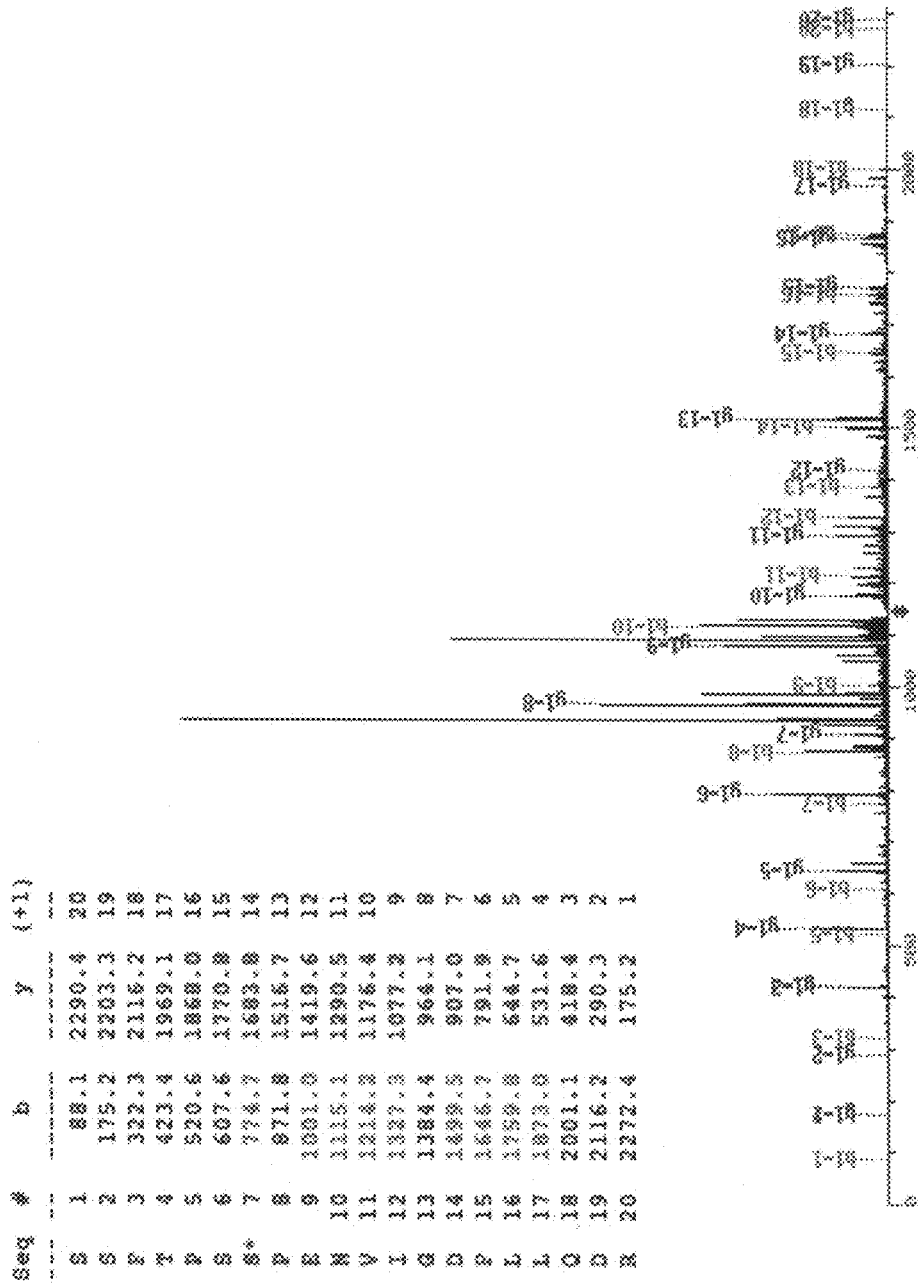
FIG. 3 is an exemplary mass spectrograph depicting the detection of the phosphorylation of serine 537 in HIVEP1, as further described in Example 1 (red and blue indicate ions detected in MS/MS spectrum); S* (and pS) indicates the phosphorylated serine (corresponds to lowercase "s" in Column E of Table 1; SEQ ID NO: 20).
Figure 4:
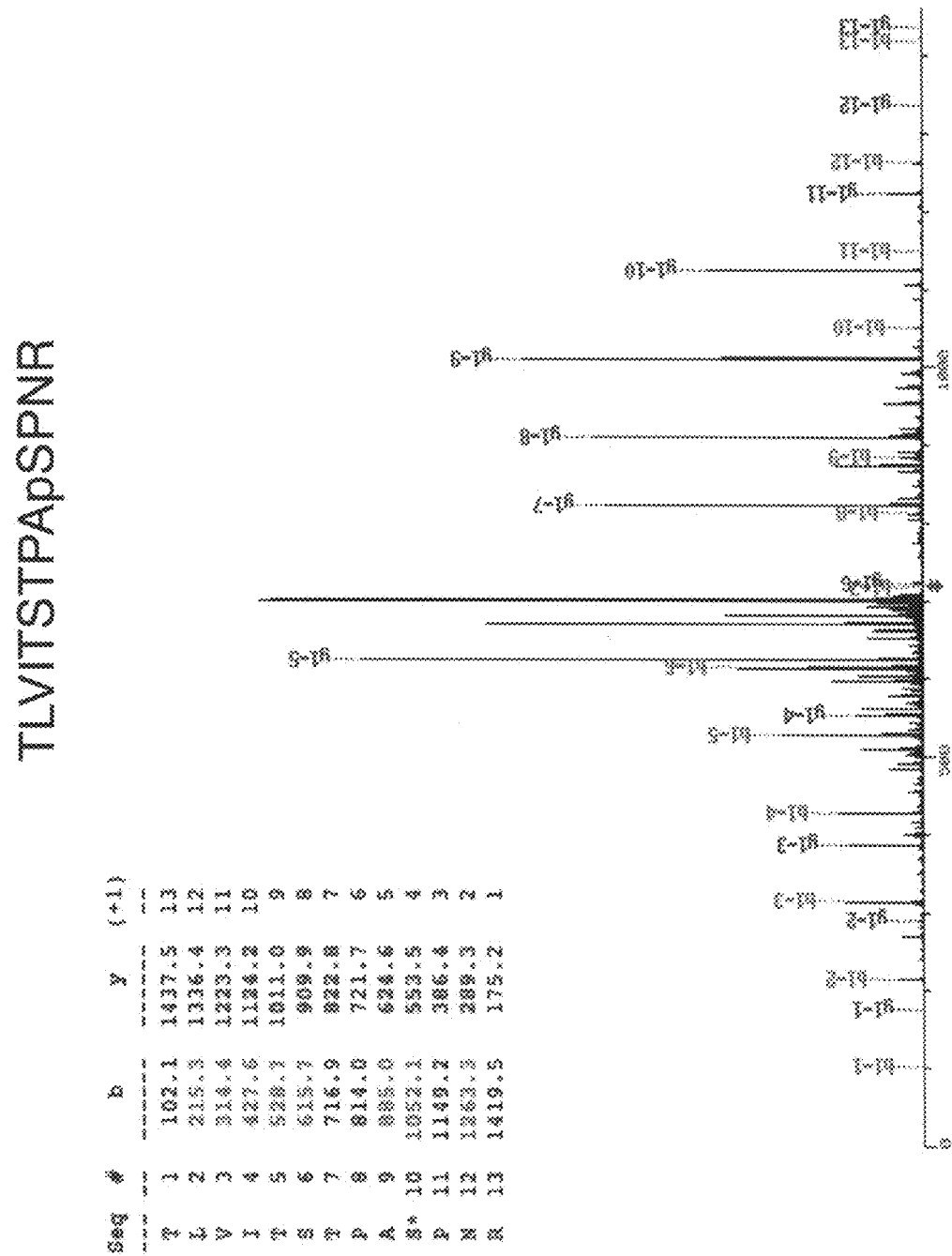
FIG. 4 is an exemplary mass spectrograph depicting the detection of the phosphorylation of serine-168 in RAB3IL, as further described in Example 1 (red and blue indicate ions detected in MS/MS spectrum); S* (and pS) indicates the phosphorylated serine (corresponds to lowercase "s" in Column E of Table 1; SEQ ID NO: 43).
Figure 5:
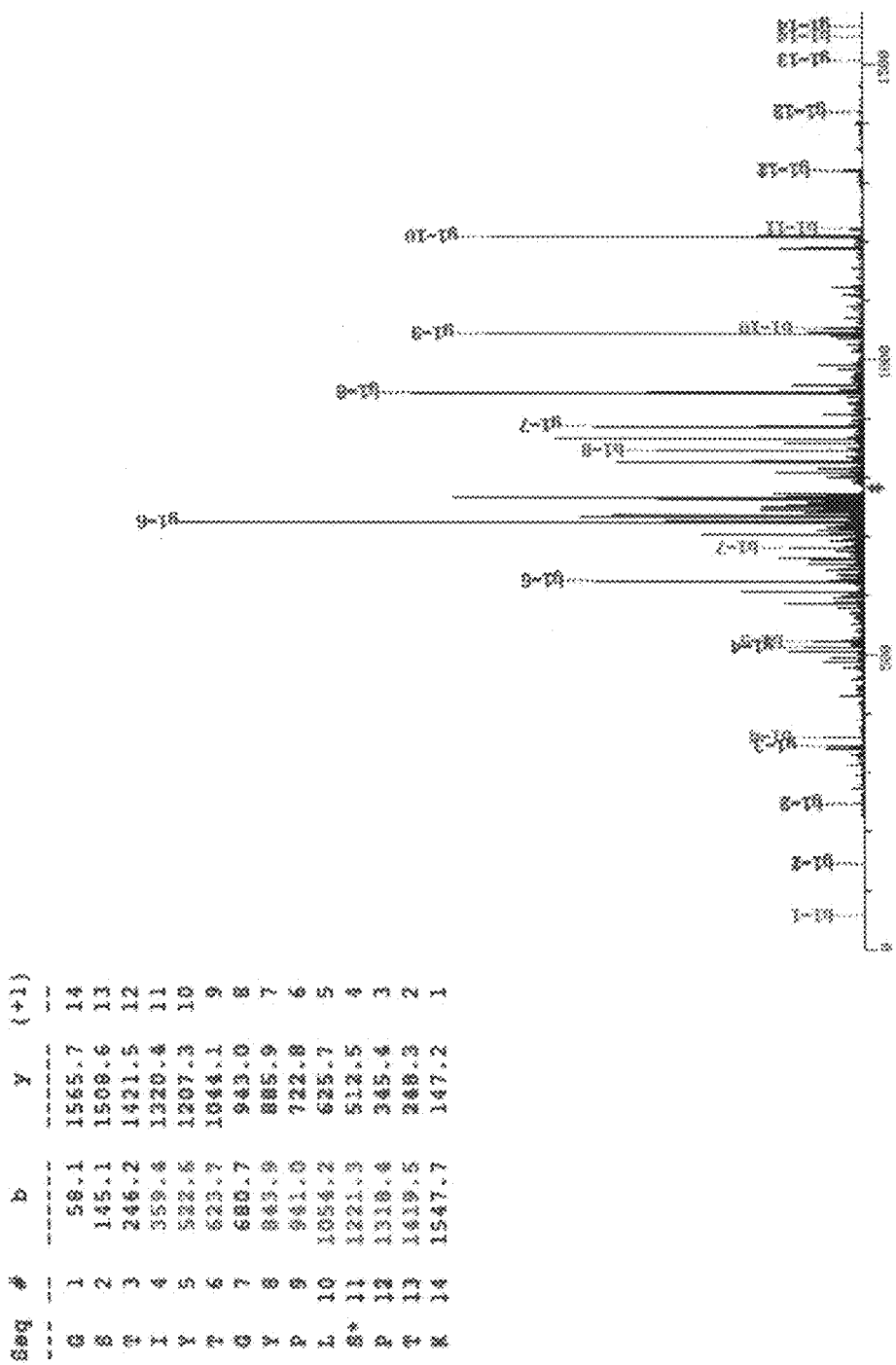
FIG. 5 is an exemplary mass spectrograph depicting the detection of the phosphorylation of serine 806 in HIPK1, as further described in Example 1 (red and blue indicate ions detected in MS/MS spectrum); S* (and pS) indicates the phosphorylated serine (corresponds to lowercase "s" in Column E of Table 1; SEQ ID NO: 54).
Figure 6:
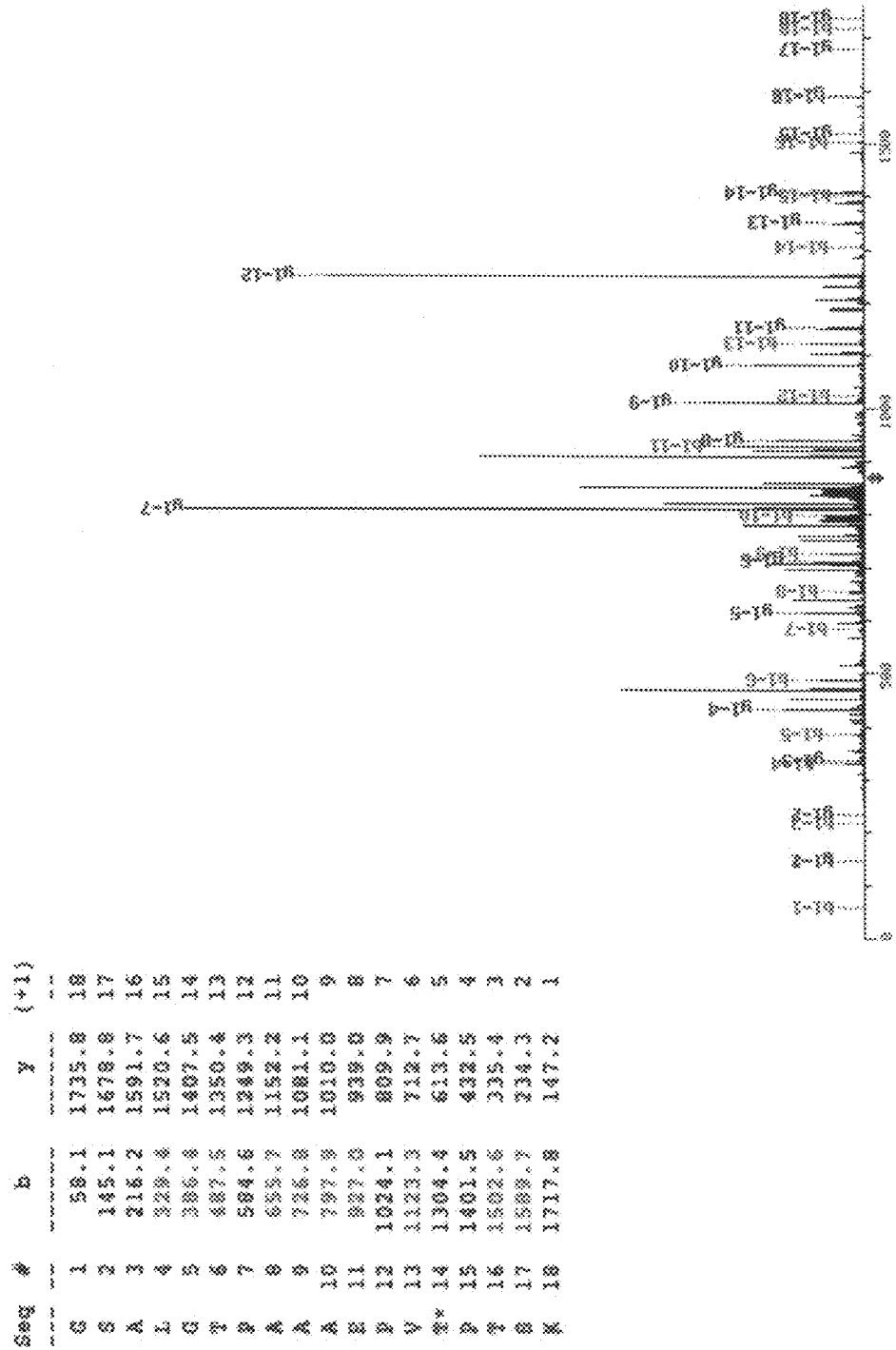
FIG. 6 is an exemplary mass spectrograph depicting the detection of the phosphorylation of threonine 852 in ABL1, as further described in Example 1 (red and blue indicate ions detected in MS/MS spectrum); T* (and pT) indicates the phosphorylated threonine (corresponds to lowercase "t" in Column E of Table 1; SEQ ID NO: 56).
Figure 7:
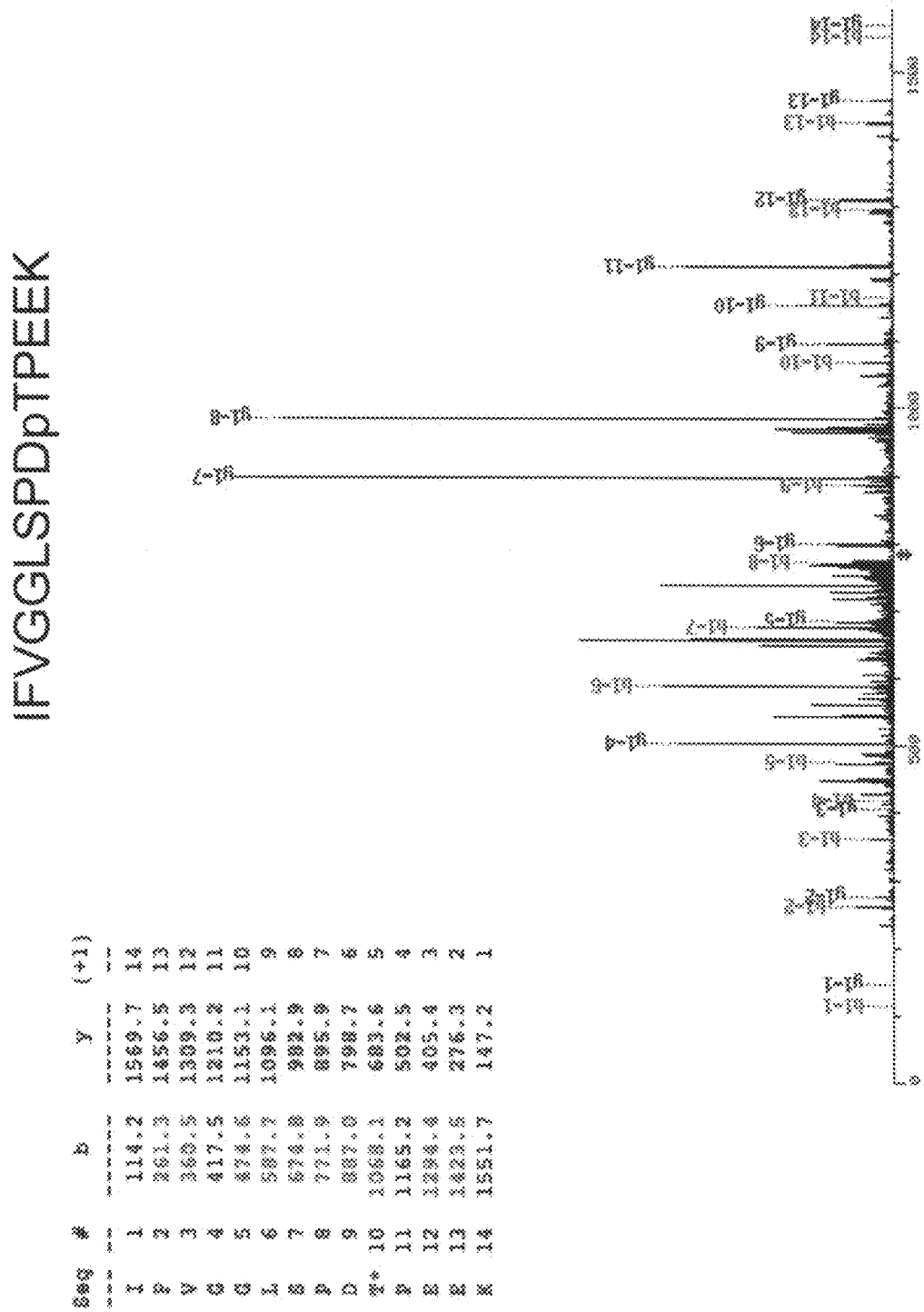
FIG. 7 is an exemplary mass spectrograph depicting the detection of the phosphorylation of threonine 193 in HNRPD, as further described in Example 1 (red and blue indicate ions detected in MS/MS spectrum); T* (and pT) indicates the phosphorylated threonine (corresponds to lowercase "t" in Column E of Table 1; SEQ ID NO: 68).
Figure 8:
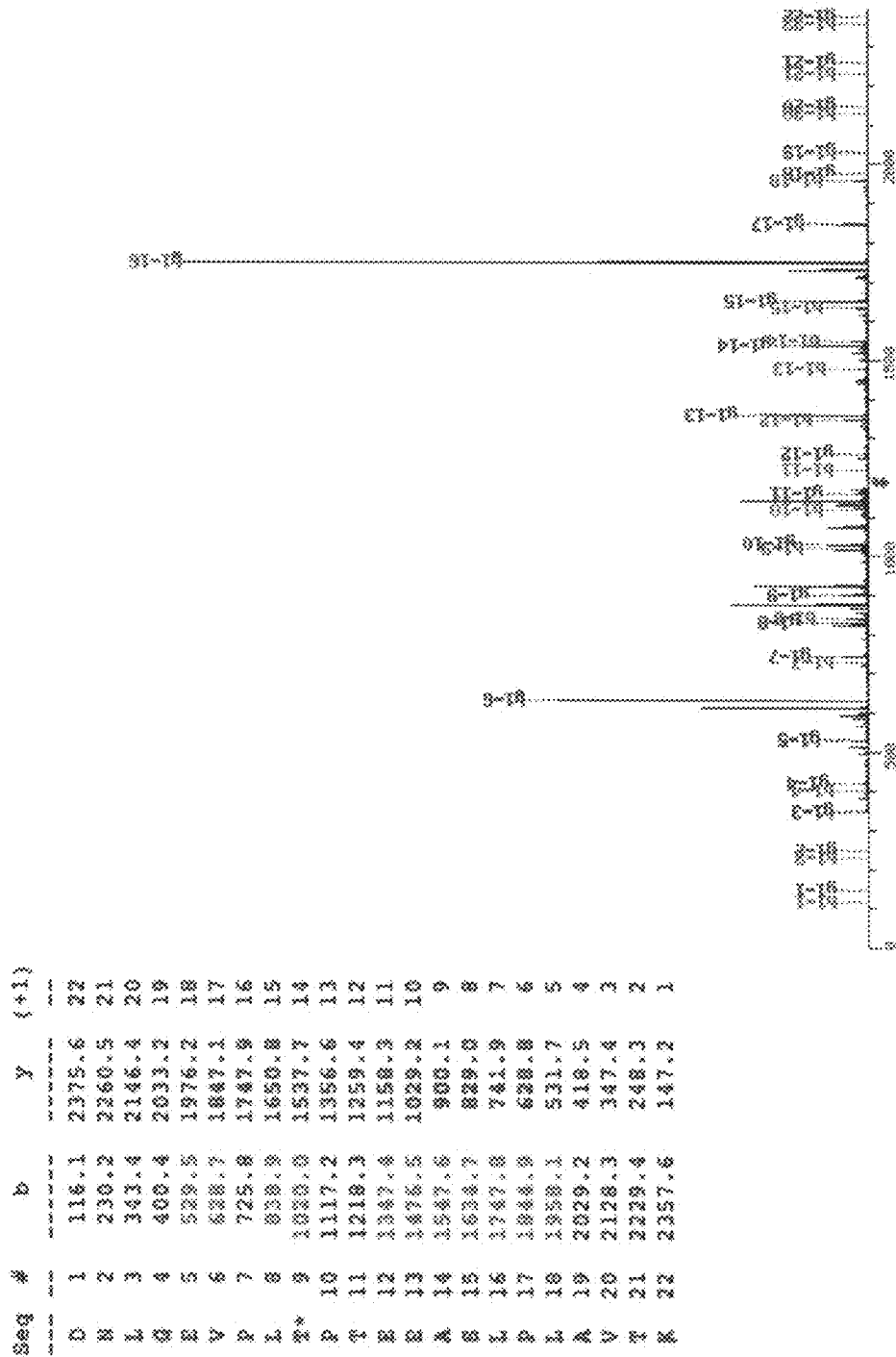
FIG. 8 is an exemplary mass spectrograph depicting the detection of the phosphorylation of threonine 1915 in NBEAL2, as further described in Example 1 (red and blue indicate ions detected in MS/MS spectrum); T* (and pT) indicates the phosphorylated threonine (corresponds to lowercase "t" in Column E of Table 1; SEQ ID NO: 138).

The novel phosphorylation sites of the invention were identified according to the methods described by Rush et al., U.S. Patent Publication No. 20030044848, which are herein incorporated by reference in its entirety. Briefly, phosphorylation sites were isolated and characterized by immunoaffinity isolation and mass-spectrometric characterization (IAP) (FIG. 1), using the following human carcinoma-derived cell lines and tissue samples: HeLa, Jurkat, K562, DMS 153, H69 (xenograft), HT29, M01043, H526, DMS 53, DMS 79, and MEC-1. In addition to the newly discovered phosphorylation sites (all having a phosphorylatable tyrosine, serine and/or threonine), many known phosphorylation sites were also identified.

The immunoaffinity/mass spectrometric technique described in Rush et al, i.e., the "IAP" method, is described in detail in the Examples and briefly summarized below.

The IAP method generally comprises the following steps: (a) a proteinaceous preparation (e.g., a digested cell extract) comprising phosphopeptides from two or more different proteins is obtained from an organism; (b) the preparation is contacted with at least one immobilized motif-specific, context-independent antibody; (c) at least one phosphopeptide specifically bound by the immobilized antibody in step (b) is isolated; and (d) the modified peptide isolated in step (c) is characterized by mass spectrometry (MS) and/or tandem mass spectrometry (MS-MS). Subsequently, (e) a search program (e.g., Sequest) may be utilized to substantially match the spectra obtained for the isolated, modified peptide during the characterization of step (d) with the spectra for a known peptide sequence. A quantification step, e.g., using SILAC or AQUA, may also be used to quantify isolated peptides in order to compare peptide levels in a sample to a baseline.

In the IAP method as disclosed herein, a general phosphotyrosine-specific antibody, a phospho-MAPK/CDK Substrate antibody (detecting PXsP motif) and phospho-MAPK substrate antibody (detecting PXtP motif). (commercially available from Cell Signaling Technology, Inc., Beverly, Mass., Catalogue #'s 9411, 2325 and 4391. respectively) may be used in the immunoaffinity step to isolate the widest possible number of phospho-tyrosine, phospho-serine and/or phospho-threonine containing peptides from the cell extracts.

As described in more detail in the Examples, lysates may be prepared from various carcinoma cell lines or tissue samples and digested with trypsin after treatment with DTT and iodoacetamide to alkylate cysteine residues. Before the immunoaffinity step, peptides may be pre-fractionated (e.g., by reversed-phase solid phase extraction using Sep-Pak $C_{18}$ columns) to separate peptides from other cellular components. The solid phase extraction cartridges may then be eluted (e.g., with acetonitrile). Each lyophilized peptide fraction can be redissolved and treated with a general phosphotyrosine-specific antibody, a phospho-MAPK/CDK Substrate antibody (detecting PXsP motif) and phospho-MAPK substrate antibody (detecting PXtP motif). (commercially available from Cell Signaling Technology, Inc., Beverly, Mass., Catalogue #'s 9411, 2325 and 4391. respectively) immobilized on protein Agarose. Immunoaffinity-purified peptides can be eluted and a portion of this fraction may be concentrated (e.g., with Stage or Zip tips) and analyzed by LC-MS/MS (e.g., using a ThermoFinnigan LCQ Deca XP Plus ion trap mass spectrometer or LTQ). MS/MS spectra can be evaluated using, e.g., the program Sequest with the NCBI human protein database.

The novel phosphorylation sites identified are summarized in Table 1/FIGS. 2A-2M. Column A lists the parent (signaling) protein in which the phosphorylation site occurs. Column D identifies the tyrosine, serine and/or threonine residue at which phosphorylation occurs (each number refers to the amino acid residue position of the tyrosine, serine and/or threonine in the parent human protein, according to the published sequence retrieved by the SwissProt accession number). Column E shows flanking sequences of the identified tyrosine, serine and/or threonine residues (which are the sequences of trypsin-digested peptides). FIGS. 2A-2M also shows the particular type of cancer (see Column G) and cell line(s) (see Column F) in which a particular phosphorylation site was discovered.

TABLE 1

Novel Tyrosine, Serine and Threonine Phosphorylation Sites.

| | A<br>Protein<br>Name | B<br>Accession<br>No. | C<br>Protein Type | D<br>Phospho-<br>Residue | E<br>Phosphorylation Site Sequence | H<br>SEQ ID NO |
|---|---|---|---|---|---|---|
| 2 | AHNAK | NP_001611.1 | Adaptor/scaffold | T5798 | EFSGPSTPTGtLEFEGGEVSLEGGK | SEQ ID NO: 1 |
| 3 | PDE4DIP | NP_001002811.1 | Adaptor/scaffold | Y180 | VADSDyEAICKVPR | SEQ ID NO: 2 |
| 4 | RANBP9 | NP_005484.2 | Adaptor/scaffold | S477 | SQDSYPVsPRPFSSPSMSPSHGMNIHNLASGK | SEQ ID NO: 3 |
| 5 | RANBP9 | NP_005484.2 | Adaptor/scaffold | S487 | SQDSYPVSPRPFSSPSMsPSHGMNIHNLASGK | SEQ ID NO: 4 |
| 6 | RIMS1 | NP_055804.2 | Adaptor/scaffold | T1245 | TLCSMHHLVPGGSAPPSPLLtR | SEQ ID NO: 5 |
| 7 | SLA | NP_006739.1 | Adaptor/scaffold | Y273 | KSSFFSSPPyFED | SEQ ID NO: 6 |
| 8 | TANC1 | NP_203752.1 | Adaptor/scaffold | Y1827 | TVSHLyQESISK | SEQ ID NO: 7 |
| 9 | TFG | NP_006061.2 | Adaptor/scaffold | Y392 | NRPPFGQGyTQPGPGYR | SEQ ID NO: 8 |
| 10 | BYSL | NP_004044.3 | Adhesion or extracellular matrix protein | Y49 | GRGTGEAEEEyVGPR | SEQ ID NO: 9 |
| 11 | FLRT2 | NP_037363.1 | Adhesion or extracellular matrix protein | S403 | SYTPPTPTTsKLPTIPDWDGR | SEQ ID NO: 10 |
| 12 | MLLT4 | NP_005927.2 | Adhesion or extracellular matrix protein | Y1269 | SQEELREDKAyQLER | SEQ ID NO: 11 |
| 13 | SSX2IP | NP_054740.2 | Adhesion or extracellular matrix protein | S540 | SLPAsPSTSDFCQTR | SEQ ID NO: 12 |
| 14 | CIAPIN1 | NP_064709.2 | Apoptosis | Y290 | CASCPyLGMPAFKPGEK | SEQ ID NO: 13 |
| 15 | CNNM3 | NP_060093.3 | Cell cycle regulation | Y301 | GGGDPySDLSK | SEQ ID NO: 14 |
| 16 | MDC1 | CAI18195.1 | Cell cycle regulation | T548 | TPETVVPAAPELQPSTSTDQPVtPEPTSR | SEQ ID NO: 15 |
| 17 | ORC3L | NP_036513.2 | Cell cycle regulation | Y527 | TDLyHLQK | SEQ ID NO: 16 |
| 18 | APRIN | NP_055847.1 | Chromatin, DNA-binding, DNA repair or DNA | S1162 | METVSNASSSsNPSSPGR | SEQ ID NO: 17 |
| 19 | APRIN | NP_055847.1 | Chromatin, DNA-binding, DNA repair or DNA | S1159 | METVSNAsSSSNPSSPGR | SEQ ID NO: 18 |
| 20 | APRIN | NP_055847.1 | Chromatin, DNA-binding, DNA repair or DNA | S1160 | METVSNASsSSNPSSPGR | SEQ ID NO: 19 |
| 21 | HIVEP1 | NP_002105.1 | Chromatin, DNA-binding, DNA repair or DNA | S537 | SSFTPSsPENVIGDFLLQDR | SEQ ID NO: 20 |
| 22 | TMPO | NP_001027454.1 | Chromatin, DNA-binding, DNA repair or DNA | Y223 | RVEHNQSySQAGITETEWTSGSSK | SEQ ID NO: 21 |
| 23 | TOX | NP_055544.1 | Chromatin, DNA-binding, DNA repair or DNA | Y511 | SGCRNPPPQPVDWNNDyCSSGGMQR | SEQ ID NO: 22 |
| 24 | ZC3HAV1 | NP_064504.2 | Chromatin, DNA-binding, DNA repair or DNA | Y690 | RPTFVPQWyVQQMK | SEQ ID NO: 23 |

TABLE 1-continued

Novel Tyrosine, Serine and Threonine Phosphorylation Sites.

| | A Protein Name | B Accession No. | C Protein Type | D Phospho-Residue | E Phosphorylation Site Sequence | H SEQ ID NO |
|---|---|---|---|---|---|---|
| 25 | ABLIM1 | NP_006711.3 | Cytoskeletal protein | Y199 | SPQHFHRPDQGINIyR | SEQ ID NO: 24 |
| 26 | MAP1A | NP_002364.5 | Cytoskeletal protein | T1834 | NEPtTPSWLADIPPWVPK | SEQ ID NO: 25 |
| 27 | NDE1 | NP_060138.1 | Cytoskeletal protein | T246 | GLDDSTGGTPLtPAAR | SEQ ID NO: 26 |
| 28 | KIF1C | NP_006603.2 | Endoplasmic reticulum or golgi | S1026 | RPPSPRRsHHPR | SEQ ID NO: 27 |
| 29 | KIF1C | NP_006603.2 | Endoplasmic reticulum or golgi | S1022 | RPPsPRRSHHPR | SEQ ID NO: 28 |
| 30 | B4GALNT4 | NP_848632.2 | Enzyme, misc. | S491 | SGPQSPAPAAPAQPGATLAPPTPPRPRDGGTPRHsR | SEQ ID NO: 29 |
| 31 | B4GALNT4 | NP_848632.2 | Enzyme, misc. | T478 | SGPQSPAPAAPAQPGATLAPPtPPRPRDGGTPRHSR | SEQ ID NO: 30 |
| 32 | B4GALNT4 | NP_848632.2 | Enzyme, misc. | S461 | SGPQsPAPAAPAQPGATLAPPTPPRPRDGGTPRHSR | SEQ ID NO: 31 |
| 33 | DAGLBETA | NP_631918.1 | Enzyme, misc. | Y573 | WSPAySFSSDSPLDSSPK | SEQ ID NO: 32 |
| 34 | DOT1L | NP_115871.1 | Enzyme, misc. | S1009 | NSLPASPAHOLSSsPR | SEQ ID NO: 33 |
| 35 | EZH2 | NP_004447.2 | Enzyme, misc. | T372 | LPNNSSRPStPTINVLESK | SEQ ID NO: 34 |
| 36 | EZH2 | NP_004447.2 | Enzyme, misc. | S368 | LPNNSsRPSTPTINVLESK | SEQ ID NO: 35 |
| 37 | IARS | NP_002152.2 | Enzyme, misc. | S1047 | APLKPYPVsPSDKVLIQEK | SEQ ID NO: 36 |
| 38 | JMJD1B | NP_057688.2 | Enzyme, misc. | T1307 | DLLHSGPGKLPQtPLDTGIPFPPVFSTSSAGVK | SEQ ID NO: 37 |
| 39 | PPIL4 | NP_024311.1 | Enzyme, misc. | Y466 | YQTDLyERER | SEQ ID NO: 38 |
| 40 | ARHGEF11 | NP_055599.1 | G protein or regulator | T668 | SLENPtPPFTPK | SEQ ID NO: 39 |
| 41 | ARHGEF11 | NP_055599.1 | G protein or regulator | T672 | SLENPTPPFtPK | SEQ ID NO: 40 |
| 42 | DOCK7 | NP_212132.2 | G protein or regulator | Y169 | QVFESDEAPDGNSyQDDQDDLKRR | SEQ ID NO: 41 |
| 43 | RAB3IL1 | NP_037533.2 | G protein or regulator | S179 | TLVITSTPASPNRELHPQLLsPTK | SEQ ID NO: 42 |
| 44 | RAB3IL1 | NP_037533.2 | G protein or regulator | S168 | TLVITSTPAsPNR | SEQ ID NO: 43 |
| 45 | RAPGEF6 | NP_057424.2 | G protein or regulator | Y1490 | GLIVyCVTSPK | SEQ ID NO: 44 |
| 46 | SIPA1L1 | NP_056371.1 | G protein or regulator | S161 | FLMPEAYPsSPR | SEQ ID NO: 45 |
| 47 | INPP4A | NP_004018.1 | Phosphatase | Y933 | HYRPPEGTYGKVET | SEQ ID NO: 46 |
| 48 | HGFAC | NP_001519.1 | Protease | S388 | VQLSPDLLATLPEPAsPGR | SEQ ID NO: 47 |
| 49 | HGFAC | NP_001519.1 | Protease | S376 | VQLsPDLLATLPEPASPGR | SEQ ID NO: 48 |
| 50 | MAP2K1 | NP_002746.1 | Protein kinase, dual-specificity | T388 | RSDAEEVDFAGWLCSTIGLNQPSTPtHAAGV | SEQ ID NO: 49 |
| 51 | CDK10 | NP_003665.2 | Protein kinase, Ser/Thr (non-receptor) | T167 | AYGVPVKPMtPK | SEQ ID NO: 50 |

TABLE 1-continued

Novel Tyrosine, Serine and Threonine Phosphorylation Sites.

| | A<br>Protein<br>Name | B<br>Accession<br>No. | C<br>Protein Type | D<br>Phospho-<br>Residue | E<br>Phosphorylation Site Sequence | H<br>SEQ ID NO |
|---|---|---|---|---|---|---|
| 52 | DCAMKL1 | NP_004725.1 | Protein kinase, Ser/Thr (non-receptor) | S334 | SPSPsPTSPGSLRK | SEQ ID NO: 51 |
| 53 | DCAMKL1 | NP_004725.1 | Protein kinase, Ser/Thr (non-receptor) | S337 | SPSPSPTsPGSLRK | SEQ ID NO: 52 |
| 54 | DCAMKL1 | NP_004725.1 | Protein kinase, Ser/Thr (non-receptor) | S340 | SPSPSPTSPGsLRK | SEQ ID NO: 53 |
| 55 | HIPK1 | NP_852003.1 | Protein kinase, Ser/Thr (non-receptor) | S806 | GSTIYTGYPLsPTK | SEQ ID NO: 54 |
| 56 | KIAA2002 | XP_370878.2 | Protein kinase, Ser/Thr (non-receptor) | Y463 | GLDIESyDSLERPLRK | SEQ ID NO: 55 |
| 57 | ABL1 | NP_005148.2 | Protein kinase, Tyr (non-receptor) | T852 | GSALGTPAAAEPVtPTSK | SEQ ID NO: 56 |
| 58 | ZAP70 | NP_001070.2 | Protein kinase, Tyr (non-receptor) | Y87 | AHCGPAELCEFySRDPDGLPCNLR | SEQ ID NO: 57 |
| 59 | EPHA8 | NP_001006944.1 | Protein kinase, Tyr (receptor) | S444 | NsVPQRPGPPASPASDPSR | SEQ ID NO: 58 |
| 60 | EPHA8 | NP_001006944.1 | Protein kinase, Tyr (receptor) | S454 | NSVPQRPGPPAsPASDPSR | SEQ ID NO: 59 |
| 61 | EPHA8 | NP_001006944.1 | Protein kinase, Tyr (receptor) | S460 | NSVPQRPGPPASPASDPsR | SEQ ID NO: 60 |
| 62 | ABCE1 | NP_002931.2 | Receptor, channel, transporter or cell su | Y594 | KSGNyFFLDD | SEQ ID NO: 61 |
| 63 | ABCF3 | NP_060828.1 | Receptor, channel, transporter or cell su | Y100 | ITENyDCGTKLPGLLKR | SEQ ID NO: 62 |
| 64 | CACNA1A | NP_075461.1 | Receptor, channel, transporter or cell su | T2290 | RQLPQtPSTPRPHVSYSPVIR | SEQ ID NO: 63 |
| 65 | CACNA1A | NP_075461.1 | Receptor, channel, transporter or cell su | S2299 | RQLPQTPSTPRPHVsYSPVIR | SEQ ID NO: 64 |
| 66 | IGSF6 | NP_005840.2 | Receptor, channel, transporter or cell su | S54 | CTFsATGCPSEQPTCLWFR | SEQ ID NO: 65 |
| 67 | IGSF6 | NP_005840.2 | Receptor, channel, transporter or cell su | T56 | CTFSAtGCPSEQPTCLWFR | SEQ ID NO: 66 |
| 68 | IGSF6 | NP_005840.2 | Receptor, channel, transporter or cell su | T64 | CTFSATGCPSEQPtCLWFR | SEQ ID NO: 67 |

TABLE 1-continued

Novel Tyrosine, Serine and Threonine Phosphorylation Sites.

| | A<br>Protein<br>Name | B<br>Accession<br>No. | C<br>Protein Type | D<br>Phospho-<br>Residue | E<br>Phosphorylation Site Sequence | H<br>SEQ ID NO |
|---|---|---|---|---|---|---|
| 69 | HNRPD | NP_002129.2 | RNA binding protein | T193 | IFVGGLSPDtPEEK | SEQ ID NO: 68 |
| 70 | HNRPH2 | NP_062543.1 | RNA binding protein | S104 | HTGPNsPDTANDGFVR | SEQ ID NO: 69 |
| 71 | PCBP1 | NP_006187.1 | RNA binding protein | Y183 | VMTIPyQPMPASSPVICAGGQDR | SEQ ID NO: 70 |
| 72 | SRRM2 | NP_057417.2 | RNA binding protein | T2289 | TAVAPSAVNLADPRtPTAPAVNLAGAR | SEQ ID NO: 71 |
| 73 | SRRM2 | NP_057417.2 | RNA binding protein | Y1049 | SSTPPGESyFGVSSLQLK | SEQ ID NO: 72 |
| 74 | TARBP2 | NP_004169.3 | RNA binding protein | S131 | SPPMELQPPVsPQQSECNPVGALQELVVQK | SEQ ID NO: 73 |
| 75 | ATF7 | NP_006847.1 | Transcriptional regulator | S97 | AAAGPLDMsLPSTPDIK | SEQ ID NO: 74 |
| 76 | ATF7 | NP_006847.1 | Transcriptional regulator | T101 | AAAGPLDMSLPStPDIK | SEQ ID NO: 75 |
| 77 | CHD8 | NP_065971.1 | Transcriptional regulator | S2240 | APGYPSsPVTTASGTTLR | SEQ ID NO: 76 |
| 78 | DMAP1 | NP_061973.1 | Transcriptional regulator | T409 | AGVLGGPAtPASGPGPASAEPAVTEPGLGPDPK | SEQ ID NO: 77 |
| 79 | DMAP1 | NP_061973.1 | Transcriptional regulator | S412 | AGVLGGPATPAsGPGPASAEPAVTEPGLGPDPK | SEQ ID NO: 78 |
| 80 | ECD | NP_009196.1 | Transcriptional regulator | Y448 | ESESVSKEEKEQNyDLTEVSESMK | SEQ ID NO: 79 |
| 81 | GTF3C5 | NP_036219.1 | Transcriptional regulator | Y194 | EGyNNPPISGENLIGLSR | SEQ ID NO: 80 |
| 82 | HEXIM2 | NP_653209.1 | Transcriptional regulator | T32 | TSGAPGSPQtPPERHDSGGSLPLTPR | SEQ ID NO: 81 |
| 83 | HEXIM2 | NP_653209.1 | Transcriptional regulator | T46 | TSGAPGSPQTPPERHDSGGSLPLtPR | SEQ ID NO: 82 |
| 84 | MLL2 | NP_003473.1 | Transcriptional regulator | S4547 | IPNSYEVLFPEsPAR | SEQ ID NO: 83 |
| 85 | PPP1R13L | NP_006654.2 | Transcriptional regulator | Y126 | TPLyLQPDAYGSLDR | SEQ ID NO: 84 |
| 86 | RB1 | NP_000312.2 | Transcriptional regulator | S794 | SPYKFPsSPLR | SEQ ID NO: 85 |
| 87 | SIAHBP1 | NP_055096.2 | Transcriptional regulator | T60 | LGLPPLtPEQQEALQK | SEQ ID NO: 86 |
| 88 | SUPT5H | NP_003160.2 | Transcriptional regulator | T1034 | VVSISSEHLEPItPTKNNK | SEQ ID NO: 87 |
| 89 | SUPT5H | NP_003160.2 | Transcriptional regulator | T1036 | VVSISSEHLEPITPtKNNK | SEQ ID NO: 88 |
| 90 | YBX1 | NP_004550.2 | Transcriptional regulator | Y238 | RPQYSNPPVQGEVMEGADNQGAGEQGRPVRQNMyR | SEQ ID NO: 89 |
| 91 | ZNFN1A1 | NP_006051.1 | Transcriptional regulator | Y413 | SGLIyLTNHIAPHAR | SEQ ID NO: 90 |
| 92 | EEF1G | NP_001395.1 | Translational regulator | S387 | GQELAFPLsPDWQVDYESYTWR | SEQ ID NO: 91 |

TABLE 1-continued

Novel Tyrosine, Serine and Threonine Phosphorylation Sites.

| | A Protein Name | B Accession No. | C Protein Type | D Phospho-Residue | E Phosphorylation Site Sequence | H SEQ ID NO |
|---|---|---|---|---|---|---|
| 93 | CCDC86 | NP_077003.1 | Ubiquitin conjugating system | S21 | RLGGLRPESPEsLTSVSR | SEQ ID NO: 92 |
| 94 | UFD1L | NP_005650.2 | Ubiquitin conjugating system | Y219 | QVQHEESTEGEADHSGyAGELGFR | SEQ ID NO: 93 |
| 95 | USP11 | NP_004642.2 | Ubiquitin conjugating system | S948 | RLLSPAGSSGAPAsPACSSPPSSEFMDVN | SEQ ID NO: 94 |
| 96 | USP11 | NP_004642.2 | Ubiquitin conjugating system | S938 | RLLsPAGSSGAPASPACSSPPSSEFMDVN | SEQ ID NO: 95 |
| 97 | USP15 | AAD41086.1 | Ubiquitin conjugating system | S229 | GPSTPKsPGASNFSTLPK | SEQ ID NO: 96 |
| 98 | ANKRD50 | NP_065070.1 | Unknown function | Y1299 | VLEyEMTQFDRR | SEQ ID NO: 97 |
| 99 | ASXL2 | NP_060733.3 | Unknown function | T27 | YPNtPMSHK | SEQ ID NO: 98 |
| 100 | ATXN2L | NP_009176.2 | Unknown function | S684 | STSTPTsPGPR | SEQ ID NO: 99 |
| 101 | ATXN2L | NP_009176.2 | Unknown function | T683 | STSTPtSPGPR | SEQ ID NO: 100 |
| 102 | BCORL1 | BAC85922.1 | Unknown function | T161 | SPTPVKPTEPCtPSK | SEQ ID NO: 101 |
| 103 | C11orf2 | NP_037397.2 | Unknown function | Y651 | TFSVySSSR | SEQ ID NO: 102 |
| 104 | C13orf8 | NP_115812.1 | Unknown function | S389 | SSSVSPSSWKSPPASPEsWK | SEQ ID NO: 103 |
| 105 | C13orf8 | NP_115812.1 | Unknown function | S376 | SSSVsPSSWKSPPASPESWK | SEQ ID NO: 104 |
| 106 | C20orf114 | NP_149974.2 | Unknown function | S483 | DALVLTPASLWKPSSPVsQ | SEQ ID NO: 105 |
| 107 | C20orf114 | NP_149974.2 | Unknown function | S474 | DALVLTPAsLWKPSSPVSQ | SEQ ID NO: 106 |
| 108 | C20orf114 | NP_149974.2 | Unknown function | S479 | DALVLTPASLWKPsSPVSQ | SEQ ID NO: 107 |
| 109 | C6orf194 | NP_001007532.1 | Unknown function | S23 | RSsSGSPPSPQSR | SEQ ID NO: 108 |
| 110 | C6orf194 | NP_001007532.1 | Unknown function | S24 | RSSsGSPPSPQSR | SEQ ID NO: 109 |
| 111 | C6orf194 | NP_001007532.1 | Unknown function | S26 | RSSSGsPPSPOSR | SEQ ID NO: 110 |
| 112 | C9orf30 | NP_542386.1 | Unknown function | S274 | EWPVSSFNRPFPNsP | SEQ ID NO: 111 |
| 113 | DNAJA5 | NP_919259.3 | Unknown function | Y81 | GGFDGEyQDDSLDLLR | SEQ ID NO: 112 |
| 114 | FAM120A | NP_055427.2 | Unknown function | Y431 | HTPLyER | SEQ ID NO: 113 |
| 115 | FAM122A | NP_612206.3 | Unknown function | S76 | HGLLLPAsPVR | SEQ ID NO: 114 |
| 116 | FAM122B | NP_660327.2 | Unknown function | S115 | RIDFTPVsPAPSPTR | SEQ ID NO: 115 |
| 117 | FAM122B | NP_660327.2 | Unknown function | S119 | RIDFTPVSPAPsPTR | SEQ ID NO: 116 |
| 118 | FAM122B | NP_660327.2 | Unknown function | S137 | MFVSSSGLPPsPVPSPR | SEQ ID NO: 117 |
| 119 | FAM122B | NP_660327.2 | Unknown function | S141 | MFVSSSGLPPSPVPsPR | SEQ ID NO: 118 |
| 120 | FBXL20 | NP_116264.2 | Unknown function | T417 | VHAYFAPVtPPPSVGGSR | SEQ ID NO: 119 |
| 121 | FLJ14640 | NP_116205.3 | Unknown function | Y157 | GGHSDDLyAVPHR | SEQ ID NO: 120 |
| 122 | KIAA0692 | XP_931084.1 | Unknown function | Y256 | GICDyFPSPSK | SEQ ID NO: 121 |

TABLE 1-continued

Novel Tyrosine, Serine and Threonine Phosphorylation Sites.

| | A Protein Name | B Accession No. | C Protein Type | D Phospho-Residue | E Phosphorylation Site Sequence | H SEQ ID NO |
|---|---|---|---|---|---|---|
| 123 | KIAA1012 | NP_055754.2 | Unknown function | S971 | RPEFFTFGGNTAVLTPLsPSASENCSAYK | SEQ ID NO: 122 |
| 124 | KIAA1458 | XP_044434.3 | Unknown function | S247 | SSDRNPPLsPQSSIDSELSASELDEDSIGSNYK | SEQ ID NO: 123 |
| 125 | KIDINS220 | NP_065789.1 | Unknown function | S1555 | VPKsPEHSAEPIR | SEQ ID NO: 124 |
| 126 | LEREPO4 | NP_060941.1 | Unknown function | Y358 | FSTyTSDKDENKLSEASGGR | SEQ ID NO: 125 |
| 127 | LMO7 | NP_005349.3 | Unknown function | Y348 | SWASPVyTEADGTFSR | SEQ ID NO: 126 |
| 128 | LOC149950 | NP_001010976.1 | Unknown function | S109 | QIPPPQTPsTDPQTLPLSFRSLLR | SEQ ID NO: 127 |
| 129 | LOC149950 | NP_001010976.1 | Unknown function | S121 | QIPPPQTPSTDPQTLPLSFRsLLR | SEQ ID NO: 128 |
| 130 | LOC149950 | NP_001010976.1 | Unknown function | T114 | QIPPPQTPSTDPtHLPLSFRSLLR | SEQ ID NO: 129 |
| 131 | LOC196752 | NP_001010864.1 | Unknown function | S48 | KQsAGPNSPTGGGGGGSGGTRMR | SEQ ID NO: 130 |
| 132 | LOC51255 | NP_057578.1 | Unknown function | Y152 | LENLHGAMyT | SEQ ID NO: 131 |
| 133 | LOXHD1 | NP_653213.4 | Unknown function | S1523 | CLDPHSSFQPPPTPSPGSSGLsMDLVK | SEQ ID NO: 132 |
| 134 | LOXHD1 | NP_653213.4 | Unknown function | S1519 | CLDPHSSFQPPPTPSPGsSGLSMDLVK | SEQ ID NO: 133 |
| 135 | LTV1 | NP_116249.2 | Unknown function | Y243 | FTEySMTSSVMR | SEQ ID NO: 134 |
| 136 | MAGEC1 | AAC18837.1 | Unknown function | S266 | TQSTFEGFPQsPLQIPVSR | SEQ ID NO: 135 |
| 137 | MGC22793 | NP_659467.1 | Unknown function | S87 | LTPPsPVRSEPQPAVPQELEMPVLK | SEQ ID NO: 136 |
| 138 | N4BP1 | NP_694574.3 | Unknown function | Y415 | NKGVySSTNELTTDSTPK | SEQ ID NO: 137 |
| 139 | NBEAL2 | XP_291064.5 | Unknown function | T1915 | DNLGEVPLtPTEEASLPLAVTK | SEQ ID NO: 138 |
| 140 | NIBP | NP_113654.3 | Unknown function | S1051 | MAIQVDKFNFESFPEsPGEKGQFANPK | SEQ ID NO: 139 |
| 141 | PHACTR4 | NP_076412.2 | Unknown function | T416 | IQQALTSPLPMtPILEGSHR | SEQ ID NO: 140 |
| 142 | RCSD1 | NP_443094.2 | Unknown function | S116 | AMVsPFHSPPSTPSSPGVR | SEQ ID NO: 141 |
| 143 | RCSD1 | NP_443094.2 | Unknown function | S120 | AMVSPFHsPPSTPSSPGVR | SEQ ID NO: 142 |
| 144 | RCSD1 | NP_443094.2 | Unknown function | S127 | AMVSPFHSPPSTPSsPGVR | SEQ ID NO: 143 |
| 145 | RNF168 | NP_689830.2 | Unknown function | Y104 | ASGQESEEVADDyQPVR | SEQ ID NO: 144 |
| 146 | SVH | NP_114111.2 | Unknown function | Y89 | TSQPEDLTDGSyDDVLNAEQLQK | SEQ ID NO: 145 |
| 147 | TBC1D16 | NP_061893.2 | Unknown function | T758 | KGPKtPQDGFGFRR | SEQ ID NO: 146 |
| 148 | THADA | NP_071348.3 | Unknown function | Y1003 | DTNDyFNQAK | SEQ ID NO: 147 |
| 149 | TNRC15 | NP_056390.2 | Unknown function | Y1299 | LNMGEIETLDDy | SEQ ID NO: 148 |
| 150 | VPS13D | NP_056193.2 | Unknown function | S1765 | EVQDKDYPLTPPPsPTVDEPK | SEQ ID NO: 149 |
| 151 | VPS13D | NP_056193.2 | Unknown function | T1761 | EVQDKDYPLtPPPSPTVDEPK | SEQ ID NO: 150 |
| 152 | ZCCHC11 | NP_056084.1 | Unknown function | S104 | FPNsPVKAEK | SEQ ID NO: 151 |
| 153 | ZNF609 | NP_055857.1 | Unknown function | T823 | LENTTPTQPLtPLHVVTQNGAEASSVK | SEQ ID NO: 152 |
| 154 | ZNF687 | NP_065883.1 | Unknown function | S140 | MQNGFGSPEPSLPGTPHsPAPPSGGTWK | SEQ ID NO: 153 |
| 155 | GOLGB1 | NP_004478.1 | Vesicle protein | Y3025 | QASPETSASPDGSQNLVyETELLR | SEQ ID NO: 154 |
| 156 | NISCH | NP_009115.2 | Vesicle protein | Y1307 | MENyELIHSSR | SEQ ID NO: 155 |

One of skill in the art will appreciate that, in many instances the utility of the instant invention is best understood in conjunction with an appreciation of the many biological roles and significance of the various target signaling proteins/polypeptides of the invention. The foregoing is illustrated in the following paragraphs summarizing the knowledge in the art relevant to a few non-limiting representative peptides containing selected phosphorylation sites according to the invention.

HIPK1 (homeodomain interacting protein kinase 1), phosphorylated at S806, is among the proteins listed in this patent. HIPK1 is a ubiquitous serine/threonine protein kinase that localizes predominantly to the nucleus where it plays a role as a corepressor for homeodomain transcription factors. HIPK1 is critical for activation of the (ASK1)-p38 signaling pathway, which is pivotal in regulating cell apoptosis. TNFalpha induces the translocation of HIPK1 from nucleus to cytoplasm, where it activates the pro-apoptotic ASK1-JNK/P38 pathway (J Biol. Chem. 2005 280:15061-70). HIPK1 modulates the localization, phosphorylation, and transcriptional activity of Daxx, a transcriptional co-regulatory protein that mediates apoptosis by activating the JNK pathway (Mol Cell Biol. 2003 23:950-60). HIPK1 may play a role in oncogenesis. It binds and phosphorylates the tumor-suppressor protein p53, and is highly expressed in human breast cancer cell lines and oncogenically transformed mouse embryonic fibroblasts. The HIPK1 gene is localized to human chromosome band 1p13, a site frequently altered in cancers. HIPK1−/− mouse embryonic fibroblasts exhibited reduced transcription of Mdm2 and were more susceptible than transformed HIPK1+/+cells to apoptosis induced by DNA damage. Carcinogen-treated HIPK1−/−mice developed fewer and smaller skin tumors than HIPK1+/+mice. HIPK1 appears to play a role in tumorigenesis, perhaps by means of the regulation of p53 and/or Mdm2 (Proc Natl Acad Sci U S A. 2003; 100: 5431-6).

TMPO (thymopoietin; also known as lamina-associated polypeptide 2, or LAP2), phosphorylated at Y223, is among the proteins listed in this patent. TMPO is a single-pass type II membrane protein that tightly associates with the nuclear lamina, binds DNA, and is involved in chromatin remodeling, and the initiation of replication and repression of transcription. It helps direct the assembly of the nuclear lamina and thereby helps maintain the structural organization of the nuclear envelope. TMPO is an anchor for the attachment of lamin filaments to the inner nuclear membrane and is involved in the control of initiation of DNA replication through its interaction with HAP95. TMPO transcription is under direct control of E2F transcription factors. It is highly expressed in rapidly replicating cells of various hematological malignancies but not in slowly proliferating cells. TMPO binds HDAC3 and this complex may play a role in hematological malignancies. The LAP2-HDAC regulatory pathway represents a possible target for rational therapy (Ann Hematol. 2007 86:393-401). TMPO is overexpressed in a significant percentage of primary larynx, lung, stomach, breast, and colon cancer tissues. Its over-expression in primary tumors was found to be correlated with tumor proliferation rate (Cell Cycle. 2006 5:1331-41). TMPO is associated with dilated cardiomyopathy and upregulated in medulloblastoma. This protein has potential diagnostic and/or therapeutic implications based on association with various hematological malignancies, cancer of the larynx, lung, stomach, breast, and colon, and other neoplasms (Biol Chem 1999 380:653-60). (PhosphoSite®, Cell Signaling Technology (Danvers, Mass.), Human PSD™, Biobase Corporation, (Beverly, Mass.)).

ZAP70, phosphorylated at Y87, is among the proteins listed in this patent. ZAP70, a tyrosine kinase of the Syk family, translocates from the cytosol to the T-cell antigen receptor zeta-chain following TCR stimulation. Plays a critical role in antigen-receptor signaling, activation, and development. Phosphorylated by Src-family kinases following antigen receptor activation. Mutations cause selective T cell defects in man, a recessive form of severe combined immunodeficiency (SCID) exhibiting selective absence of CD8+ T cells. Reduced expression predicts positive outcome in B cell chronic lymphocytic leukemia. A mutation in the SKG mouse produces increased numbers of self-reactive T cells and chronic arthritis. This protein has diagnostic and/or therapeutic applications for chronic lymphocytic leukemias (Clin Chem. 2007 Aug. 16; [Epub ahead of print], Blood 2002 100:4609-14). (PhosphoSite®, Cell Signaling Technology (Danvers, Mass.), Human PSD™, Biobase Corporation, (Beverly, Mass.)).

EPHA8, phosphorylated at S444 S460 and S454, is among the proteins listed in this patent. EPHA8, a receptor tyrosine kinase of the Eph family, is a receptor for members of the ephrin-A family of surface proteins: ephrin A2, A3 and A5. It plays a role in short-range contact-mediated axonal guidance during development of the mammalian nervous system. The Eph receptor tyrosine kinases bind membrane-anchored ligands, ephrins, at sites of cell-cell contact, regulating the repulsion and adhesion of cells that underlie the establishment, maintenance, and remodeling of patterns of cellular organization. Eph signals are particularly important in regulating cell adhesion and cell migration during development, axon guidance, homeostasis and disease. Eph receptors and ephrins also regulate the adhesion of endothelial cells and are required for the remodeling of blood vessels, implying a function in angiogenesis. Mutation may correlate with colorectal cancer. This protein has potential diagnostic and/or therapeutic implications for colorectal neoplasms (Science 2003 300:949).

EZH2, phosphorylated at S368 and T372, is among the proteins listed in this patent. EZH2 (enhancer of zeste homolog 2), a repressor of gene transcription, has been linked to the progression of various malignancies. It is a member of the polycomb family of transcription factors and controls methylation of various EZH2 target promoters. EZH2 protein levels increase incrementally from benign nevi to melanoma, which suggests that EZH2 may play a role in the pathogenesis and progression of melanoma. (J Cutan Pathol. 2007 34:597-600). EZH2 has been linked to the progression of various malignancies. Its expression levels increased in parallel with urothelial carcinoma (UC) tumor stage. High grade UC displayed significantly elevated EZH2 levels compared to low grade disease (J Cancer Res Clin Oncol. 2007 Aug. 11; [Epub ahead of print]). EZH2 expression and APAF-1 methylation are related to tumor progression and invasiveness. APAF-1 methylation is related to transcriptional activity of EZH2 expression in early-stage tumor disease of the bladder (Tumour Biol. 28:151-7). This protein has potential diagnostic and/or therapeutic implications for melanoma, urothelial carcinoma, bladder cancer, and non-Hodgkin lymphoma (Blood 2001 97:3896-901). (PhosphoSite®, Cell Signaling Technology (Danvers, Mass.), Human PSD™, Biobase Corporation, (Beverly, Mass.)).

RIMS1, phosphorylated at T1245, is among the proteins listed in this patent. RIMS1, Regulating synaptic membrane exocytosis 1 (Rab3 interacting protein 1), a putative RAB3 interacting protein, may play a role in neurotransmitter secretion; mutations in the gene are associated with autosomal dominant cone-rod dystrophy. (PhosphoSite®, Cell Signaling Technology (Danvers, Mass.), Human PSD™, Biobase Corporation, (Beverly, Mass.)).

TFG, phosphorylated at Y392, is among the proteins listed in this patent. TFG, TRK-fused gene, binds and negatively regulates SHP-1 (PTPN6); gene fusions with ALK and NTRK1 are associated with anaplastic large cell lymphoma and papillary thyroid carcinoma, respectively. This protein has potential diagnostic and/or therapeutic implications based on association with the following diseases: Large-Cell Lymphoma (Blood 1999 Nov. 1; 94(9):3265-8). (PhosphoSite®, Cell Signaling Technology (Danvers, Mass.), Human PSD™, Biobase Corporation, (Beverly, Mass.)).

MLLT4, phosphorylated at Y1269, is among the proteins listed in this patent. MLLT4, Mixed lineage-leukemia translocation to 4 homolog (afadin), intercellular junction protein, negatively regulates cell adhesion, may regulate actin polymerization; MLLT4-ALL-1 (MLL) fusion variant is associated with acute myeloid leukemia. This protein has potential diagnostic and/or therapeutic implications based on association with the following diseases: Myelocytic Leukemia, Monocytic Leukemia (Blood 1996 Mar. 15; 87(6):2496-505). (PhosphoSite®, Cell Signaling Technology (Danvers, Mass.), Human PSD™, Biobase Corporation, (Beverly, Mass.)).

ORC3L, phosphorylated at Y527, is among the proteins listed in this patent. ORC3L, Origin recognition complex 3-like homolog (S. cerevisiae), a nuclear protein which functions in DNA replication, putative component of the origin recognition complex. (PhosphoSite®, Cell Signaling Technology (Danvers, Mass.), Human PSD™, Biobase Corporation, (Beverly, Mass.)).

APRIN, phosphorylated at S1159, S1160 and S1162, is among the proteins listed in this patent. APRIN, Androgen-induced proliferation inhibitor, predicted to be a mediator of androgen-induced proliferative shutoff, may be associated with prostate cancer. This protein has potential diagnostic and/or therapeutic implications based on association with the following diseases: Prostatic Neoplasms (J Steroid Biochem Mol Biol 1999 January; 68(1-2):41-50). (PhosphoSite®, Cell Signaling Technology (Danvers, Mass.), Human PSD™, Biobase Corporation, (Beverly, Mass.)).

TOX, phosphorylated at Y511, is among the proteins listed in this patent. TOX, Protein with strong similarity to thymocyte selection-associated HMG box gene (mouse Tox), which is a putative transcription factor that stimulates T cell differentiation, contains a high mobility group box (HMG1 or 2) family domain. (PhosphoSite®, Cell Signaling Technology (Danvers, Mass.), Human PSD™, Biobase Corporation, (Beverly, Mass.)).

ABLIM1 is a cytoskeletal LIM protein consisting of a C-terminal cytoskeletal domain fused to an N-terminal domain of four double zinc finger motifs. The C-terminal domain is 50% identical to dematin, an actin-bundling protein of the erythroid cytoskeleton. Undergoes extensive phosphorylation in light-adapted retinas in vivo and its developmental expression in the retina coincides with the elaboration of photoreceptor inner and outer segments. LIM domain proteins play key roles in various biological processes such as embryonic development, cell lineage determination, and cancer differentiation. ABLIM1 localizes in a genomic region often deleted in human cancers and suggested to be involved in axon guidance (Int J Mol. Med. 17:129-33).

ARHGEF11, phosphorylated at T668 and T672, is among the proteins listed in this patent. ARHGEF11, Rho guanine nucleotide exchange factor (GEF) 11, an exchange factor for Rho GTPases that is involved in GPCR and Rho signaling, binds LPA receptors, Galpha-12 (GNA12), and Galpha-13 (GNA13), binds actin and regulates stress fiber formation and cell shape. (PhosphoSite®, Cell Signaling Technology (Danvers, Mass.), Human PSD™, Biobase Corporation, (Beverly, Mass.)).

RAPGEF6, phosphorylated at Y1490, is among the proteins listed in this patent. RAPGEF6, Rap guanine nucleotide exchange factor, a guanine nucleotide exchange factor for RAP1A and RAP2A that localizes to the plasma membrane via association with MRAS and may mediate MRAS activation of Rap1. (PhosphoSite®, Cell Signaling Technology (Danvers, Mass.), Human PSD™, Biobase Corporation, (Beverly, Mass.)).

INPP4A, phosphorylated at Y933, is among the proteins listed in this patent. INPP4A, Inositol polyphosphate-4-phosphatase I, an Mg2+-independent enzyme that binds phosphoinositide and has phosphatidylinositol phosphatase activity, involved in inositol phosphate signaling, negatively regulates cell proliferation. (PhosphoSite®, Cell Signaling Technology (Danvers, Mass.), Human PSD™, Biobase Corporation, (Beverly, Mass.)).

CDK10, phosphorylated at T167, is among the proteins listed in this patent. CDK10, Cyclin dependent kinase (CDC2-like)10, binds and inhibits the activity of transcription factor ETS2, regulates cell cycle progression and cell proliferation; upregulated in follicular lymphoma. This protein has potential diagnostic and/or therapeutic implications based on association with the following diseases: Follicular Lymphoma (Blood 2002 Jan. 1; 99(1):282-9). (PhosphoSite®, Cell Signaling Technology (Danvers, Mass.), Human PSD™, Biobase Corporation, (Beverly, Mass.)).

DCAMKL1, phosphorylated at S334, S337 and S340, is among the proteins listed in this patent. DCAMKL1, Doublecortin and CaM kinase-like 1, a microtubule associated kinase that may regulate microtubule polymerization, central nervous system development, and calcium mediated signaling. (PhosphoSite®, Cell Signaling Technology (Danvers, Mass.), Human PSD™, Biobase Corporation, (Beverly, Mass.)).

ABCE1, phosphorylated at Y594, is among the proteins listed in this patent. ABCE1, ATP-binding cassette subfamily E member 1, an RNAase L inhibitor that binds to translation initiation factors and HIV-1 Gag, inhibits HIV-1 replication and acts in assembly of HIV-1 capsids; gene expression is increased in systemic lupus erythematosus. This protein has potential diagnostic and/or therapeutic implications based on association with the following diseases: Neoplasms (Cancer Res 2004 Feb. 15; 64(4):1403-10). (PhosphoSite®, Cell Signaling Technology (Danvers, Mass.), Human PSD™, Biobase Corporation, (Beverly, Mass.)).

NISCH, phosphorylated at Y1307, is among the proteins listed in this patent. NISCH, Nischarin, an I-1 imidazoline receptor that plays a role in cAMP-mediated signaling and is associated with hypertension. (PhosphoSite®, Cell Signaling Technology (Danvers, Mass.), Human PSD™, Biobase Corporation, (Beverly, Mass.)).

HNRPH2, phosphorylated at S104, is among the proteins listed in this patent. HNRPH2, Heterogeneous nuclear ribonucleoprotein H2 (H'), a putative heterogeneous nuclear ribonucleoprotein that recognizes the pre-mRNA motifs GGGA and GGGGGC. (PhosphoSite®, Cell Signaling Technology (Danvers, Mass.), Human PSD™, Biobase Corporation, (Beverly, Mass.)).

PCBP1, phosphorylated at Y183, is among the proteins listed in this patent. PCBP1, Poly(rC)-binding protein 1, binds poly(rC) RNA and telomeric DNA, plays a role in mRNA stability and acts as a repressor of HPV-16 L2 viral mRNA translation, altered expression is linked to cardiac diseases, cervical dysplasia and invasive cervical cancer. (PhosphoSite®, Cell Signaling Technology (Danvers, Mass.), Human PSD™, Biobase Corporation, (Beverly, Mass.)).

TARBP2, phosphorylated at S131, is among the proteins listed in this patent. TARBP2, TAR (HIV-1) RNA-binding protein 2, an RNA binding protein that binds dicer (DICER1), PKR (EIF2AK2), and Merlin (NF2), involved in cell proliferation and siRNA- and miRNA-mediated RNA silencing, regulates kinase activity and transcription. (PhosphoSite®, Cell Signaling Technology (Danvers, Mass.), Human PSD™, Biobase Corporation, (Beverly, Mass.)).

ATF7, phosphorylated at S97 and T101, is among the proteins listed in this patent. ATF7, Activating transcription factor 7, a DNA binding protein that regulates transcription from cellular cAMP-inducible and adenovirus Ela-responsive promoters, activity may contribute to epithelial tissue differentiation. (PhosphoSite®, Cell Signaling Technology (Danvers, Mass.), Human PSD™, Biobase Corporation, (Beverly, Mass.)).

DMAP1, phosphorylated at S412, is among the proteins listed in this patent. DMAP1, DNA methyltransferase 1 associated protein 1, binds human TSG101, may complex with human HDAC2 and DNMT1 at replication loci, may negatively regulate transcription, contains a putative coiled-coil domain and a likely nuclear localization signal. (PhosphoSite®, Cell Signaling Technology (Danvers, Mass.), Human PSD™, Biobase Corporation, (Beverly, Mass.)).

PPP1R13L, phosphorylated at Y126, is among the proteins listed in this patent. PPP1R13L, Protein phosphatase 1 regulatory (inhibitor) subunit 13 like, a transcriptional corepressor that binds p53 and RELA, inhibits apoptosis induced by p53 overexpression, inhibits transcription and replication of HIV-1, and is upregulated in breast cancer. This protein has potential diagnostic and/or therapeutic implications based on association with the following diseases: Breast Neoplasms (Nat Genet 2003 February; 33(2):162-7). (PhosphoSite®, Cell Signaling Technology (Danvers, Mass.), Human PSD™, Biobase Corporation, (Beverly, Mass.)).

RB1, phosphorylated at 5794, is among the proteins listed in this patent. RB1, Retinoblastoma 1, a tumor suppressor that acts in haemopoiesis, cell cycle arrest, and nucleotide-excision repair, regulates transcription, apoptosis, and cell differentiation, mutations in the corresponding gene is associated with several cancers. This protein has potential diagnostic and/or therapeutic implications based on association with the following diseases: Breast Neoplasms (Anticancer Res 1991 July-August; 11(4):1501-7). (PhosphoSite®, Cell Signaling Technology (Danvers, Mass.), Human PSD™, Biobase Corporation, (Beverly, Mass.)).

SIAHBP1, phosphorylated at T60, is among the proteins listed in this patent. SIAHBP1, Siah (seven-in-absentia homolog) binding protein 1 (fuse binding protein interacting repressor), a transcriptional repressor that binds FUBP1 and subunits of the TFIIH, contains RNA recognition motifs and localizes to the nucleus. (PhosphoSite®, Cell Signaling Technology (Danvers, Mass.), Human PSD™, Biobase Corporation, (Beverly, Mass.)).

ZNFN1A1, phosphorylated at Y413, is among the proteins listed in this patent. ZNFN1A1, Zinc finger protein subfamily 1A 1 (Ikaros), a zinc finger transcription factor, regulates development and homeostasis of the lymphopoietic system, altered expression of dominant negative alternative form contributes to leukemias and lymphomas. This protein has potential diagnostic and/or therapeutic implications based on association with the following diseases: B-Cell Lymphoma, Large-Cell Lymphoma (Blood 2000 Apr. 15; 95(8):2719-21). (PhosphoSite®, Cell Signaling Technology (Danvers, Mass.), Human PSD™, Biobase Corporation, (Beverly, Mass.)).

EEF1G, phosphorylated at S387, is among the proteins listed in this patent. EEF1G, Eukaryotic translation elongation factor 1 gamma, a putative translation elongation factor 1 (EF-1) complex subunit that binds cytoplasmic cysteinyl-tRNA synthetase and possibly EF-1 beta, upregulated in gastric and colorectal cancer. This protein has potential diagnostic and/or therapeutic implications based on association with the following diseases: Stomach Neoplasms (Cancer 1995 Mar. 15; 75(6 Suppl):1446-9). (PhosphoSite®, Cell Signaling Technology (Danvers, Mass.), Human PSD™, Biobase Corporation, (Beverly, Mass.)).

The invention also provides peptides comprising a novel phosphorylation site of the invention. In one particular embodiment, the peptides comprise any one of the amino acid sequences as set forth in SEQ ID NOs: 1-155, which are trypsin-digested peptide fragments of the parent proteins. Alternatively, a parent signaling protein listed in Table 1 may be digested with another protease, and the sequence of a peptide fragment comprising a phosphorylation site can be obtained in a similar way. Suitable proteases include, but are not limited to, serine proteases (e.g. hepsin), metallo proteases (e.g. PUMP1), chymotrypsin, cathepsin, pepsin, thermolysin, carboxypeptidases, etc.

The invention also provides proteins and peptides that are mutated to eliminate a novel phosphorylation site of the invention. Such proteins and peptides are particular useful as research tools to understand complex signaling transduction pathways of cancer cells, for example, to identify new upstream kinase(s) or phosphatase(s) or other proteins that regulates the activity of a signaling protein; to identify downstream effector molecules that interact with a signaling protein, etc.

Various methods that are well known in the art can be used to eliminate a phosphorylation site. For example, the phosphorylatable tyrosine, serine and/or threonine may be mutated into a non-phosphorylatable residue, such as phenylalanine. A "phosphorylatable" amino acid refers to an amino acid that is capable of being modified by addition of a phosphate group (any includes both phosphorylated form and unphosphorylated form). Alternatively, the tyrosine, serine and/or threonine may be deleted. Residues other than the tyrosine, serine and/or threonine may also be modified (e.g., delete or mutated) if such modification inhibits the phosphorylation of the tyrosine, serine and/or threonine residue. For example, residues flanking the tyrosine, serine and/or threonine may be deleted or mutated, so that a kinase cannot recognize/phosphorylate the mutated protein or the peptide. Standard mutagenesis and molecular cloning techniques can be used to create amino acid substitutions or deletions.

2. Modulators of the Phosphorylation Sites

In another aspect, the invention provides a modulator that modulates tyrosine, serine and/or threonine phosphorylation at a novel phosphorylation site of the invention, including small molecules, peptides comprising a novel phosphorylation site, and binding molecules that specifically bind at a novel phosphorylation site, including but not limited to antibodies or antigen-binding fragments thereof.

Modulators of a phosphorylation site include any molecules that directly or indirectly counteract, reduce, antagonize or inhibit tyrosine, serine and/or threonine phosphorylation of the site. The modulators may compete or block the binding of the phosphorylation site to its upstream kinase(s) or phosphatase(s), or to its downstream signaling transduction molecule(s).

The modulators may directly interact with a phosphorylation site. The modulator may also be a molecule that does not directly interact with a phosphorylation site. For example, the modulators can be dominant negative mutants, i.e., proteins and peptides that are mutated to eliminate the phosphorylation site. Such mutated proteins or peptides could retain the binding ability to a downstream signaling molecule but lose the ability to trigger downstream signaling transduction of the wild type parent signaling protein.

The modulators include small molecules that modulate the tyrosine, serine and/or threonine phosphorylation at a novel phosphorylation site of the invention. Chemical agents, referred to in the art as "small molecule" compounds are typically organic, non-peptide molecules, having a molecular weight less than 10,000, less than 5,000, less than 1,000, or less than 500 daltons. This class of modulators includes chemically synthesized molecules, for instance, compounds from combinatorial chemical libraries. Synthetic compounds may be rationally designed or identified based on known or inferred properties of a phosphorylation site of the invention or may be identified by screening compound libraries. Alternative appropriate modulators of this class are natural products, particularly secondary metabolites from organisms such as plants or fungi, which can also be identified by screening compound libraries. Methods for generating and obtaining compounds are well known in the art (Schreiber S L, Science 151: 1964-1969 (2000); Radmann J. and Gunther J., Science 151: 1947-1948 (2000)).

The modulators also include peptidomimetics, small protein-like chains designed to mimic peptides. Peptidomimetics may be analogues of a peptide comprising a phosphorylation site of the invention. Peptidomimetics may also be analogues of a modified peptide that are mutated to eliminate a phosphorylation site of the invention. Peptidomimetics (both peptide and non-peptidyl analogues) may have improved properties (e.g., decreased proteolysis, increased retention or increased bioavailability). Peptidomimetics generally have improved oral availability, which makes them especially suited to treatment of disorders in a human or animal.

In certain embodiments, the modulators are peptides comprising a novel phosphorylation site of the invention. In certain embodiments, the modulators are antibodies or antigen-binding fragments thereof that specifically bind at a novel phosphorylation site of the invention.

3. Heavy-Isotope Labeled Peptides (AQUA Peptides).

In another aspect, the invention provides peptides comprising a novel phosphorylation site of the invention. In a particular embodiment, the invention provides Heavy-Isotype Labeled Peptides (AQUA peptides) comprising a novel phosphorylation site. Such peptides are useful to generate phosphorylation site-specific antibodies for a novel phosphorylation site. Such peptides are also useful as potential diagnostic tools for screening for diseases such as carcinoma or leukemia, or as potential therapeutic agents for treating diseases such as carcinoma or leukemia.

The peptides may be of any length, typically six to fifteen amino acids. The novel tyrosine, serine and/or threonine phosphorylation site can occur at any position in the peptide; if the peptide will be used as an immunogen, it preferably is from seven to twenty amino acids in length. In some embodiments, the peptide is labeled with a detectable marker.

"Heavy-isotope labeled peptide" (used interchangeably with AQUA peptide) refers to a peptide comprising at least one heavy-isotope label, as described in WO/03016861, "Absolute Quantification of Proteins and Modified Forms Thereof by Multistage Mass Spectrometry" (Gygi et al.) (the teachings of which are hereby incorporated herein by reference, in their entirety). The amino acid sequence of an AQUA peptide is identical to the sequence of a proteolytic fragment of the parent protein in which the novel phosphorylation site occurs. AQUA peptides of the invention are highly useful for detecting, quantitating or modulating a phosphorylation site of the invention (both in phosphorylated and unphosphorylated forms) in a biological sample.

A peptide of the invention, including an AQUA peptides comprises any novel phosphorylation site. Preferably, the peptide or AQUA peptide comprises a novel phosphorylation site of a protein in Table 1 that is an adaptor/scaffold protein, protein kinase, enzyme protein, ubiquitan conjugating system protein, chromatin or DNA binding/repair protein, g protein or regulator protein, receptor/channel/transporter/cell surface protein, RNA binding protein, transcriptional regulator protein or an adhesion/extra-cellular matrix protein.

Particularly preferred peptides and AQUA peptides are these comprising a novel tyrosine, serine and/or threonine phosphorylation site (shown as a lower case "y," "s" or "t" (respectively) within the sequences listed in Table 1) selected from the group consisting of SEQ ID NOs: 1 (AHNAK); 3 (RANBP9); 8 (TFG); 50 (CDK10); 51 (DCAMKL1); 52 (DCAMKL1); 53 (DCAMKL1); 34 (EZH2); 35 (EZH2); 36 (IARS); 17 (APRIN); 18 (APRIN); 19 (APRIN); 42 (RAB3IL1); 61 (ABCE1); 70 (PCBP1); 74 (ATF7); 75 (ATF7); 85 (RB1); 87 (SUPT5H); 88 (SUPT5H), 89 (YBX1); 90 (ZNFN1A1); 13 (CIAPIN1); 16 (ORC3L1); 25 (MAP1A); 26 (NDE1); 46 (INPP4A); 47 (HGFAC); 91 (EEF1G); 102 (C11orf2); 111 (C9orf30); 134 (LTV1); 154 (GOLGB1); and 155 (NISCH).

In some embodiments, the peptide or AQUA peptide comprises the amino acid sequence shown in any one of the above listed SEQ ID NOs. In some embodiments, the peptide or AQUA peptide consists of the amino acid sequence in said SEQ ID NOs. In some embodiments, the peptide or AQUA peptide comprises a fragment of the amino acid sequence in said SEQ ID NOs., wherein the fragment is six to twenty amino acid long and includes the phosphorylatable tyrosine, serine and/or threonine. In some embodiments, the peptide or AQUA peptide consists of a fragment of the amino acid sequence in said SEQ ID NOs., wherein the fragment is six to twenty amino acid long and includes the phosphorylatable tyrosine, serine and/or threonine.

In certain embodiments, the peptide or AQUA peptide comprises any one of SEQ ID NOs: 1-155, which are trypsin-digested peptide fragments of the parent proteins.

It is understood that parent protein listed in Table 1 may be digested with any suitable protease (e.g., serine proteases (e.g. trypsin, hepsin), metallo proteases (e.g. PUMP1), chymotrypsin, cathepsin, pepsin, thermolysin, carboxypeptidases, etc), and the resulting peptide sequence comprising a phosphorylated site of the invention may differ from that of trypsin-digested fragments (as set forth in Column E), depending the cleavage site of a particular enzyme. An AQUA peptide for a particular a parent protein sequence should be chosen based on the amino acid sequence of the parent protein and the particular protease for digestion; that is, the AQUA peptide should match the amino acid sequence of a proteolytic fragment of the parent protein in which the novel phosphorylation site occurs.

An AQUA peptide is preferably at least about 6 amino acids long. The preferred ranged is about 7 to 15 amino acids.

The AQUA method detects and quantifies a target protein in a sample by introducing a known quantity of at least one heavy-isotope labeled peptide standard (which has a unique signature detectable by LC-SRM chromatography) into a digested biological sample. By comparing to the peptide standard, one may readily determines the quantity of a peptide having the same sequence and protein modification(s) in the biological sample. Briefly, the AQUA methodology has two stages: (1) peptide internal standard selection and validation; method development; and (2) implementation using validated peptide internal standards to detect and quantify a target protein in a sample. The method is a powerful technique for detecting and quantifying a given peptide/protein within a complex biological mixture, such as a cell lysate, and may be used, e.g., to quantify change in protein phosphorylation as a result of drug treatment, or to quantify a protein in different biological states.

Generally, to develop a suitable internal standard, a particular peptide (or modified peptide) within a target protein sequence is chosen based on its amino acid sequence and a particular protease for digestion. The peptide is then generated by solid-phase peptide synthesis such that one residue is replaced with that same residue containing stable isotopes ($^{13}C$, $^{15}N$). The result is a peptide that is chemically identical to its native counterpart formed by proteolysis, but is easily distinguishable by MS via a mass shift. A newly synthesized AQUA internal standard peptide is then evaluated by LC-MS/MS. This process provides qualitative information about peptide retention by reverse-phase chromatography, ionization efficiency, and fragmentation via collision-induced dissociation. Informative and abundant fragment ions for sets of native and internal standard peptides are chosen and then specifically monitored in rapid succession as a function of chromatographic retention to form a selected reaction monitoring (LC-SRM) method based on the unique profile of the peptide standard.

The second stage of the AQUA strategy is its implementation to measure the amount of a protein or the modified form of the protein from complex mixtures. Whole cell lysates are typically fractionated by SDS-PAGE gel electrophoresis, and regions of the gel consistent with protein migration are excised. This process is followed by in-gel proteolysis in the presence of the AQUA peptides and LC-SRM analysis. (See Gerber et al. supra.) AQUA peptides are spiked in to the complex peptide mixture obtained by digestion of the whole cell lysate with a proteolytic enzyme and subjected to immunoaffinity purification as described above. The retention time and fragmentation pattern of the native peptide formed by digestion (e.g., trypsinization) is identical to that of the AQUA internal standard peptide determined previously; thus, LC-MS/MS analysis using an SRM experiment results in the highly specific and sensitive measurement of both internal standard and analyte directly from extremely complex peptide mixtures. Because an absolute amount of the AQUA peptide is added (e.g. 250 fmol), the ratio of the areas under the curve can be used to determine the precise expression levels of a protein or phosphorylated form of a protein in the original cell lysate. In addition, the internal standard is present during in-gel digestion as native peptides are formed, such that peptide extraction efficiency from gel pieces, absolute losses during sample handling (including vacuum centrifugation), and variability during introduction into the LC-MS system do not affect the determined ratio of native and AQUA peptide abundances.

An AQUA peptide standard may be developed for a known phosphorylation site previously identified by the IAP-LC-MS/MS method within a target protein. One AQUA peptide incorporating the phosphorylated form of the site, and a second AQUA peptide incorporating the unphosphorylated form of site may be developed. In this way, the two standards may be used to detect and quantify both the phosphorylated and unphosphorylated forms of the site in a biological sample.

Peptide internal standards may also be generated by examining the primary amino acid sequence of a protein and determining the boundaries of peptides produced by protease cleavage. Alternatively, a protein may actually be digested with a protease and a particular peptide fragment produced can then sequenced. Suitable proteases include, but are not limited to, serine proteases (e.g. trypsin, hepsin), metallo proteases (e.g. PUMP1), chymotrypsin, cathepsin, pepsin, thermolysin, carboxypeptidases, etc.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Thus, a peptide is preferably at least about 6 amino acids. The size of the peptide is also optimized to maximize ionization frequency. Thus, peptides longer than about 20 amino acids are not preferred. The preferred ranged is about 7 to 15 amino acids. A peptide sequence is also selected that is not likely to be chemically reactive during mass spectrometry, thus sequences comprising cysteine, tryptophan, or methionine are avoided.

A peptide sequence that is outside a phosphorylation site may be selected as internal standard to determine the quantity of all forms of the target protein. Alternatively, a peptide encompassing a phosphorylated site may be selected as internal standard to detect and quantify only the phosphorylated form of the target protein. Peptide standards for both phosphorylated form and unphosphorylated form can be used together, to determine the extent of phosphorylation in a particular sample.

The peptide is labeled using one or more labeled amino acids (i.e. the label is an actual part of the peptide) or less preferably, labels may be attached after synthesis according to standard methods. Preferably, the label is a mass-altering label selected based on the following considerations: The mass should be unique to shift fragment masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. As a result, the labeled amino acids and peptides are readily distinguished from unlabeled ones by the ion/mass pattern in the resulting mass spectrum.

Preferably, the ion mass signature component imparts a mass to a protein fragment that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label preferably does not suppress the ionization efficiency of the protein and is not chemically reactive. The label may contain a mixture of two or more isotopically distinct species to generate a unique mass spectrometric pattern at each labeled fragment position. Stable isotopes, such as $^{13}C$, $^{15}N$, $^{17}O$, $^{18}O$ or $^{34}S$, are among preferred labels. Pairs of peptide internal standards that incorporate a different isotope label may also be prepared. Preferred amino acid residues into which a heavy isotope label may be incorporated include leucine, proline, valine, and phenylalanine.

Peptide internal standards are characterized according to their mass-to-charge (m/z) ratio, and preferably, also according to their retention time on a chromatographic column (e.g. an HPLC column). Internal standards that co-elute with unlabeled peptides of identical sequence are selected as optimal internal standards. The internal standard is then analyzed by fragmenting the peptide by any suitable means, for example by collision-induced dissociation (CID) using, e.g., argon or helium as a collision gas. The fragments are then analyzed, for example by multi-stage mass spectrometry ($MS_n$) to obtain a fragment ion spectrum, to obtain a peptide fragmentation signature. Preferably, peptide fragments have significant differences in m/z ratios to enable peaks corresponding to each fragment to be well separated, and a signature that is unique for the target peptide is obtained. If a suitable fragment signature is not obtained at the first stage, additional stages of MS are performed until a unique signature is obtained.

Fragment ions in the MS/MS and $MS^3$ spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified cell extracts are preferably used. Generally, the sample has at least 0.01 mg of protein, typically a concentration of 0.1-10 mg/mL, and may be adjusted to a desired buffer concentration and pH.

A known amount of a labeled peptide internal standard, preferably about 10 femtomoles, corresponding to a target protein to be detected/quantified is then added to a biological sample, such as a cell lysate. The spiked sample is then digested with one or more protease(s) for a suitable time period to allow digestion. A separation is then performed (e.g., by HPLC, reverse-phase HPLC, capillary electrophoresis, ion exchange chromatography, etc.) to isolate the labeled internal standard and its corresponding target peptide from other peptides in the sample. Microcapillary LC is a preferred method.

Each isolated peptide is then examined by monitoring of a selected reaction in the MS. This involves using the prior knowledge gained by the characterization of the peptide internal standard and then requiring the MS to continuously monitor a specific ion in the MS/MS or $MS^n$ spectrum for both the peptide of interest and the internal standard. After elution, the area under the curve (AUC) for both peptide standard and target peptide peaks are calculated. The ratio of the two areas provides the absolute quantification that can be normalized for the number of cells used in the analysis and the protein's molecular weight, to provide the precise number of copies of the protein per cell. Further details of the AQUA methodology are described in Gygi et al., and Gerber et al. supra.

Accordingly, AQUA internal peptide standards (heavy-isotope labeled peptides) may be produced, as described above, for any of the 155 novel phosphorylation sites of the invention (see Table 1/FIGS. 2A-2M). For example, peptide standards for a given phosphorylation site (e.g., an AQUA peptide having the sequence VADSDyEAICKVPR (SEQ ID NO: 2), wherein "y" corresponds to phosphorylatable tyrosine 180 of PDE4DIP) may be produced for both the phosphorylated and unphosphorylated forms of the sequence. Such standards may be used to detect and quantify both phosphorylated form and unphosphorylated form of the parent signaling protein (e.g., PDE4DIP) in a biological sample.

Heavy-isotope labeled equivalents of a phosphorylation site of the invention, both in phosphorylated and unphosphorylated form, can be readily synthesized and their unique MS and LC-SRM signature determined, so that the peptides are validated as AQUA peptides and ready for use in quantification.

The novel phosphorylation sites of the invention are particularly well suited for development of corresponding AQUA peptides, since the IAP method by which they were identified (see Part A above and Example 1) inherently confirmed that such peptides are in fact produced by enzymatic digestion (e.g., trypsinization) and are in fact suitably fractionated/ionized in MS/MS. Thus, heavy-isotope labeled equivalents of these peptides (both in phosphorylated and unphosphorylated form) can be readily synthesized and their unique MS and LC-SRM signature determined, so that the peptides are validated as AQUA peptides and ready for use in quantification experiments.

Accordingly, the invention provides heavy-isotope labeled peptides (AQUA peptides) that may be used for detecting, quantitating, or modulating any of the phosphorylation sites of the invention (Table 1). For example, an AQUA peptide having the sequence TVSHLyQESISK (SEQ ID NO: 7), wherein y (Tyr 1827) is phosphotyrosine, and wherein V=labeled valine (e.g., $^{14}C$)) is provided for the quantification of phosphorylated (or unphosphorylated) form of TANC1 (an adaptor/scaffold protein) in a biological sample.

Example 4 is provided to further illustrate the construction and use, by standard methods described above, of exemplary AQUA peptides provided by the invention. For example, AQUA peptides corresponding to both the phosphorylated and unphosphorylated forms of SEQ ID NO: 7 (a trypsin-digested fragment of TANC1, with a Tyrosine 1827 phosphorylation site) may be used to quantify the amount of phosphorylated TANC1 in a biological sample, e.g., a tumor cell sample or a sample before or after treatment with a therapeutic agent.

Peptides and AQUA peptides provided by the invention will be highly useful in the further study of signal transduction anomalies underlying cancer, including carcinomas and leukemias. Peptides and AQUA peptides of the invention may also be used for identifying diagnostic/bio-markers of carcinomas, identifying new potential drug targets, and/or monitoring the effects of test therapeutic agents on signaling proteins and pathways.

4. Phosphorylation Site-Specific Antibodies

In another aspect, the invention discloses phosphorylation site-specific binding molecules that specifically bind at a novel tyrosine, serine and/or threonine phosphorylation site of the invention, and that distinguish between the phosphorylated and unphosphorylated forms. In one embodiment, the binding molecule is an antibody or an antigen-binding fragment thereof. The antibody may specifically bind to an amino acid sequence comprising a phosphorylation site identified in Table 1.

In some embodiments, the antibody or antigen-binding fragment thereof specifically binds the phosphorylated site. In other embodiments, the antibody or antigen-binding fragment thereof specially binds the unphosphorylated site. An antibody or antigen-binding fragment thereof specially binds an amino acid sequence comprising a novel tyrosine, serine and/or threonine phosphorylation site in Table 1 when it does not significantly bind any other site in the parent protein and does not significantly bind a protein other than the parent protein. An antibody of the invention is sometimes referred to herein as a "phospho-specific" antibody.

An antibody or antigen-binding fragment thereof specially binds an antigen when the dissociation constant is ≤1 mM, preferably ≤100 nM, and more preferably ≤10 nM.

In some embodiments, the antibody or antigen-binding fragment of the invention binds an amino acid sequence that comprises a novel phosphorylation site of a protein in Table 1 that is adaptor/scaffold protein, protein kinase, enzyme protein, ubiquitan conjugating system protein, chromatin or DNA binding/repair protein, g proteins or regulator protein, receptor/channel/transporter/cell surface protein, RNA binding protein, transcriptional regulator protein or an adhesion/extra-cellular matrix protein.

In particularly preferred embodiments, an antibody or antigen-binding fragment thereof of the invention specially binds an amino acid sequence comprising a novel tyrosine, serine and/or threonine phosphorylation site shown as a lower case "y," "s," or "t" (respectively) in a sequence listed in Table 1 selected from the group consisting of SEQ ID NOS: 1 (AHNAK); 3 (RANBP9); 8 (TFG); 50 (CDK10); 51 (DCAMKL1); 52 (DCAMKL1); 53 (DCAMKL1); 34 (EZH2); 35 (EZH2); 36 (IARS); 17 (APRIN); 18 (APRIN); 19 (APRIN); 42 (RAB3IL1); 61 (ABCE1); 70 (PCBP1); 74 (ATF7); 75 (ATF7); 85 (RB1); 87 (SUPT5H); 88 (SUPT5H); 89 (YBX1); 90 (ZNFN1A1); 13 (CIAPIN1); 16 (ORC3L1); 25 (MAP1A); 26 (NDE1); 46 (INPP4A); 47 (HGFAC); 91 (EEF1G); 102 (C11orf2); 111 (C9orf30); 134 (LTV1); 154 (GOLGB1); and 155 (NISCH).

In some embodiments, an antibody or antigen-binding fragment thereof of the invention specifically binds an amino acid sequence comprising any one of the above listed SEQ ID NOs. In some embodiments, an antibody or antigen-binding fragment thereof of the invention especially binds an amino acid sequence comprises a fragment of one of said SEQ ID NOs., wherein the fragment is four to twenty amino acid long and includes the phosphorylatable tyrosine, serine and/or threonine.

In certain embodiments, an antibody or antigen-binding fragment thereof of the invention specially binds an amino acid sequence that comprises a peptide produced by proteolysis of the parent protein with a protease wherein said peptide comprises a novel tyrosine, serine and/or threonine phosphorylation site of the invention. In some embodiments, the peptides are produced from trypsin digestion of the parent protein. The parent protein comprising the novel tyrosine, serine and/or threonine phosphorylation site can be from any species, preferably from a mammal including but not limited to non-human primates, rabbits, mice, rats, goats, cows, sheep, and guinea pigs. In some embodiments, the parent protein is a human protein and the antibody binds an epitope comprising the novel tyrosine, serine and/or threonine phosphorylation site shown by a lower case "y," "s" or "t" in Column E of Table 1. Such peptides include any one of SEQ ID NOs: 1-155.

An antibody of the invention can be an intact, four immunoglobulin chain antibody comprising two heavy chains and two light chains. The heavy chain of the antibody can be of any isotype including IgM, IgG, IgE, IgG, IgA or IgD or sub-isotype including IgG1, IgG2, IgG3, IgG4, IgE1, IgE2, etc. The light chain can be a kappa light chain or a lambda light chain.

Also within the invention are antibody molecules with fewer than 4 chains, including single chain antibodies, Camelid antibodies and the like and components of the antibody, including a heavy chain or a light chain. The term "antibody" (or "antibodies") refers to all types of immunoglobulins. The term "an antigen-binding fragment of an antibody" refers to any portion of an antibody that retains specific binding of the intact antibody. An exemplary antigen-binding fragment of an antibody is the heavy chain and/or light chain CDR, or the heavy and/or light chain variable region. The term "does not bind," when appeared in context of an antibody's binding to one phospho-form (e.g., phosphorylated form) of a sequence, means that the antibody does not substantially react with the other phospho-form (e.g., non-phosphorylated form) of the same sequence. One of skill in the art will appreciate that the expression may be applicable in those instances when (1) a phospho-specific antibody either does not apparently bind to the non-phospho form of the antigen as ascertained in commonly used experimental detection systems (Western blotting, IHC, Immunofluorescence, etc.); (2) where there is some reactivity with the surrounding amino acid sequence, but that the phosphorylated residue is an immunodominant feature of the reaction. In cases such as these, there is an apparent difference in affinities for the two sequences. Dilutional analyses of such antibodies indicates that the antibodies apparent affinity for the phosphorylated form is at least 10-100 fold higher than for the non-phosphorylated form; or where (3) the phospho-specific antibody reacts no more than an appropriate control antibody would react under identical experimental conditions. A control antibody preparation might be, for instance, purified immunoglobulin from a pre-immune animal of the same species, an isotype- and species-matched monoclonal antibody. Tests using control antibodies to demonstrate specificity are recognized by one of skill in the art as appropriate and definitive.

In some embodiments an immunoglobulin chain may comprise in order from 5' to 3', a variable region and a constant region. The variable region may comprise three complementarity determining regions (CDRs), with interspersed framework (FR) regions for a structure FR1, CDR1, FR2, CDR2, FR3, CDR3 and FR4. Also within the invention are heavy or light chain variable regions, framework regions and CDRs. An antibody of the invention may comprise a heavy chain constant region that comprises some or all of a CH1 region, hinge, CH2 and CH3 region.

An antibody of the invention may have an binding affinity ($K_D$) of $1\times10^{-7}$ M or less. In other embodiments, the antibody binds with a $K_D$ of $1\times10^{-8}$ M, $1\times10^{-9}$ M, $1\times10^{-10}$ M, $1\times10^{-11}$ M, $1\times10^{-12}$ M or less. In certain embodiments, the $K_D$ is 1 pM to 500 pM, between 500 pM to 1 µM, between 1 µM to 100 nM, or between 100 mM to 10 nM.

Antibodies of the invention can be derived from any species of animal, preferably a mammal. Non-limiting exemplary natural antibodies include antibodies derived from human, chicken, goats, and rodents (e.g., rats, mice, hamsters and rabbits), including transgenic rodents genetically engineered to produce human antibodies (see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety). Natural antibodies are the antibodies produced by a host animal. "Genetically altered antibodies" refer to antibodies wherein the amino acid sequence has been varied from that of a native antibody. Because of the relevance of recombinant DNA techniques to this application, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics.

The antibodies of the invention include antibodies of any isotype including IgM, IgG, IgD, IgA and IgE, and any sub-isotype, including IgG1, IgG2a, IgG2b, IgG3 and IgG4, IgE1, IgE2 etc. The light chains of the antibodies can either be kappa light chains or lambda light chains.

Antibodies disclosed in the invention may be polyclonal or monoclonal. As used herein, the term "epitope" refers to the smallest portion of a protein capable of selectively binding to the antigen binding site of an antibody. It is well accepted by those skilled in the art that the minimal size of a protein epitope capable of selectively binding to the antigen binding site of an antibody is about five or six to seven amino acids.

Other antibodies specifically contemplated are oligoclonal antibodies. As used herein, the phrase "oligoclonal antibodies" refers to a predetermined mixture of distinct monoclonal antibodies. See, e.g., PCT publication WO 95/20401; U.S. Pat. Nos. 5,789,208 and 6,335,163. In one embodiment, oligoclonal antibodies consisting of a predetermined mixture of antibodies against one or more epitopes are generated in a single cell. In other embodiments, oligoclonal antibodies comprise a plurality of heavy chains capable of pairing with a common light chain to generate antibodies with multiple specificities (e.g., PCT publication WO 04/009618). Oligoclonal antibodies are particularly useful when it is desired to target multiple epitopes on a single target molecule. In view of the assays and epitopes disclosed herein, those skilled in the art can generate or select antibodies or mixtures of antibodies that are applicable for an intended purpose and desired need.

Recombinant antibodies against the phosphorylation sites identified in the invention are also included in the present application. These recombinant antibodies have the same amino acid sequence as the natural antibodies or have altered amino acid sequences of the natural antibodies in the present application. They can be made in any expression systems including both prokaryotic and eukaryotic expression systems or using phage display methods (see, e.g., Dower et al., WO91/17271 and McCafferty et al., WO92/01047; U.S. Pat. No. 5,969,108, which are herein incorporated by reference in their entirety).

Antibodies can be engineered in numerous ways. They can be made as single-chain antibodies (including small modular immunopharmaceuticals or SMIPs™), Fab and F(ab')$_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203.

The genetically altered antibodies should be functionally equivalent to the above-mentioned natural antibodies. In certain embodiments, modified antibodies provide improved stability or/and therapeutic efficacy. Examples of modified antibodies include those with conservative substitutions of amino acid residues, and one or more deletions or additions of amino acids that do not significantly deleteriously alter the antigen binding utility. Substitutions can range from changing or modifying one or more amino acid residues to complete redesign of a region as long as the therapeutic utility is maintained. Antibodies of this application can be modified post-translationally (e.g., acetylation, and/or phosphorylation) or can be modified synthetically (e.g., the attachment of a labeling group).

Antibodies with engineered or variant constant or Fc regions can be useful in modulating effector functions, such as, for example, antigen-dependent cytotoxicity (ADCC) and complement-dependent cytotoxicity (CDC). Such antibodies with engineered or variant constant or Fc regions may be useful in instances where a parent singling protein (Table 1) is expressed in normal tissue; variant antibodies without effector function in these instances may elicit the desired therapeutic response while not damaging normal tissue. Accordingly, certain aspects and methods of the present disclosure relate to antibodies with altered effector functions that comprise one or more amino acid substitutions, insertions, and/or deletions.

In certain embodiments, genetically altered antibodies are chimeric antibodies and humanized antibodies.

The chimeric antibody is an antibody having portions derived from different antibodies. For example, a chimeric antibody may have a variable region and a constant region derived from two different antibodies. The donor antibodies may be from different species. In certain embodiments, the variable region of a chimeric antibody is non-human, e.g., murine, and the constant region is human.

The genetically altered antibodies used in the invention include CDR grafted humanized antibodies. In one embodiment, the humanized antibody comprises heavy and/or light chain CDRs of a non-human donor immunoglobulin and heavy chain and light chain frameworks and constant regions of a human acceptor immunoglobulin. The method of making humanized antibody is disclosed in U.S. Pat. Nos. 5,530,101; 5,585,089; 5,693,761; 5,693,762; and 6,180,370 each of which is incorporated herein by reference in its entirety.

Antigen-binding fragments of the antibodies of the invention, which retain the binding specificity of the intact antibody, are also included in the invention. Examples of these antigen-binding fragments include, but are not limited to, partial or full heavy chains or light chains, variable regions, or CDR regions of any phosphorylation site-specific antibodies described herein.

In one embodiment of the application, the antibody fragments are truncated chains (truncated at the carboxyl end). In certain embodiments, these truncated chains possess one or more immunoglobulin activities (e.g., complement fixation activity). Examples of truncated chains include, but are not limited to, Fab fragments (consisting of the VL, VH, CL and CH1 domains); Fd fragments (consisting of the VH and CH1 domains); Fv fragments (consisting of VL and VH domains of a single chain of an antibody); dAb fragments (consisting of a VH domain); isolated CDR regions; (Fab')$_2$ fragments, bivalent fragments (comprising two Fab fragments linked by a disulphide bridge at the hinge region). The truncated chains can be produced by conventional biochemical techniques, such as enzyme cleavage, or recombinant DNA techniques, each of which is known in the art. These polypeptide fragments may be produced by proteolytic cleavage of intact antibodies by methods well known in the art, or by inserting stop codons at the desired locations in the vectors using site-directed mutagenesis, such as after CH1 to produce Fab fragments or after the hinge region to produce (Fab')$_2$ fragments. Single chain antibodies may be produced by joining VL- and VH-coding regions with a DNA that encodes a peptide linker connecting the VL and VH protein fragments Papain digestion of antibodies produces two identical antigen-binding fragments, called "Fab" fragments, each with a single antigen-binding site, and a residual "Fc" fragment, whose name reflects its ability to crystallize readily. Pepsin treatment of an antibody yields an F(ab')$_2$ fragment that has two antigen-combining sites and is still capable of cross-linking antigen.

"Fv" usually refers to the minimum antibody fragment that contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the CDRs confer antigen-binding specificity to the antibody. However, even a single variable domain (or half of an Fv comprising three CDRs specific for an antigen) has the ability to recognize and bind antigen, although likely at a lower affinity than the entire binding site.

Thus, in certain embodiments, the antibodies of the application may comprise 1, 2, 3, 4, 5, 6, or more CDRs that recognize the phosphorylation sites identified in Column E of Table 1.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

"Single-chain Fv" or "scFv" antibody fragments comprise the $V_H$ and $V_L$ domains of an antibody, wherein these domains are present in a single polypeptide chain. In certain embodiments, the Fv polypeptide further comprises a polypeptide linker between the $V_H$ and $V_L$ domains that enables the scFv to form the desired structure for antigen binding. For a review of scFv see Pluckthun in The Pharmacology of Monoclonal Antibodies, vol. 113, Rosenburg and Moore, eds. (Springer-Verlag: New York, 1994), pp. 269-315.

SMIPs are a class of single-chain peptides engineered to include a target binding region and effector domain (CH2 and CH3 domains). See, e.g., U.S. Patent Application Publication No. 20050238646. The target binding region may be derived from the variable region or CDRs of an antibody, e.g., a phosphorylation site-specific antibody of the application. Alternatively, the target binding region is derived from a protein that binds a phosphorylation site.

Bispecific antibodies may be monoclonal, human or humanized antibodies that have binding specificities for at least two different antigens. In the present case, one of the binding specificities is for the phosphorylation site, the other one is for any other antigen, such as for example, a cell-surface protein or receptor or receptor subunit. Alternatively, a therapeutic agent may be placed on one arm. The therapeutic agent can be a drug, toxin, enzyme, DNA, radionuclide, etc.

In some embodiments, the antigen-binding fragment can be a diabody. The term "diabody" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90: 6444-6448 (1993).

Camelid antibodies refer to a unique type of antibodies that are devoid of light chain, initially discovered from animals of the camelid family. The heavy chains of these so-called heavy-chain antibodies bind their antigen by one single domain, the variable domain of the heavy immunoglobulin chain, referred to as VHH. VHHs show homology with the variable domain of heavy chains of the human VHIII family. The VHHs obtained from an immunized camel, dromedary, or llama have a number of advantages, such as effective production in microorganisms such as *Saccharomyces cerevisiae*.

In certain embodiments, single chain antibodies, and chimeric, humanized or primatized (CDR-grafted) antibodies, as well as chimeric or CDR-grafted single chain antibodies, comprising portions derived from different species, are also encompassed by the present disclosure as antigen-binding fragments of an antibody. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., U.S. Pat. Nos. 4,816,567 and 6,331,415; U.S. Pat. No. 4,816,397; European Patent No. 0,120,694; WO 86/01533; European Patent No. 0,194,276 B1; U.S. Pat. No. 5,225,539; and European Patent No. 0,239,400 B1. See also, Newman et al., BioTechnology, 10: 1455-1460 (1992), regarding primatized antibody. See, e.g., Ladner et al., U.S. Pat. No. 4,946,778; and Bird et al., Science, 242: 423-426 (1988)), regarding single chain antibodies.

In addition, functional fragments of antibodies, including fragments of chimeric, humanized, primatized or single chain antibodies, can also be produced. Functional fragments of the subject antibodies retain at least one binding function and/or modulation function of the full-length antibody from which they are derived.

Since the immunoglobulin-related genes contain separate functional regions, each having one or more distinct biological activities, the genes of the antibody fragments may be fused to functional regions from other genes (e.g., enzymes, U.S. Pat. No. 5,004,692, which is incorporated by reference in its entirety) to produce fusion proteins or conjugates having novel properties.

Non-immunoglobulin binding polypeptides are also contemplated. For example, CDRs from an antibody disclosed herein may be inserted into a suitable non-immunoglobulin scaffold to create a non-immunoglobulin binding polypeptide. Suitable candidate scaffold structures may be derived from, for example, members of fibronectin type III and cadherin superfamilies.

Also contemplated are other equivalent non-antibody molecules, such as protein binding domains or aptamers, which bind, in a phospho-specific manner, to an amino acid sequence comprising a novel phosphorylation site of the invention. See, e.g., Neuberger et al., Nature 312: 604 (1984). Aptamers are oligonucleic acid or peptide molecules that bind a specific target molecule. DNA or RNA aptamers are typically short oligonucleotides, engineered through repeated rounds of selection to bind to a molecular target. Peptide aptamers typically consist of a variable peptide loop attached at both ends to a protein scaffold. This double structural constraint generally increases the binding affinity of the peptide aptamer to levels comparable to an antibody (nanomolar range).

The invention also discloses the use of the phosphorylation site-specific antibodies with immunotoxins. Conjugates that are immunotoxins including antibodies have been widely described in the art. The toxins may be coupled to the antibodies by conventional coupling techniques or immunotoxins containing protein toxin portions can be produced as fusion proteins. In certain embodiments, antibody conjugates may comprise stable linkers and may release cytotoxic agents inside cells (see U.S. Pat. Nos. 6,867,007 and 6,884,869). The conjugates of the present application can be used in a corresponding way to obtain such immunotoxins. Illustrative of such immunotoxins are those described by Byers et al., Seminars Cell Biol 2:59-70 (1991) and by Fanger et al., Immunol Today 12:51-54 (1991). Exemplary immunotoxins include radiotherapeutic agents, ribosome-inactivating proteins (RIPs), chemotherapeutic agents, toxic peptides, or toxic proteins.

The phosphorylation site-specific antibodies disclosed in the invention may be used singly or in combination. The antibodies may also be used in an array format for high throughput uses. An antibody microarray is a collection of immobilized antibodies, typically spotted and fixed on a solid surface (such as glass, plastic and silicon chip).

In another aspect, the antibodies of the invention modulate at least one, or all, biological activities of a parent protein identified in Column A of Table 1. The biological activities of a parent protein identified in Column A of Table 1 include: 1) ligand binding activities (for instance, these neutralizing antibodies may be capable of competing with or completely blocking the binding of a parent signaling protein to at least one, or all, of its ligands; 2) signaling transduction activities, such as receptor dimerization, or tyrosine, serine and/or threonine phosphorylation; and 3) cellular responses induced by a parent signaling protein, such as oncogenic activities (e.g., cancer cell proliferation mediated by a parent signaling protein), and/or angiogenic activities.

In certain embodiments, the antibodies of the invention may have at least one activity selected from the group consisting of: 1) inhibiting cancer cell growth or proliferation; 2) inhibiting cancer cell survival; 3) inhibiting angiogenesis; 4) inhibiting cancer cell metastasis, adhesion, migration or invasion; 5) inducing apoptosis of cancer cells; 6) incorporating a toxic conjugate; and 7) acting as a diagnostic marker.

In certain embodiments, the phosphorylation site specific antibodies disclosed in the invention are especially indicated for diagnostic and therapeutic applications as described herein. Accordingly, the antibodies may be used in therapies, including combination therapies, in the diagnosis and prognosis of disease, as well as in the monitoring of disease progression. The invention, thus, further includes compositions comprising one or more embodiments of an antibody or an antigen binding portion of the invention as described herein. The composition may further comprise a pharmaceutically acceptable carrier. The composition may comprise two or more antibodies or antigen-binding portions, each with specificity for a different novel tyrosine, serine and/or threonine phosphorylation site of the invention or two or more different antibodies or antigen-binding portions all of which are specific for the same novel tyrosine, serine and/or threonine phosphorylation site of the invention. A composition of the invention may comprise one or more antibodies or antigen-binding portions of the invention and one or more additional reagents, diagnostic agents or therapeutic agents.

The present application provides for the polynucleotide molecules encoding the antibodies and antibody fragments and their analogs described herein. Because of the degeneracy of the genetic code, a variety of nucleic acid sequences encode each antibody amino acid sequence. The desired nucleic acid sequences can be produced by de novo solid-phase DNA synthesis or by PCR mutagenesis of an earlier prepared variant of the desired polynucleotide. In one embodiment, the codons that are used comprise those that are typical for human or mouse (see, e.g., Nakamura, Y., Nucleic Acids Res. 28: 292 (2000)).

The invention also provides immortalized cell lines that produce an antibody of the invention. For example, hybridoma clones, constructed as described above, that produce monoclonal antibodies to the targeted signaling protein phosphorylation sties disclosed herein are also provided. Similarly, the invention includes recombinant cells producing an antibody of the invention, which cells may be constructed by well known techniques; for example the antigen combining site of the monoclonal antibody can be cloned by PCR and single-chain antibodies produced as phage-displayed recombinant antibodies or soluble antibodies in $E.$ $coli$ (see, e.g., ANTIBODY ENGINEERING PROTOCOLS, 1995, Humana Press, Sudhir Paul editor.)

5. Methods of Making Phosphorylation Site-Specific Antibodies

In another aspect, the invention provides a method for making phosphorylation site-specific antibodies.

Polyclonal antibodies of the invention may be produced according to standard techniques by immunizing a suitable animal (e.g., rabbit, goat, etc.) with an antigen comprising a novel tyrosine, serine and/or threonine phosphorylation site of the invention. (i.e. a phosphorylation site shown in Table 1) in either the phosphorylated or unphosphorylated state, depending upon the desired specificity of the antibody, collecting immune serum from the animal, and separating the polyclonal antibodies from the immune serum, in accordance with known procedures and screening and isolating a polyclonal antibody specific for the novel tyrosine, serine and/or threonine phosphorylation site of interest as further described below. Methods for immunizing non-human animals such as mice, rats, sheep, goats, pigs, cattle and horses are well known in the art. See, e.g., Harlow and Lane, $Antibodies: A Laboratory Manual$, New York: Cold Spring Harbor Press, 1990.

The immunogen may be the full length protein or a peptide comprising the novel tyrosine, serine and/or threonine phosphorylation site of interest. In some embodiments the immunogen is a peptide of from 7 to 20 amino acids in length, preferably about 8 to 17 amino acids in length. In some embodiments, the peptide antigen desirably will comprise about 3 to 8 amino acids on each side of the phosphorylatable tyrosine, serine and/or threonine. In yet other embodiments, the peptide antigen desirably will comprise four or more amino acids flanking each side of the phosphorylatable amino acid and encompassing it. Peptide antigens suitable for producing antibodies of the invention may be designed, constructed and employed in accordance with well-known techniques. See, e.g., Antibodies: A Laboratory Manual, Chapter 5, p. 75-76, Harlow & Lane Eds., Cold Spring Harbor Laboratory (1988); Czernik, $Methods$ $In$ $Enzymology$, 201: 264-283 (1991); Merrifield, $J.$ $Am.$ $Chem.$ $Soc.$ 85: 21-49 (1962)).

Suitable peptide antigens may comprise all or partial sequence of a trypsin-digested fragment as set forth in Column E of Table 1/FIGS. 2A-2M. Suitable peptide antigens may also comprise all or partial sequence of a peptide fragment produced by another protease digestion.

Preferred immunogens are those that comprise a novel phosphorylation site of a protein in Table 1 that is an adaptor/scaffold protein, protein kinase, enzyme protein, ubiquitan conjugating system protein, chromatin or DNA binding/repair protein, g proteins or regulator protein, receptor/channel/transporter/cell surface protein, RNA binding protein, transcriptional regulator protein or an adhesion/extra-cellular matrix protein. In some embodiments, the peptide immunogen is an AQUA peptide, for example, any one of SEQ ID NOS: 1-155.

Particularly preferred immunogens are peptides comprising any one of the novel tyrosine, serine and/or threonine phosphorylation site shown as a lower case "y," "s" or "t" the sequences listed in Table 1 selected from the group consisting of SEQ ID NOS: 1 (AHNAK); 3 (RANBP9); 8 (TFG); 50 (CDK10); 51 (DCAMKL1); 52 (DCAMKL1); 53 (DCAMKL1); 34 (EZH2); 35 (EZH2); 36 (IARS); 17 (APRIN); 18 (APRIN); 19 (APRIN); 42 (RAB3IL1); 61 (ABCE1); 70 (PCBP1); 74 (ATF7); 75 (ATF7); 85 (RB1); 87 (SUPT5H); 88 (SUPT5H), 89 (YBX1); 90 (ZNFN1A1); 13 (CIAPIN1); 16 (ORC3L1); 25 (MAP1A); 26 (NDE1); 46

(INPP4A); 47 (HGFAC); 91 (EEF1G); 102 (C11orf2); 111 (C9orf30); 134 (LTV1); 154 (GOLGB1); and 155 (NISCH).

In some embodiments the immunogen is administered with an adjuvant. Suitable adjuvants will be well known to those of skill in the art. Exemplary adjuvants include complete or incomplete Freund's adjuvant, RIBI (muramyl dipeptides) or ISCOM (immunostimulating complexes).

For example, a peptide antigen comprising the novel receptor tyrosine kinase phosphorylation site in SEQ ID NO: 59 shown by the lower case "y" in Table 1 may be used to produce antibodies that specifically bind the novel tyrosine phosphorylation site.

When the above-described methods are used for producing polyclonal antibodies, following immunization, the polyclonal antibodies which secreted into the bloodstream can be recovered using known techniques. Purified forms of these antibodies can, of course, be readily prepared by standard purification techniques, such as for example, affinity chromatography with Protein A, anti-immunoglobulin, or the antigen itself. In any case, in order to monitor the success of immunization, the antibody levels with respect to the antigen in serum will be monitored using standard techniques such as ELISA, RIA and the like.

Monoclonal antibodies of the invention may be produced by any of a number of means that are well-known in the art. In some embodiments, antibody-producing B cells are isolated from an animal immunized with a peptide antigen as described above. The B cells may be from the spleen, lymph nodes or peripheral blood. Individual B cells are isolated and screened as described below to identify cells producing an antibody specific for the novel tyrosine, serine and/or threonine phosphorylation site of interest. Identified cells are then cultured to produce a monoclonal antibody of the invention.

Alternatively, a monoclonal phosphorylation site-specific antibody of the invention may be produced using standard hybridoma technology, in a hybridoma cell line according to the well-known technique of Kohler and Milstein. See *Nature* 265: 495-97 (1975); Kohler and Milstein, *Eur. J. Immunol.* 6: 511 (1976); see also, Current Protocols in Molecular Biology, Ausubel et al. Eds. (1989). Monoclonal antibodies so produced are highly specific, and improve the selectivity and specificity of diagnostic assay methods provided by the invention. For example, a solution containing the appropriate antigen may be injected into a mouse or other species and, after a sufficient time (in keeping with conventional techniques), the animal is sacrificed and spleen cells obtained. The spleen cells are then immortalized by any of a number of standard means. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. See, e.g., Harlow and Lane, supra. If fusion with myeloma cells is used, the myeloma cells preferably do not secrete immunoglobulin polypeptides (a non-secretory cell line). Typically the antibody producing cell and the immortalized cell (such as but not limited to myeloma cells) with which it is fused are from the same species. Rabbit fusion hybridomas, for example, may be produced as described in U.S. Pat. No. 5,675,063, C. Knight, Issued Oct. 7, 1997. The immortalized antibody producing cells, such as hybridoma cells, are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

The invention also encompasses antibody-producing cells and cell lines, such as hybridomas, as described above.

Polyclonal or monoclonal antibodies may also be obtained through in vitro immunization. For example, phage display techniques can be used to provide libraries containing a repertoire of antibodies with varying affinities for a particular antigen. Techniques for the identification of high affinity human antibodies from such libraries are described by Griffiths et al., (1994) *EMBO J.*, 13:3245-3260; Nissim et al., ibid, pp. 692-698 and by Griffiths et al., ibid, 12:725-734, which are incorporated by reference.

The antibodies may be produced recombinantly using methods well known in the art for example, according to the methods disclosed in U.S. Pat. No. 4,349,893 (Reading) or U.S. Pat. No. 4,816,567 (Cabilly et al.) The antibodies may also be chemically constructed by specific antibodies made according to the method disclosed in U.S. Pat. No. 4,676,980 (Segel et al.)

Once a desired phosphorylation site-specific antibody is identified, polynucleotides encoding the antibody, such as heavy, light chains or both (or single chains in the case of a single chain antibody) or portions thereof such as those encoding the variable region, may be cloned and isolated from antibody-producing cells using means that are well known in the art. For example, the antigen combining site of the monoclonal antibody can be cloned by PCR and single-chain antibodies produced as phage-displayed recombinant antibodies or soluble antibodies in *E. coli* (see, e.g., Antibody Engineering Protocols, 1995, Humana Press, Sudhir Paul editor.)

Accordingly, in a further aspect, the invention provides such nucleic acids encoding the heavy chain, the light chain, a variable region, a framework region or a CDR of an antibody of the invention. In some embodiments, the nucleic acids are operably linked to expression control sequences. The invention, thus, also provides vectors and expression control sequences useful for the recombinant expression of an antibody or antigen-binding portion thereof of the invention. Those of skill in the art will be able to choose vectors and expression systems that are suitable for the host cell in which the antibody or antigen-binding portion is to be expressed.

Monoclonal antibodies of the invention may be produced recombinantly by expressing the encoding nucleic acids in a suitable host cell under suitable conditions. Accordingly, the invention further provides host cells comprising the nucleic acids and vectors described above.

Monoclonal Fab fragments may also be produced in *Escherichia coli* by recombinant techniques known to those skilled in the art. See, e.g., W. Huse, *Science* 246: 1275-81 (1989); Mullinax et al., *Proc. Nat'l Acad. Sci.* 87: 8095 (1990).

If monoclonal antibodies of a single desired isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.,* 82: 8653 (1985); Spira et al., *J. Immunol. Methods,* 74: 307 (1984)). Alternatively, the isotype of a monoclonal antibody with desirable propertied can be changed using antibody engineering techniques that are well-known in the art.

Phosphorylation site-specific antibodies of the invention, whether polyclonal or monoclonal, may be screened for epitope and phospho-specificity according to standard techniques. See, e.g., Czernik et al., *Methods in Enzymology,* 201: 264-283 (1991). For example, the antibodies may be screened against the phosphorylated and/or unphosphorylated peptide library by ELISA to ensure specificity for both the desired antigen (i.e. that epitope including a phosphorylation site of the invention and for reactivity only with the phosphorylated (or unphosphorylated) form of the antigen. Peptide competition assays may be carried out to confirm lack of reactivity with other phospho-epitopes on the parent protein. The antibodies may also be tested by Western blotting against cell preparations containing the parent signaling protein, e.g., cell lines over-expressing the parent protein, to confirm reactivity with the desired phosphorylated epitope/target.

Specificity against the desired phosphorylated epitope may also be examined by constructing mutants lacking phosphorylatable residues at positions outside the desired epitope that are known to be phosphorylated, or by mutating the desired phospho-epitope and confirming lack of reactivity. Phosphorylation site-specific antibodies of the invention may exhibit some limited cross-reactivity to related epitopes in non-target proteins. This is not unexpected as most antibodies exhibit some degree of cross-reactivity, and anti-peptide antibodies will often cross-react with epitopes having high homology to the immunizing peptide. See, e.g., Czernik, supra. Cross-reactivity with non-target proteins is readily characterized by Western blotting alongside markers of known molecular weight. Amino acid sequences of cross-reacting proteins may be examined to identify phosphorylation sites with flanking sequences that are highly homologous to that of a phosphorylation site of the invention.

In certain cases, polyclonal antisera may exhibit some undesirable general cross-reactivity to phosphotyrosine, serine and/or threonine itself, which may be removed by further purification of antisera, e.g., over a phosphotyramine column. Antibodies of the invention specifically bind their target protein (i.e. a protein listed in Column A of Table 1) only when phosphorylated (or only when not phosphorylated, as the case may be) at the site disclosed in corresponding Columns D/E, and do not (substantially) bind to the other form (as compared to the form for which the antibody is specific).

Antibodies may be further characterized via immunohistochemical (IHC) staining using normal and diseased tissues to examine phosphorylation and activation state and level of a phosphorylation site in diseased tissue. IHC may be carried out according to well-known techniques. See, e.g., Antibodies: A Laboratory Manual, Chapter 10, Harlow & Lane Eds., Cold Spring Harbor Laboratory (1988). Briefly, paraffin-embedded tissue (e.g., tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antibodies may be further characterized by flow cytometry carried out according to standard methods. See Chow et al., *Cytometry (Communications in Clinical Cytometry)* 46: 72-78 (2001). Briefly and by way of example, the following protocol for cytometric analysis may be employed: samples may be centrifuged on Ficoll gradients to remove lysed erythrocytes and cell debris. Adhering cells may be scrapped off plates and washed with PBS. Cells may then be fixed with 2% paraformaldehyde for 10 minutes at 37° C. followed by permeabilization in 90% methanol for 30 minutes on ice. Cells may then be stained with the primary phosphorylation site-specific antibody of the invention (which detects a parent signaling protein enumerated in Table 1), washed and labeled with a fluorescent-labeled secondary antibody. Additional fluorochrome-conjugated marker antibodies (e.g., CD45, CD34) may also be added at this time to aid in the subsequent identification of specific hematopoietic cell types. The cells would then be analyzed on a flow cytometer (e.g. a Beckman Coulter FC500) according to the specific protocols of the instrument used.

Antibodies of the invention may also be advantageously conjugated to fluorescent dyes (e.g. Alexa488, PE) for use in multi-parametric analyses along with other signal transduction (phospho-CrkL, phospho-Erk ½) and/or cell marker (CD34) antibodies.

Phosphorylation site-specific antibodies of the invention may specifically bind to a signaling protein or polypeptide listed in Table 1 only when phosphorylated at the specified tyrosine, serine and/or threonine residue, but are not limited only to binding to the listed signaling proteins of human species, per se. The invention includes antibodies that also bind conserved and highly homologous or identical phosphorylation sites in respective signaling proteins from other species (e.g., mouse, rat, monkey, yeast), in addition to binding the phosphorylation site of the human homologue. The term "homologous" refers to two or more sequences or subsequences that have at least about 85%, at least 90%, at least 95%, or higher nucleotide or amino acid residue identity, when compared and aligned for maximum correspondence, as measured using sequence comparison method (e.g., BLAST) and/or by visual inspection. Highly homologous or identical sites conserved in other species can readily be identified by standard sequence comparisons (such as BLAST).

Methods for making bispecific antibodies are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Antibody variable domains with the desired binding specificities (antibody-antigen combining sites) can be fused to immunoglobulin constant domain sequences. In certain embodiments, the fusion is with an immunoglobulin heavy-chain constant domain, including at least part of the hinge, CH2, and CH3 regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, for example, Suresh et al., Methods in Enzymology, 121:210 (1986); WO 96/27011; Brennan et al., Science 229:81 (1985); Shalaby et al., J. Exp. Med. 175: 217-225 (1992); Kostelny et al., J. Immunol. 148(5):1547-1553 (1992); Hollinger et al., Proc. Natl. Acad. Sci. USA 90:6444-6448 (1993); Gruber et al., J. Immunol. 152:5368 (1994); and Tutt et al., J. Immunol. 147:60 (1991). Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. A strategy for making bispecific antibody fragments by the use of single-chain Fv (scFv) dimers has also been reported. See Gruber et al., J. Immunol., 152:5368 (1994). Alternatively, the antibodies can be "linear antibodies" as described in Zapata et al. Protein Eng. 8(10): 1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

To produce the chimeric antibodies, the portions derived from two different species (e.g., human constant region and murine variable or binding region) can be joined together chemically by conventional techniques or can be prepared as single contiguous proteins using genetic engineering techniques. The DNA molecules encoding the proteins of both the light chain and heavy chain portions of the chimeric antibody can be expressed as contiguous proteins. The method of making chimeric antibodies is disclosed in U.S. Pat. No. 5,677,427; U.S. Pat. No. 6,120,767; and U.S. Pat. No. 6,329,508, each of which is incorporated by reference in its entirety.

Fully human antibodies may be produced by a variety of techniques. One example is trioma methodology. The basic approach and an exemplary cell fusion partner, SPAZ-4, for use in this approach have been described by Oestberg et al., Hybridoma 2:361-367 (1983); Oestberg, U.S. Pat. No. 4,634,664; and Engleman et al., U.S. Pat. No. 4,634,666 (each of which is incorporated by reference in its entirety).

Human antibodies can also be produced from non-human transgenic animals having transgenes encoding at least a segment of the human immunoglobulin locus. The production and properties of animals having these properties are described in detail by, see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety.

Various recombinant antibody library technologies may also be utilized to produce fully human antibodies. For example, one approach is to screen a DNA library from human B cells according to the general protocol outlined by Huse et al., Science 246:1275-1281 (1989). The protocol described by Huse is rendered more efficient in combination with phage-display technology. See, e.g., Dower et al., WO 91/17271 and McCafferty et al., WO 92/01047; U.S. Pat. No. 5,969,108, (each of which is incorporated by reference in its entirety).

Eukaryotic ribosome can also be used as means to display a library of antibodies and isolate the binding human antibodies by screening against the target antigen, as described in Coia G, et al., J. Immunol. Methods 1: 254 (1-2):191-7 (2001); Hanes J. et al., Nat. Biotechnol. 18(12):1287-92 (2000); Proc. Natl. Acad. Sci. U.S.A. 95(24):14130-5 (1998); Proc. Natl. Acad. Sci. U. S. A. 94(10):4937-42 (1997), each which is incorporated by reference in its entirety.

The yeast system is also suitable for screening mammalian cell-surface or secreted proteins, such as antibodies. Antibody libraries may be displayed on the surface of yeast cells for the purpose of obtaining the human antibodies against a target antigen. This approach is described by Yeung, et al., Biotechnol. Prog. 18(2):212-20 (2002); Boeder, E. T., et al., Nat. Biotechnol. 15(6):553-7 (1997), each of which is herein incorporated by reference in its entirety. Alternatively, human antibody libraries may be expressed intracellularly and screened via the yeast two-hybrid system (WO0200729A2, which is incorporated by reference in its entirety).

Recombinant DNA techniques can be used to produce the recombinant phosphorylation site-specific antibodies described herein, as well as the chimeric or humanized phosphorylation site-specific antibodies, or any other genetically-altered antibodies and the fragments or conjugate thereof in any expression systems including both prokaryotic and eukaryotic expression systems, such as bacteria, yeast, insect cells, plant cells, mammalian cells (for example, NS0 cells).

Once produced, the whole antibodies, their dimers, individual light and heavy chains, or other immunoglobulin forms of the present application can be purified according to standard procedures of the art, including ammonium sulfate precipitation, affinity columns, column chromatography, gel electrophoresis and the like (see, generally, Scopes, R., Protein Purification (Springer-Verlag, N.Y., 1982)). Once purified, partially or to homogeneity as desired, the polypeptides may then be used therapeutically (including extracorporeally) or in developing and performing assay procedures, immunofluorescent staining, and the like. (See, generally, Immunological Methods, Vols. I and II (Lefkovits and Pernis, eds., Academic Press, NY, 1979 and 1981).

6. Therapeutic Uses

In a further aspect, the invention provides methods and compositions for therapeutic uses of the peptides or proteins comprising a phosphorylation site of the invention, and phosphorylation site-specific antibodies of the invention.

In one embodiment, the invention provides for a method of treating or preventing carcinoma in a subject, wherein the carcinoma is associated with the phosphorylation state of a novel phosphorylation site in Table 1, whether phosphorylated or dephosphorylated, comprising: administering to a subject in need thereof a therapeutically effective amount of a peptide comprising a novel phosphorylation site (Table 1) and/or an antibody or antigen-binding fragment thereof that specifically bind a novel phosphorylation site of the invention (Table 1). The antibodies maybe full-length antibodies, genetically engineered antibodies, antibody fragments, and antibody conjugates of the invention.

The term "subject" refers to a vertebrate, such as for example, a mammal, or a human. Although present application are primarily concerned with the treatment of human subjects, the disclosed methods may also be used for the treatment of other mammalian subjects such as dogs and cats for veterinary purposes.

In one aspect, the disclosure provides a method of treating carcinoma in which a peptide or an antibody that reduces at least one biological activity of a targeted signaling protein is administered to a subject. For example, the peptide or the antibody administered may disrupt or modulate the interaction of the target signaling protein with its ligand. Alternatively, the peptide or the antibody may interfere with, thereby reducing, the down-stream signal transduction of the parent signaling protein. An antibody that specifically binds the novel tyrosine, serine and/or threonine phosphorylation site only when the tyrosine, serine and/or threonine is phosphorylated, and that does not substantially bind to the same sequence when the tyrosine, serine and/or threonine is not phosphorylated, thereby prevents downstream signal transduction triggered by a phospho-tyrosine, serine and/or threonine. Alternatively, an antibody that specifically binds the unphosphorylated target phosphorylation site reduces the phosphorylation at that site and thus reduces activation of the protein mediated by phosphorylation of that site. Similarly, an unphosphorylated peptide may compete with an endogenous phosphorylation site for the same target (e.g., kinases), thereby preventing or reducing the phosphorylation of the endogenous target protein. Alternatively, a peptide comprising a phosphorylated novel tyrosine, serine and/or threonine site of the invention but lacking the ability to trigger signal transduction may competitively inhibit interaction of the endogenous protein with the same down-stream ligand(s).

The antibodies of the invention may also be used to target cancer cells for effector-mediated cell death. The antibody disclosed herein may be administered as a fusion molecule that includes a phosphorylation site-targeting portion joined to a cytotoxic moiety to directly kill cancer cells. Alternatively, the antibody may directly kill the cancer cells through complement-mediated or antibody-dependent cellular cytotoxicity.

Accordingly in one embodiment, the antibodies of the present disclosure may be used to deliver a variety of cytotoxic compounds. Any cytotoxic compound can be fused to the present antibodies. The fusion can be achieved chemically or genetically (e.g., via expression as a single, fused molecule). The cytotoxic compound can be a biological, such as a polypeptide, or a small molecule. As those skilled in the art will appreciate, for small molecules, chemical fusion is used, while for biological compounds, either chemical or genetic fusion can be used.

Non-limiting examples of cytotoxic compounds include therapeutic drugs, radiotherapeutic agents, ribosome-inactivating proteins (RIPs), chemotherapeutic agents, toxic peptides, toxic proteins, and mixtures thereof. The cytotoxic drugs can be intracellularly acting cytotoxic drugs, such as short-range radiation emitters, including, for example, short-range, high-energy α-emitters. Enzymatically active toxins and fragments thereof, including ribosome-inactivating proteins, are exemplified by saporin, luffin, momordins, ricin, trichosanthin, gelonin, abrin, etc. Procedures for preparing enzymatically active polypeptides of the immunotoxins are described in WO84/03508 and WO85/03508, which are hereby incorporated by reference. Certain cytotoxic moieties are derived from adriamycin, chlorambucil, daunomycin, methotrexate, neocarzinostatin, and platinum, for example.

Exemplary chemotherapeutic agents that may be attached to an antibody or antigen-binding fragment thereof include taxol, doxorubicin, verapamil, podophyllotoxin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, transplatinum, 5-fluorouracil, vincristin, vinblastin, or methotrexate.

Procedures for conjugating the antibodies with the cytotoxic agents have been previously described and are within the purview of one skilled in the art.

Alternatively, the antibody can be coupled to high energy radiation emitters, for example, a radioisotope, such as $^{131}$I, a γ-emitter, which, when localized at the tumor site, results in a killing of several cell diameters. See, e.g., S. E. Order, "Analysis, Results, and Future Prospective of the Therapeutic Use of Radiolabeled Antibody in Cancer Therapy", Monoclonal Antibodies for Cancer Detection and Therapy, Baldwin et al. (eds.), pp. 303-316 (Academic Press 1985), which is hereby incorporated by reference. Other suitable radioisotopes include α-emitters, such as $^{212}$Bi, $^{213}$Bi, and $^{211}$At, and β-emitters, such as $^{186}$Re and $^{90}$Y.

Because many of the signaling proteins in which novel tyrosine, serine and/or threonine phosphorylation sites of the invention occur also are expressed in normal cells and tissues, it may also be advantageous to administer a phosphorylation site-specific antibody with a constant region modified to reduce or eliminate ADCC or CDC to limit damage to normal cells. For example, effector function of an antibodies may be reduced or eliminated by utilizing an IgG1 constant domain instead of an IgG2/4 fusion domain. Other ways of eliminating effector function can be envisioned such as, e.g., mutation of the sites known to interact with FcR or insertion of a peptide in the hinge region, thereby eliminating critical sites required for FcR interaction. Variant antibodies with reduced or no effector function also include variants as described previously herein.

The peptides and antibodies of the invention may be used in combination with other therapies or with other agents. Other agents include but are not limited to polypeptides, small molecules, chemicals, metals, organometallic compounds, inorganic compounds, nucleic acid molecules, oligonucleotides, aptamers, spiegelmers, antisense nucleic acids, locked nucleic acid (LNA) inhibitors, peptide nucleic acid (PNA) inhibitors, immunomodulatory agents, antigen-binding fragments, prodrugs, and peptidomimetic compounds. In certain embodiments, the antibodies and peptides of the invention may be used in combination with cancer therapies known to one of skill in the art.

In certain aspects, the present disclosure relates to combination treatments comprising a phosphorylation site-specific antibody described herein and immunomodulatory compounds, vaccines or chemotherapy. Illustrative examples of suitable immunomodulatory agents that may be used in such combination therapies include agents that block negative regulation of T cells or antigen presenting cells (e.g., anti-CTLA4 antibodies, anti-PD-L1 antibodies, anti-PDL-2 antibodies, anti-PD-1 antibodies and the like) or agents that enhance positive co-stimulation of T cells (e.g., anti-CD40 antibodies or anti 4-1BB antibodies) or agents that increase NK cell number or T-cell activity (e.g., inhibitors such as IMiDs, thalidomide, or thalidomide analogs). Furthermore, immunomodulatory therapy could include cancer vaccines such as dendritic cells loaded with tumor cells, proteins, peptides, RNA, or DNA derived from such cells, patient derived heat-shock proteins (hsp's) or general adjuvants stimulating the immune system at various levels such as CpG, Luivac®, Biostim®, Ribomunyl®, Imudon®, Bronchovaxom® or any other compound or other adjuvant activating receptors of the innate immune system (e.g., toll like receptor agonist, anti-CTLA-4 antibodies, etc). Also, immunomodulatory therapy could include treatment with cytokines such as IL-2, GM-CSF and IFN-gamma.

Furthermore, combination of antibody therapy with chemotherapeutics could be particularly useful to reduce overall tumor burden, to limit angiogenesis, to enhance tumor accessibility, to enhance susceptibility to ADCC, to result in increased immune function by providing more tumor antigen, or to increase the expression of the T cell attractant LIGHT.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastimi, fludarabine, fludrocortisone, fluorouracil, fluoxymesterone, flutamide, gemcitabine, genistein, goserelin, hydroxyurea, idarubicin, ifosfamide, imatinib, interferon, irinotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into groups, including, for example, the following classes of agents: anti-metabolites/anti-cancer agents, such as pyrimidine analogs (5-fluorouracil, floxuridine, capecitabine, gemcitabine and cytarabine) and purine analogs, folate inhibitors and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristine, vinblastine, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, mechlorethamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); immunomodulatory agents (thalidomide and analogs thereof such as lenalidomide (Revlimid, CC-5013) and CC-4047 (Actimid)), cyclophosphamide; anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan); corticosteroids (cortisone, dexamethasone, hydrocortisone, methylprednisolone, prednisone, and prenisolone); growth factor signal transduction kinase inhibitors; mitochondrial dysfunction inducers and caspase activators; and chromatin disruptors.

In certain embodiments, pharmaceutical compounds that may be used for combinatory anti-angiogenesis therapy include: (1) inhibitors of release of "angiogenic molecules," such as bFGF (basic fibroblast growth factor); (2) neutralizers of angiogenic molecules, such as anti-βbFGF antibodies; and (3) inhibitors of endothelial cell response to angiogenic stimuli, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like. For additional proposed inhibitors of angiogenesis, see Blood et al., Biochim. Biophys. Acta, 1032:89-118 (1990), Moses et al., Science, 248:1408-1410 (1990), Ingber et al., Lab. Invest., 59:44-51 (1988), and U.S. Pat. Nos. 5,092,885, 5,112,946, 5,192,744, 5,202,352, and 6,573,256. In addition, there are a wide variety of compounds that can be used to inhibit angiogenesis, for example, peptides or agents that block the VEGF-mediated angiogenesis pathway, endostatin protein or derivatives, lysine binding fragments of angiostatin, melanin or melanin-promoting compounds, plasminogen fragments (e.g., Kringles 1-3 of plasminogen), troponin subunits, inhibitors of vitronectin $\alpha_v\beta_3$, peptides derived from Saposin B, antibiotics or analogs (e.g., tetracycline or neomycin), dienogest-containing compositions, compounds comprising a MetAP-2 inhibitory core coupled to a peptide, the compound EM-138, chalcone and its analogs, and naaladase inhibitors. See, for example, U.S. Pat. Nos. 6,395,718, 6,462,075, 6,465,431, 6,475,784, 6,482,802, 6,482,810, 6,500,431, 6,500,924, 6,518,298, 6,521,439, 6,525,019, 6,538,103, 6,544,758, 6,544,947, 6,548,477, 6,559,126, and 6,569,845.

7. Diagnostic Uses

In a further aspect, the invention provides methods for detecting and quantitating phosphorylation at a novel tyrosine, serine and/or threonine phosphorylation site of the invention. For example, peptides, including AQUA peptides of the invention, and antibodies of the invention are useful in diagnostic and prognostic evaluation of carcinomas, wherein the carcinoma is associated with the phosphorylation state of a novel phosphorylation site in Table 1, whether phosphorylated or dephosphorylated.

Methods of diagnosis can be performed in vitro using a biological sample (e.g., blood sample, lymph node biopsy or tissue) from a subject, or in vivo. The phosphorylation state or level at the tyrosine, serine and/or threonine residue identified in the corresponding row in Column D of Table 1 may be assessed. A change in the phosphorylation state or level at the phosphorylation site, as compared to a control, indicates that the subject is suffering from, or susceptible to, carcinoma.

In one embodiment, the phosphorylation state or level at a novel phosphorylation site is determined by an AQUA peptide comprising the phosphorylation site. The AQUA peptide may be phosphorylated or unphosphorylated at the specified tyrosine, serine and/or threonine position.

In another embodiment, the phosphorylation state or level at a phosphorylation site is determined by an antibody or antigen-binding fragment thereof, wherein the antibody specifically binds the phosphorylation site. The antibody may be one that only binds to the phosphorylation site when the tyrosine, serine and/or threonine residue is phosphorylated, but does not bind to the same sequence when the tyrosine, serine and/or threonine is not phosphorylated; or vice versa.

In particular embodiments, the antibodies of the present application are attached to labeling moieties, such as a detectable marker. One or more detectable labels can be attached to the antibodies. Exemplary labeling moieties include radiopaque dyes, radiocontrast agents, fluorescent molecules, spin-labeled molecules, enzymes, or other labeling moieties of diagnostic value, particularly in radiologic or magnetic resonance imaging techniques.

A radiolabeled antibody in accordance with this disclosure can be used for in vitro diagnostic tests. The specific activity of an antibody, binding portion thereof, probe, or ligand, depends upon the half-life, the isotopic purity of the radioactive label, and how the label is incorporated into the biological agent. In immunoassay tests, the higher the specific activity, in general, the better the sensitivity. Radioisotopes useful as labels, e.g., for use in diagnostics, include iodine ($^{131}$I or $^{125}$I), indium ($^{111}$In), technetium ($^{99}$Tc), phosphorus ($^{32}$P), carbon ($^{14}$C), and tritium ($^{3}$H), or one of the therapeutic isotopes listed above.

Fluorophore and chromophore labeled biological agents can be prepared from standard moieties known in the art. Since antibodies and other proteins absorb light having wavelengths up to about 310 nm, the fluorescent moieties may be selected to have substantial absorption at wavelengths above 310 nm, such as for example, above 400 nm. A variety of suitable fluorescers and chromophores are described by Stryer, Science, 162:526 (1968) and Brand et al., Annual Review of Biochemistry, 41:843-868 (1972), which are hereby incorporated by reference. The antibodies can be labeled with fluorescent chromophore groups by conventional procedures such as those disclosed in U.S. Pat. Nos. 3,940,475, 4,289,747, and 4,376,110, which are hereby incorporated by reference.

The control may be parallel samples providing a basis for comparison, for example, biological samples drawn from a healthy subject, or biological samples drawn from healthy tissues of the same subject. Alternatively, the control may be a pre-determined reference or threshold amount. If the subject is being treated with a therapeutic agent, and the progress of the treatment is monitored by detecting the tyrosine, serine and/or threonine phosphorylation state level at a phosphorylation site of the invention, a control may be derived from biological samples drawn from the subject prior to, or during the course of the treatment.

In certain embodiments, antibody conjugates for diagnostic use in the present application are intended for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. In certain embodiments, secondary binding ligands are biotin and avidin or streptavidin compounds.

Antibodies of the invention may also be optimized for use in a flow cytometry (FC) assay to determine the activation/phosphorylation status of a target signaling protein in subjects before, during, and after treatment with a therapeutic agent targeted at inhibiting tyrosine, serine and/or threonine phosphorylation at the phosphorylation site disclosed herein. For example, bone marrow cells or peripheral blood cells from patients may be analyzed by flow cytometry for target signaling protein phosphorylation, as well as for markers identifying various hematopoietic cell types. In this manner, activation status of the malignant cells may be specifically characterized. Flow cytometry may be carried out according to standard methods. See, e.g., Chow et al., *Cytometry (Communications in Clinical Cytometry)* 46: 72-78 (2001).

Alternatively, antibodies of the invention may be used in immunohistochemical (IHC) staining to detect differences in signal transduction or protein activity using normal and diseased tissues. IHC may be carried out according to well-known techniques. See, e.g., Antibodies: A Laboratory Manual, supra.

Peptides and antibodies of the invention may be also be optimized for use in other clinically-suitable applications, for example bead-based multiplex-type assays, such as IGEN, Luminex™ and/or Bioplex™ assay formats, or otherwise optimized for antibody arrays formats, such as reversed-phase array applications (see, e.g. Paweletz et al., *Oncogene* 20(16): 1981-89 (2001)). Accordingly, in another embodiment, the invention provides a method for the multiplex detection of the phosphorylation state or level at two or more phosphorylation sites of the invention (Table 1) in a biological sample, the method comprising utilizing two or more antibodies or AQUA peptides of the invention. In one preferred embodiment, two to five antibodies or AQUA peptides of the invention are used. In another preferred embodiment, six to ten antibodies or AQUA peptides of the invention are used, while in another preferred embodiment eleven to twenty antibodies or AQUA peptides of the invention are used.

In certain embodiments the diagnostic methods of the application may be used in combination with other cancer diagnostic tests.

The biological sample analyzed may be any sample that is suspected of having abnormal tyrosine, serine and/or threonine phosphorylation at a novel phosphorylation site of the invention, such as a homogenized neoplastic tissue sample.

8. Screening Assays

In another aspect, the invention provides a method for identifying an agent that modulates tyrosine, serine and/or threonine phosphorylation at a novel phosphorylation site of the invention, comprising: a) contacting a candidate agent with a peptide or protein comprising a novel phosphorylation site of the invention; and b) determining the phosphorylation state or level at the novel phosphorylation site. A change in the phosphorylation level of the specified tyrosine, serine and/or threonine in the presence of the test agent, as compared to a control, indicates that the candidate agent potentially modulates tyrosine, serine and/or threonine phosphorylation at a novel phosphorylation site of the invention.

In one embodiment, the phosphorylation state or level at a novel phosphorylation site is determined by an AQUA peptide comprising the phosphorylation site. The AQUA peptide may be phosphorylated or unphosphorylated at the specified tyrosine, serine and/or threonine position.

In another embodiment, the phosphorylation state or level at a phosphorylation site is determined by an antibody or antigen-binding fragment thereof, wherein the antibody specifically binds the phosphorylation site. The antibody may be one that only binds to the phosphorylation site when the tyrosine, serine and/or threonine residue is phosphorylated, but does not bind to the same sequence when the tyrosine, serine and/or threonine is not phosphorylated; or vice versa.

In particular embodiments, the antibodies of the present application are attached to labeling moieties, such as a detectable marker.

The control may be parallel samples providing a basis for comparison, for example, the phosphorylation level of the target protein or peptide in absence of the testing agent. Alternatively, the control may be a pre-determined reference or threshold amount.

9. Immunoassays

In another aspect, the present application concerns immunoassays for binding, purifying, quantifying and otherwise generally detecting the phosphorylation state or level at a novel phosphorylation site of the invention.

Assays may be homogeneous assays or heterogeneous assays. In a homogeneous assay the immunological reaction usually involves a phosphorylation site-specific antibody of the invention, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels that may be used include free radicals, radioisotopes, fluorescent dyes, enzymes, bacteriophages, coenzymes, and so forth.

In a heterogeneous assay approach, the reagents are usually the specimen, a phosphorylation site-specific antibody of the invention, and suitable means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal using means for producing such signal. The signal is related to the presence of the analyte in the specimen. Means for producing a detectable signal include the use of radioactive labels, fluorescent labels, enzyme labels, and so forth.

Phosphorylation site-specific antibodies disclosed herein may be conjugated to a solid support suitable for a diagnostic assay (e.g., beads, plates, slides or wells formed from materials such as latex or polystyrene) in accordance with known techniques, such as precipitation.

In certain embodiments, immunoassays are the various types of enzyme linked immunoabsorbent assays (ELISAs) and radioimmunoassays (RIA) known in the art. Immunohistochemical detection using tissue sections is also particularly useful. However, it will be readily appreciated that detection is not limited to such techniques, and Western blotting, dot and slot blotting, FACS analyses, and the like may also be used. The steps of various useful immunoassays have been described in the scientific literature, such as, e.g., Nakamura et al., in Enzyme Immunoassays: Heterogeneous and Homogeneous Systems, Chapter 27 (1987), incorporated herein by reference.

In general, the detection of immunocomplex formation is well known in the art and may be achieved through the application of numerous approaches. These methods are based upon the detection of radioactive, fluorescent, biological or enzymatic tags. Of course, one may find additional advantages through the use of a secondary binding ligand such as a second antibody or a biotin/avidin ligand binding arrangement, as is known in the art.

The antibody used in the detection may itself be conjugated to a detectable label, wherein one would then simply detect this label. The amount of the primary immune complexes in the composition would, thereby, be determined.

Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are washed extensively to remove any non-specifically bound labeled secondary antibodies or ligands, and the remaining label in the secondary immune complex is detected.

An enzyme linked immunoabsorbent assay (ELISA) is a type of binding assay. In one type of ELISA, phosphorylation site-specific antibodies disclosed herein are immobilized onto a selected surface exhibiting protein affinity, such as a well in a polystyrene microtiter plate. Then, a suspected neoplastic tissue sample is added to the wells. After binding and washing to remove non-specifically bound immune complexes, the bound target signaling protein may be detected.

In another type of ELISA, the neoplastic tissue samples are immobilized onto the well surface and then contacted with the phosphorylation site-specific antibodies disclosed herein. After binding and washing to remove non-specifically bound immune complexes, the bound phosphorylation site-specific antibodies are detected.

Irrespective of the format used, ELISAs have certain features in common, such as coating, incubating or binding, washing to remove non-specifically bound species, and detecting the bound immune complexes.

The radioimmunoassay (RIA) is an analytical technique which depends on the competition (affinity) of an antigen for antigen-binding sites on antibody molecules. Standard curves are constructed from data gathered from a series of samples each containing the same known concentration of labeled antigen, and various, but known, concentrations of unlabeled antigen. Antigens are labeled with a radioactive isotope tracer. The mixture is incubated in contact with an antibody. Then the free antigen is separated from the antibody and the antigen bound thereto. Then, by use of a suitable detector, such as a gamma or beta radiation detector, the percent of either the bound or free labeled antigen or both is determined. This procedure is repeated for a number of samples containing various known concentrations of unlabeled antigens and the results are plotted as a standard graph. The percent of bound tracer antigens is plotted as a function of the antigen concentration. Typically, as the total antigen concentration increases the relative amount of the tracer antigen bound to the antibody decreases. After the standard graph is prepared, it is thereafter used to determine the concentration of antigen in samples undergoing analysis.

In an analysis, the sample in which the concentration of antigen is to be determined is mixed with a known amount of tracer antigen. Tracer antigen is the same antigen known to be in the sample but which has been labeled with a suitable radioactive isotope. The sample with tracer is then incubated in contact with the antibody. Then it can be counted in a suitable detector which counts the free antigen remaining in the sample. The antigen bound to the antibody or immunoabsorbent may also be similarly counted. Then, from the standard curve, the concentration of antigen in the original sample is determined.

10. Pharmaceutical Formulations and Methods of Administration

Methods of administration of therapeutic agents, particularly peptide and antibody therapeutics, are well-known to those of skill in the art.

Peptides of the invention can be administered in the same manner as conventional peptide type pharmaceuticals. Preferably, peptides are administered parenterally, for example, intravenously, intramuscularly, intraperitoneally, or subcutaneously. When administered orally, peptides may be proteolytically hydrolyzed. Therefore, oral application may not be usually effective. However, peptides can be administered orally as a formulation wherein peptides are not easily hydrolyzed in a digestive tract, such as liposome-microcapsules. Peptides may be also administered in suppositories, sublingual tablets, or intranasal spray.

If administered parenterally, a preferred pharmaceutical composition is an aqueous solution that, in addition to a peptide of the invention as an active ingredient, may contain for example, buffers such as phosphate, acetate, etc., osmotic pressure-adjusting agents such as sodium chloride, sucrose, and sorbitol, etc., antioxidative or antioxygenic agents, such as ascorbic acid or tocopherol and preservatives, such as antibiotics. The parenterally administered composition also may be a solution readily usable or in a lyophilized form which is dissolved in sterile water before administration.

The pharmaceutical formulations, dosage forms, and uses described below generally apply to antibody-based therapeutic agents, but are also useful and can be modified, where necessary, for making and using therapeutic agents of the disclosure that are not antibodies.

To achieve the desired therapeutic effect, the phosphorylation site-specific antibodies or antigen-binding fragments thereof can be administered in a variety of unit dosage forms. The dose will vary according to the particular antibody. For example, different antibodies may have different masses and/or affinities, and thus require different dosage levels. Antibodies prepared as Fab or other fragments will also require differing dosages than the equivalent intact immunoglobulins, as they are of considerably smaller mass than intact immunoglobulins, and thus require lower dosages to reach the same molar levels in the patient's blood. The dose will also vary depending on the manner of administration, the particular symptoms of the patient being treated, the overall health, condition, size, and age of the patient, and the judgment of the prescribing physician. Dosage levels of the antibodies for human subjects are generally between about 1 mg per kg and about 100 mg per kg per patient per treatment, such as for example, between about 5 mg per kg and about 50 mg per kg per patient per treatment. In terms of plasma concentrations, the antibody concentrations may be in the range from about 25 μg/mL to about 500 μg/mL. However, greater amounts may be required for extreme cases and smaller amounts may be sufficient for milder cases.

Administration of an antibody will generally be performed by a parenteral route, typically via injection such as intra-articular or intravascular injection (e.g., intravenous infusion) or intramuscular injection. Other routes of administration, e.g., oral (p.o.), may be used if desired and practicable for the particular antibody to be administered. An antibody can also be administered in a variety of unit dosage forms and their dosages will also vary with the size, potency, and in vivo half-life of the particular antibody being administered. Doses of a phosphorylation site-specific antibody will also vary depending on the manner of administration, the particular symptoms of the patient being treated, the overall health, condition, size, and age of the patient, and the judgment of the prescribing physician.

The frequency of administration may also be adjusted according to various parameters. These include the clinical response, the plasma half-life of the antibody, and the levels of the antibody in a body fluid, such as, blood, plasma, serum, or synovial fluid. To guide adjustment of the frequency of administration, levels of the antibody in the body fluid may be monitored during the course of treatment.

Formulations particularly useful for antibody-based therapeutic agents are also described in U.S. Patent App. Publication Nos. 20030202972, 20040091490 and 20050158316. In certain embodiments, the liquid formulations of the application are substantially free of surfactant and/or inorganic salts. In another specific embodiment, the liquid formulations have a pH ranging from about 5.0 to about 7.0. In yet another specific embodiment, the liquid formulations comprise histidine at a concentration ranging from about 1 mM to about 100 mM. In still another specific embodiment, the liquid formulations comprise histidine at a concentration ranging from 1 mM to 100 mM. It is also contemplated that the liquid formulations may further comprise one or more excipients such as a saccharide, an amino acid (e.g., arginine, lysine, and methionine) and a polyol. Additional descriptions and methods of preparing and analyzing liquid formulations can be found, for example, in PCT publications WO 03/106644, WO 04/066957, and WO 04/091658.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the pharmaceutical compositions of the application.

In certain embodiments, formulations of the subject antibodies are pyrogen-free formulations which are substantially free of endotoxins and/or related pyrogenic substances. Endotoxins include toxins that are confined inside microorganisms and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with monoclonal antibodies, it is advantageous to remove even trace amounts of endotoxin.

The amount of the formulation which will be therapeutically effective can be determined by standard clinical techniques. In addition, in vitro assays may optionally be used to help identify optimal dosage ranges. The precise dose to be used in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. The dosage of the compositions to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. For example, the actual patient body weight may be used to calculate the dose of the formulations in milliliters (mL) to be administered. There may be no downward adjustment to "ideal" weight. In such a situation, an appropriate dose may be calculated by the following formula:

$$\text{Dose(mL)} = [\text{patient weight(kg)} \times \text{dose level(mg/kg)} / \text{drug concentration(mg/mL)}]$$

For the purpose of treatment of disease, the appropriate dosage of the compounds (for example, antibodies) will depend on the severity and course of disease, the patient's clinical history and response, the toxicity of the antibodies, and the discretion of the attending physician. The initial candidate dosage may be administered to a patient. The proper dosage and treatment regimen can be established by monitoring the progress of therapy using conventional techniques known to those of skill in the art.

The formulations of the application can be distributed as articles of manufacture comprising packaging material and a pharmaceutical agent which comprises, e.g., the antibody and a pharmaceutically acceptable carrier as appropriate to the mode of administration. The packaging material will include a label which indicates that the formulation is for use in the treatment of prostate cancer.

11. Kits

Antibodies and peptides (including AQUA peptides) of the invention may also be used within a kit for detecting the phosphorylation state or level at a novel phosphorylation site of the invention, comprising at least one of the following: an AQUA peptide comprising the phosphorylation site, or an antibody or an antigen-binding fragment thereof that binds to an amino acid sequence comprising the phosphorylation site. Such a kit may further comprise a packaged combination of reagents in predetermined amounts with instructions for performing the diagnostic assay. Where the antibody is labeled with an enzyme, the kit will include substrates and co-factors required by the enzyme. In addition, other additives may be included such as stabilizers, buffers and the like. The relative amounts of the various reagents may be varied widely to provide for concentrations in solution of the reagents that substantially optimize the sensitivity of the assay. Particularly, the reagents may be provided as dry powders, usually lyophilized, including excipients that, on dissolution, will provide a reagent solution having the appropriate concentration.

The following Examples are provided only to further illustrate the invention, and are not intended to limit its scope, except as provided in the claims appended hereto. The invention encompasses modifications and variations of the methods taught herein which would be obvious to one of ordinary skill in the art.

EXAMPLE 1

Isolation of Phospho-Tyrosine, Phospho-Serine and Phospho-Threonine Containing Peptides from Extracts of Carcinoma and Leukemia Cell Lines and Tissues and Identification of Novel Phosphorylation Sites In order to discover novel tyrosine, serine and/or threonine phosphorylation sites in carcinoma, IAP isolation techniques were used to identify phosphotyrosine, serine and/or threonine-containing peptides in cell extracts from human carcinoma cell lines and patient cell lines identified in Column G of Table 1 including HeLa, Jurkat, K562, DMS 153, H69 (xenograft), HT29, M01043, H526, DMS 53, DMS 79, and MEC-1 Tryptic phosphotyrosine, serine and/or threonine-containing peptides were purified and analyzed from extracts of each of the cell lines mentioned above, as follows. Cells were cultured in DMEM medium or RPMI 1640 medium supplemented with 10% fetal bovine serum and penicillin/streptomycin.

Suspension cells were harvested by low speed centrifugation. After complete aspiration of medium, cells were resuspended in 1 mL lysis buffer per $1.25 \times 10^8$ cells (20 mM HEPES pH 8.0, 9 M urea, 1 mM sodium vanadate, supplemented or not with 2.5 mM sodium pyro-phosphate, 1 mM β-glycerol-phosphate) and sonicated.

Adherent cells at about 80% confluency were starved in medium without serum overnight and stimulated, with ligand depending on the cell type or not stimulated. After complete aspiration of medium from the plates, cells were scraped off the plate in 10 ml lysis buffer per $2 \times 10^8$ cells (20 mM HEPES pH 8.0, 9 M urea, 1 mM sodium vanadate, supplemented with 2.5 mM sodium pyrophosphate, 1 mM β-glycerol-phosphate) and sonicated.

Frozen tissue samples were cut to small pieces, homogenize in lysis buffer (20 mM HEPES pH 8.0, 9 M Urea, 1 mN sodium vanadate, supplemented with 2.5 mM sodium pyrophosphate, 1 mM b-glycerol-phosphate, 1 ml lysis buffer for 100 mg of frozen tissue) using a polytron for 2 times of 20 sec. each time. Homogenate is then briefly sonicated.

Sonicated cell lysates were cleared by centrifugation at 20,000×g, and proteins were reduced with DTT at a final concentration of 4.1 mM and alkylated with iodoacetamide at 8.3 mM. For digestion with trypsin, protein extracts were diluted in 20 mM HEPES pH 8.0 to a final concentration of 2 M urea and soluble TLCK-trypsin (Worthington) was added at 10-20 µg/mL. Digestion was performed for 1-2 days at room temperature.

Trifluoroacetic acid (TFA) was added to protein digests to a final concentration of 1%, precipitate was removed by centrifugation, and digests were loaded onto Sep-Pak $C_{18}$ columns (Waters) equilibrated with 0.1% TFA. A column volume of 0.7-1.0 ml was used per $2 \times 10^8$ cells. Columns were washed with 15 volumes of 0.1% TFA, followed by 4 volumes of 5% acetonitrile (MeCN) in 0.1% TFA. Peptide fraction I was obtained by eluting columns with 2 volumes each of 8, 12, and 15% MeCN in 0.1% TFA and combining the eluates. Fractions II and III were a combination of eluates after eluting columns with 18, 22, 25% MeCN in 0.1% TFA and with 30, 35, 40% MeCN in 0.1% TFA, respectively. All peptide fractions were lyophilized.

Peptides from each fraction corresponding to $2 \times 10^8$ cells were dissolved in 1 ml of IAP buffer (20 mM Tris/HCl or 50 mM MOPS pH 7.2, 10 mM sodium phosphate, 50 mM NaCl) and insoluble matter (mainly in peptide fractions III) was removed by centrifugation. IAP was performed on each peptide fraction separately. The phosphotyrosine, serine and/or threonine monoclonal antibody P-Tyr-100 (Cell Signaling Technology, Inc., catalog number 9411) was coupled at 4 mg/ml beads to protein G (Roche), respectively. Immobilized antibody (15 µl, 60 µg) was added as 1:1 slurry in IAP buffer to 1 ml of each peptide fraction, and the mixture was incubated overnight at 4° C. with gentle rotation. The immobilized antibody beads were washed three times with 1 ml IAP buffer and twice with 1 ml water, all at 4° C. Peptides were eluted from beads by incubation with 75 µl of 0.1% TFA at room temperature for 10 minutes.

Alternatively, one single peptide fraction was obtained from Sep-Pak C18 columns by elution with 2 volumes each of 10%, 15%, 20%, 25%, 30%, 35% and 40% acetonitrile in 0.1% TFA and combination of all eluates. IAP on this peptide fraction was performed as follows: After lyophilization, peptide was dissolved in 1.4 ml IAP buffer (MOPS pH 7.2, 10 mM sodium phosphate, 50 mM NaCl) and insoluble matter was removed by centrifugation. Immobilized antibody (40 µl, 160 µg) was added as 1:1 slurry in IAP buffer, and the mixture was incubated overnight at 4° C. with gentle shaking. The immobilized antibody beads were washed three times with 1 ml IAP buffer and twice with 1 ml water, all at 4° C. Peptides were eluted from beads by incubation with 55 µl of 0.15% TFA at room temperature for 10 min (eluate 1), followed by a wash of the beads (eluate 2) with 45 µl of 0.15% TFA. Both eluates were combined.

Analysis by LC-MS/MS Mass Spectrometry.

40 µl or more of IAP eluate were purified by 0.2 µl StageTips or ZipTips. Peptides were eluted from the microcolumns with 1 µl of 40% MeCN, 0.1% TFA (fractions I and II) or 1 µl of 60% MeCN, 0.1% TFA (fraction III) into 7.6-9.0 µl of 0.4% acetic acid/0.005% heptafluorobutyric acid. For single fraction analysis, 1 µl of 60% MeCN, 0.1% TFA, was used for elution from the microcolumns. This sample was loaded onto a 10 cm×75 µm PicoFrit capillary column (New Objective) packed with Magic C18 AQ reversed-phase resin (Michrom Bioresources) using a Famos autosampler with an inert sample injection valve (Dionex). The column was then developed with a 45-min linear gradient of acetonitrile delivered at 200 nl/min (Ultimate, Dionex), and tandem mass spectra were collected in a data-dependent manner with an LTQ ion trap mass spectrometer essentially as described by Gygi et al., supra.

Database Analysis & Assignments.

MS/MS spectra were evaluated using TurboSequest in the Sequest Browser package (v. 27, rev. 12) supplied as part of BioWorks 3.0 (ThermoFinnigan). Individual MS/MS spectra were extracted from the raw data file using the Sequest Browser program CreateDta, with the following settings: bottom MW, 700; top MW, 4,500; minimum number of ions, 20 (40 for LTQ); minimum TIC, $4 \times 10^5 (2 \times 10^3$ for LTQ); and precursor charge state, unspecified. Spectra were extracted from the beginning of the raw data file before sample injection to the end of the eluting gradient. The IonQuest and VuDta programs were not used to further select MS/MS spectra for Sequest analysis. MS/MS spectra were evaluated with the following TurboSequest parameters: peptide mass tolerance, 2.5; fragment ion tolerance, 0.0 (1.0 for LTQ); maximum number of differential amino acids per modification, 4; mass type parent, average; mass type fragment, average; maximum number of internal cleavage sites, 10; neutral losses of water and ammonia from b and y ions were considered in the correlation analysis. Proteolytic enzyme was specified except for spectra collected from elastase digests.

Searches were performed against the NCBI human protein database (NCBI RefSeq protein release #11; 8 May 2005; 1,826,611 proteins, including 47,859 human proteins. Peptides that did not match RefSeq were compared to NCBI GenPept release #148; 15 Jun. 2005 release date; 2,479,172 proteins, including 196,054 human proteins). Cysteine carboxamidomethylation was specified as a static modification, and phosphorylation was allowed as a variable modification on tyrosine, serine and/or threonine residues. It was determined that restricting phosphorylation to tyrosine, serine and/ or threonine residues had little effect on the number of phosphorylation sites assigned.

In proteomics research, it is desirable to validate protein identifications based solely on the observation of a single peptide in one experimental result, in order to indicate that the protein is, in fact, present in a sample. This has led to the development of statistical methods for validating peptide assignments, which are not yet universally accepted, and guidelines for the publication of protein and peptide identification results (see Can et al., *Mol. Cell Proteomics* 3: 531-533 (2004)), which were followed in this Example. However, because the immunoaffinity strategy separates phosphorylated peptides from unphosphorylated peptides, observing just one phosphopeptide from a protein is a common result, since many phosphorylated proteins have only one tyrosine, serine and/or threonine-phosphorylated site. For this reason, it is appropriate to use additional criteria to validate phosphopeptide assignments. Assignments are likely to be correct if any of these additional criteria are met: (i) the same phosphopeptide sequence is assigned to co-eluting ions with different charge states, since the MS/MS spectrum changes markedly with charge state; (ii) the phosphorylation site is found in more than one peptide sequence context due to sequence overlaps from incomplete proteolysis or use of proteases other than trypsin; (iii) the phosphorylation site is found in more than one peptide sequence context due to homologous but not identical protein isoforms; (iv) the phosphorylation site is found in more than one peptide sequence context due to homologous but not identical proteins among species; and (v) phosphorylation sites validated by MS/MS analysis of synthetic phosphopeptides corresponding to assigned sequences, since the ion trap mass spectrometer produces highly reproducible MS/MS spectra. The last criterion is routinely used to confirm novel site assignments of particular interest.

All spectra and all sequence assignments made by Sequest were imported into a relational database. The following Sequest scoring thresholds were used to select phosphopeptide assignments that are likely to be correct: RSp<6, XCorr≥2.2, and DeltaCN>0.099. Further, the sequence assignments could be accepted or rejected with respect to accuracy by using the following conservative, two-step process.

In the first step, a subset of high-scoring sequence assignments should be selected by filtering for XCorr values of at least 1.5 for a charge state of +1, 2.2 for +2, and 3.3 for +3, allowing a maximum RSp value of 10. Assignments in this subset should be rejected if any of the following criteria are satisfied: (i) the spectrum contains at least one major peak (at least 10% as intense as the most intense ion in the spectrum) that can not be mapped to the assigned sequence as an a, b, or y ion, as an ion arising from neutral-loss of water or ammonia from a b or y ion, or as a multiply protonated ion; (ii) the spectrum does not contain a series of b or y ions equivalent to at least six uninterrupted residues; or (iii) the sequence is not observed at least five times in all the studies conducted (except for overlapping sequences due to incomplete proteolysis or use of proteases other than trypsin).

In the second step, assignments with below-threshold scores should be accepted if the low-scoring spectrum shows a high degree of similarity to a high-scoring spectrum collected in another study, which simulates a true reference library-searching strategy.

EXAMPLE 2

Production of Phosphorylation Site-Specific Polyclonal Antibodies

Polyclonal antibodies that specifically bind a novel phosphorylation site of the invention (Table 1/FIGS. 2A-2M) only when the tyrosine, serine and/or threonine residue is phosphorylated (and does not bind to the same sequence when the tyrosine, serine and/or threonine is not phosphorylated), and vice versa, are produced according to standard methods by first constructing a synthetic peptide antigen comprising the phosphorylation site and then immunizing an animal to raise antibodies against the antigen, as further described below. Production of exemplary polyclonal antibodies is provided below.

A. TFG (Tyrosine 392).

A 17 amino acid phospho-peptide antigen, NRPPFGQGy*TQPGPGYR (SEQ NO:8; y*=phosphotyrosine), which comprises the phosphorylation site derived from human TFG (an adaptor/scaffold protein, Tyr 392 being the phosphorylatable residue), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phosphorylation site-specific polyclonal antibodies as described in Immunization/Screening below.

B. MLLT4 (Tyrosine 1269).

A 15 amino acid phospho-peptide antigen, SQEELREDKAy*QLER (SEQ NO:11; y*=phosphotyrosine), which comprises the phosphorylation site derived from human MLLT4 (an adhesion or extracellular matrix protein, Tyr 1269 being the phosphorylatable residue), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phosphorylation site-specific polyclonal antibodies as described in Immunization/Screening below.

C. CIAPIN1 (Tyrosine 290).

A 17 amino acid phospho-peptide antigen, CASCPy*LGMPAFKPGEK (SEQ NO:13; y*=phosphotyrosine), which comprises the phosphorylation site derived from human CIAPIN1 (an apoptosis protein, Tyr 290 being the phosphorylatable residue), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phosphorylation site-specific polyclonal antibodies as described in Immunization/Screening below.

Immunization/Screening.

A synthetic phospho-peptide antigen as described in A-C above is coupled to KLH, and rabbits are injected intradermally (ID) on the back with antigen in complete Freunds adjuvant (500 µg antigen per rabbit). The rabbits are boosted with same antigen in incomplete Freund adjuvant (250 µg antigen per rabbit) every three weeks. After the fifth boost, bleeds are collected. The sera are purified by Protein A-affinity chromatography by standard methods (see ANTIBODIES: A LABORATORY MANUAL, Cold Spring Harbor, supra). The eluted immunoglobulins are further loaded onto an unphosphorylated synthetic peptide antigen-resin Knotes column to pull out antibodies that bind the unphosphorylated form of the phosphorylation sites. The flow through fraction is collected and applied onto a phospho-synthetic peptide antigen—resin column to isolate antibodies that bind the phosphorylated form of the phosphorylation sites. After washing the column extensively, the bound antibodies (i.e. antibodies that bind the phosphorylated peptides described in A-C above, but do not bind the unphosphorylated form of the peptides) are eluted and kept in antibody storage buffer.

The isolated antibody is then tested for phospho-specificity using Western blot assay using an appropriate cell line that expresses (or overexpresses) target phospho-protein (i.e. phosphorylated MLLT4, TFG or CIAPIN1), found in, for example, Jurkat cells. Cells are cultured in DMEM or RPMI supplemented with 10% FCS. Cell are collected, washed with PBS and directly lysed in cell lysis buffer. The protein concentration of cell lysates is then measured. The loading buffer is added into cell lysate and the mixture is boiled at 100° C. for 5 minutes. 20 µl (10 µg protein) of sample is then added onto 7.5% SDS-PAGE gel.

A standard Western blot may be performed according to the Immunoblotting Protocol set out in the CELL SIGNALING TECHNOLOGY, INC. 2003-04 Catalogue, p. 390. The isolated phosphorylation site-specific antibody is used at dilution 1:1000. Phospho-specificity of the antibody will be shown by binding of only the phosphorylated form of the target amino acid sequence. Isolated phosphorylation site-specific polyclonal antibody does not (substantially) recognize the same target sequence when not phosphorylated at the specified tyrosine, serine and/or threonine position (e.g., the antibody does not bind to CIAPIN1 in the non-stimulated cells, when tyrosine 290 is not phosphorylated).

In order to confirm the specificity of the isolated antibody, different cell lysates containing various phosphorylated signaling proteins other than the target protein are prepared. The Western blot assay is performed again using these cell lysates. The phosphorylation site-specific polyclonal antibody isolated as described above is used (1:1000 dilution) to test reactivity with the different phosphorylated non-target proteins. The phosphorylation site-specific antibody does not significantly cross-react with other phosphorylated signaling proteins that do not have the described phosphorylation site, although occasionally slight binding to a highly homologous sequence on another protein may be observed. In such case the antibody may be further purified using affinity chromatography, or the specific immunoreactivity cloned by rabbit hybridoma technology.

EXAMPLE 3

Production of Phosphorylation Site-Specific Monoclonal Antibodies

Monoclonal antibodies that specifically bind a novel phosphorylation site of the invention (Table 1) only when the tyrosine, serine and/or threonine residue is phosphorylated (and does not bind to the same sequence when the tyrosine, serine and/or threonine is not phosphorylated) are produced according to standard methods by first constructing a synthetic peptide antigen comprising the phosphorylation site and then immunizing an animal to raise antibodies against the antigen, and harvesting spleen cells from such animals to produce fusion hybridomas, as further described below. Production of exemplary monoclonal antibodies is provided below.

A. ORC3L (Tyrosine 527).

A 8 amino acid phospho-peptide antigen, TDLy*HLQK (SEQ ID NO: 16; y*=phosphotyrosine), which comprises the phosphorylation site derived from human ORC3L (a cell cycle regulation protein, Tyr 527 being the phosphorylatable residue), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phosphorylation site-specific monoclonal antibodies as described in Immunization/Fusion/Screening below.

B. NDE1 (Threonine 246).

A 16 amino acid phospho-peptide antigen, GLDDSTGGTPLt*PAAR (SEQ ID NO: 26; t*=phosphothreonine), which comprises the phosphorylation site derived from human NDE1 (a cytoskeletal protein, Thr 246 being the phosphorylatable residue), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phosphorylation site-specific monoclonal antibodies as described in Immunization/Fusion/Screening below
C. KIF1C (Serine 1026).

An 11 amino acid phospho-peptide antigen, RPPSRRs*HHPR (SEQ ID NO: 16; s*=phosphoserine), which comprises the phosphorylation site derived from human KIF1C (an endoplasmic reticulum or golgi protein, Ser 1026 being the phosphorylatable residue), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phosphorylation site-specific monoclonal antibodies as described in Immunization/Fusion/Screening below Immunization/Fusion/Screening.

A synthetic phospho-peptide antigen as described in A-C above is coupled to KLH, and BALB/C mice are injected intradermally (ID) on the back with antigen in complete Freunds adjuvant (e.g., 50 µg antigen per mouse). The mice are boosted with same antigen in incomplete Freund adjuvant (e.g. 25 µg antigen per mouse) every three weeks. After the fifth boost, the animals are sacrificed and spleens are harvested.

Harvested spleen cells are fused to SP2/0 mouse myeloma fusion partner cells according to the standard protocol of Kohler and Milstein (1975). Colonies originating from the fusion are screened by ELISA for reactivity to the phospho-peptide and non-phospho-peptide forms of the antigen and by Western blot analysis (as described in Example 1 above). Colonies found to be positive by ELISA to the phospho-peptide while negative to the non-phospho-peptide are further characterized by Western blot analysis. Colonies found to be positive by Western blot analysis are subcloned by limited dilution. Mouse ascites are produced from a single clone obtained from subcloning, and tested for phospho-specificity (against the ORC3L, NDE1 or KIF1C) phospho-peptide antigen, as the case may be) on ELISA. Clones identified as positive on Western blot analysis using cell culture supernatant as having phospho-specificity, as indicated by a strong band in the induced lane and a weak band in the uninduced lane of the blot, are isolated and subcloned as clones producing monoclonal antibodies with the desired specificity.

Ascites fluid from isolated clones may be further tested by Western blot analysis. The ascites fluid should produce similar results on Western blot analysis as observed previously with the cell culture supernatant, indicating phospho-specificity against the phosphorylated target.

EXAMPLE 4

Production and Use of Aqua Peptides for Detecting and Quantitating Phosphorylation at a Novel Phosphorylation Site Heavy-isotope labeled peptides (AQUA peptides (internal standards)) for the detecting and quantitating a novel phosphorylation site of the invention (Table 1) only when the tyrosine, serine and/or threonine residue is phosphorylated are produced according to the standard AQUA methodology (see Gygi et al., Gerber et al., supra.) methods by first constructing a synthetic peptide standard corresponding to the phosphorylation site sequence and incorporating a heavy-isotope label. Subsequently, the MS" and LC-SRM signature of the peptide standard is validated, and the AQUA peptide is used to quantify native peptide in a biological sample, such as a digested cell extract. Production and use of exemplary AQUA peptides is provided below.

A. INPP4A (Tyrosine 933).

An AQUA peptide comprising the sequence, HYRPPEGTy*GKVET (SEQ ID NO: 46; y*=phosphotyrosine; Valine being $^{14}C/^{15}N$-labeled, as indicated in bold), which comprises the phosphorylation site derived from human INPP4A (a phosphatase, Tyr 933 being the phosphorylatable residue), is constructed according to standard synthesis techniques using, e.g., a Rainin/Protein Technologies, Inc., Symphony peptide synthesizer (see Merrifield, supra.) as further described below in Synthesis & MS/MS Signature. The INPP4A (tyr 933) AQUA peptide is then spiked into a biological sample to quantify the amount of phosphorylated INPP4A (tyr 933) in the sample, as further described below in Analysis & Quantification.

B. DCAMKL1 (Serine 334).

An AQUA peptide comprising the sequence SPSPs*PTSPGSLRK (SEQ ID NO: 51' y*=phosphoserine; Proline being $^{14}C/^{15}N$-labeled, as indicated in bold), which comprises the phosphorylation site derived from human DCAMKL1 (a Ser/Thr protein kinase, Ser 334 being the phosphorylatable residue), is constructed according to standard synthesis techniques using, e.g., a Rainin/Protein Technologies, Inc., Symphony peptide synthesizer (see Merrifield, supra.) as further described below in Synthesis & MS/MS Signature. The DCAMKL1 (ser 334) AQUA peptide is then spiked into a biological sample to quantify the amount of phosphorylated DCAMKL1 (ser 334) in the sample, as further described below in Analysis & Quantification.

C. HGFAC (Serine 388).

An AQUA peptide comprising the sequence VQLSPDLLATLPEPAs*PGR (SEQ ID NO: 47; s*=phosphoserine; Leucine being $^{14}C/^{15}N$-labeled, as indicated in bold), which comprises the phosphorylation site derived from human HGFAC (a protease, Ser 388 being the phosphorylatable residue), is constructed according to standard synthesis techniques using, e.g., a Rainin/Protein Technologies, Inc., Symphony peptide synthesizer (see Merrifield, supra.) as further described below in Synthesis & MS/MS Signature. The HGFAC (ser 388) AQUA peptide is then spiked into a biological sample to quantify the amount of phosphorylated HGFAC (ser 388) in the sample, as further described below in Analysis & Quantification.

D. ARHGEF11 (Threonine 668).

An AQUA peptide comprising the sequence SLENPt*PPFTPK (SEQ ID NO: 39; t*=phosphothreonine; Proline being $^{14}C/^{15}N$-labeled, as indicated in bold), which comprises the phosphorylation site derived from human ARHGEF11 (a g protein or regulator protein, Thr 668 being the phosphorylatable residue), is constructed according to standard synthesis techniques using, e.g., a Rainin/Protein Technologies, Inc., Symphony peptide synthesizer (see Merrifield, supra.) as further described below in Synthesis & MS/MS Signature. The ARHGEF11 (thr 668) AQUA peptide is then spiked into a biological sample to quantify the amount of phosphorylated ARHGEF11 (thr 668) in the sample, as further described below in Analysis & Quantification.

Synthesis & MS/MS Spectra.

Fluorenylmethoxycarbonyl (Fmoc)-derivatized amino acid monomers may be obtained from AnaSpec (San Jose, Calif). Fmoc-derivatized stable-isotope monomers containing one $^{15}$N and five to nine $^{13}$C atoms may be obtained from Cambridge Isotope Laboratories (Andover, Mass). Preloaded Wang resins may be obtained from Applied Biosystems. Synthesis scales may vary from 5 to 25 µmol. Amino acids are activated in situ with 1-H-benzotriazolium, 1-bis(dimethylamino) methylene]-hexafluorophosphate (1-),3-oxide:1-hydroxybenzotriazole hydrate and coupled at a 5-fold molar excess over peptide. Each coupling cycle is followed by capping with acetic anhydride to avoid accumulation of one-residue deletion peptide by-products. After synthesis peptide-resins are treated with a standard scavenger-containing trifluoroacetic acid (TFA)-water cleavage solution, and the peptides are precipitated by addition to cold ether. Peptides (i.e. a desired AQUA peptide described in A-D above) are purified by reversed-phase C18 HPLC using standard TFA/acetonitrile gradients and characterized by matrix-assisted laser desorption ionization-time of flight (Biflex III, Bruker Daltonics, Billerica, Mass.) and ion-trap (ThermoFinnigan, LCQ DecaXP or LTQ) MS.

MS/MS spectra for each AQUA peptide should exhibit a strong y-type ion peak as the most intense fragment ion that is suitable for use in an SRM monitoring/analysis. Reverse-phase microcapillary columns (0.1 Å~150-220 mm) are prepared according to standard methods. An Agilent 1100 liquid chromatograph may be used to develop and deliver a solvent gradient [0.4% acetic acid/0.005% heptafluorobutyric acid (HFBA)/7% methanol and 0.4% acetic acid/0.005% HFBA/65% methanol/35% acetonitrile] to the microcapillary column by means of a flow splitter. Samples are then directly loaded onto the microcapillary column by using a FAMOS inert capillary autosampler (LC Packings, San Francisco) after the flow split. Peptides are reconstituted in 6% acetic acid/0.01% TFA before injection.

Analysis & Quantification.

Target protein (e.g. a phosphorylated proteins of A-D above) in a biological sample is quantified using a validated AQUA peptide (as described above). The IAP method is then applied to the complex mixture of peptides derived from proteolytic cleavage of crude cell extracts to which the AQUA peptides have been spiked in.

LC-SRM of the entire sample is then carried out. MS/MS may be performed by using a ThermoFinnigan (San Jose, Calif.) mass spectrometer (LCQ DecaXP ion trap or TSQ Quantum triple quadrupole or LTQ). On the DecaXP, parent ions are isolated at 1.6 m/z width, the ion injection time being limited to 150 ms per microscan, with two microscans per peptide averaged, and with an AGC setting of $1\times10^8$; on the Quantum, Q1 is kept at 0.4 and Q3 at 0.8 m/z with a scan time of 200 ms per peptide. On both instruments, analyte and internal standard are analyzed in alternation within a previously known reverse-phase retention window; well-resolved pairs of internal standard and analyte are analyzed in separate retention segments to improve duty cycle. Data are processed by integrating the appropriate peaks in an extracted ion chromatogram (60.15 m/z from the fragment monitored) for the native and internal standard, followed by calculation of the ratio of peak areas multiplied by the absolute amount of internal standard (e.g., 500 fmol).

What is claimed is:

1. An isolated phosphorylation site-specific antibody that specifically binds EZH2 only when phosphorylated at T372 comprised within SEQ ID NO: 34, wherein said antibody does not bind EZH2 when not phosphorylated at said T372.

2. The antibody of claim 1, wherein said antibody is polyclonal.

3. The antibody of claim 1, wherein said antibody is monoclonal.

4. An isolated phosphorylation site-specific antibody that specifically binds NDE1 only when phosphorylated at T246 comprised within SEQ ID NO: 26, wherein said antibody does not bind NDE1 when not phosphorylated at said T246.

5. The antibody of claim 4, wherein said antibody is polyclonal.

6. The antibody of claim 4, wherein said antibody is monoclonal.

7. An isolated phosphorylation site-specific antibody that specifically binds MAP2K1 only when phosphorylated at T388 comprised within SEQ ID NO: 49, wherein said antibody does not bind MAP2K1 when not phosphorylated at said T388.

8. The antibody of claim 7, wherein said antibody is polyclonal.

9. The antibody of claim 7, wherein said antibody is monoclonal.

\* \* \* \* \*

SEQUENCE LISTING

```
<160> NUMBER OF SEQ ID NOS: 155

<210> SEQ ID NO 1
<211> LENGTH: 25
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Thr

<400> SEQUENCE: 1

Glu Phe Ser Gly Pro Ser Thr Pro Thr Gly Thr Leu Glu Phe Glu Gly
1               5                   10                  15

Gly Glu Val Ser Leu Glu Gly Gly Lys
            20                  25

<210> SEQ ID NO 2
<211> LENGTH: 14
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 2

Val Ala Asp Ser Asp Tyr Glu Ala Ile Cys Lys Val Pro Arg
1               5                   10

<210> SEQ ID NO 3
<211> LENGTH: 32
```

```
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Ser

<400> SEQUENCE: 3

Ser Gln Asp Ser Tyr Pro Val Ser Pro Arg Pro Phe Ser Ser Pro Ser
1               5                   10                  15

Met Ser Pro Ser His Gly Met Asn Ile His Asn Leu Ala Ser Gly Lys
            20                  25                  30

<210> SEQ ID NO 4
<211> LENGTH: 32
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: Phosphorylated-Ser

<400> SEQUENCE: 4

Ser Gln Asp Ser Tyr Pro Val Ser Pro Arg Pro Phe Ser Ser Pro Ser
1               5                   10                  15

Met Ser Pro Ser His Gly Met Asn Ile His Asn Leu Ala Ser Gly Lys
            20                  25                  30

<210> SEQ ID NO 5
<211> LENGTH: 22
<212> TYPE: PRT
<213> ORGANISM: Homo sapiens
<220> FEATURE:
<221> NAME/KEY: MOD_RES
<222> LOCATION: (21)..(21)
<223> OTHER INFORMATION: Phosphorylated-Thr

<400> SEQUENCE: 5

Thr Leu Cys Ser Met His His Leu Val Pro Gly Gly Ser Ala Pro Pro
1               5                   10                  15

Ser Pro Leu Leu Thr Arg
            20

<210> SEQ ID NO 6
<211> LENGTH: 13
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 6

Lys Ser Ser Phe Phe Ser Ser Pro Pro Tyr Phe Glu Asp
1               5                   10

<210> SEQ ID NO 7
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 7

Thr Val Ser His Leu Tyr Gln Glu Ser Ile Ser Lys
1               5                   10
```

```
<210> SEQ ID NO 8
<211> LENGTH: 17
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 8

Asn Arg Pro Pro Phe Gly Gln Gly Tyr Thr Gln Pro Gly Pro Gly Tyr
1               5                   10                  15

Arg

<210> SEQ ID NO 9
<211> LENGTH: 15
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 9

Gly Arg Gly Thr Gly Glu Ala Glu Glu Glu Tyr Val Gly Pro Arg
1               5                   10                  15

<210> SEQ ID NO 10
<211> LENGTH: 21
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Ser

<400> SEQUENCE: 10

Ser Tyr Thr Pro Pro Thr Pro Thr Thr Ser Lys Leu Pro Thr Ile Pro
1               5                   10                  15

Asp Trp Asp Gly Arg
            20

<210> SEQ ID NO 11
<211> LENGTH: 15
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 11

Ser Gln Glu Glu Leu Arg Glu Asp Lys Ala Tyr Gln Leu Glu Arg
1               5                   10                  15

<210> SEQ ID NO 12
<211> LENGTH: 15
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Ser

<400> SEQUENCE: 12

Ser Leu Pro Ala Ser Pro Ser Thr Ser Asp Phe Cys Gln Thr Arg
1               5                   10                  15
```

```
<210> SEQ ID NO 13
<211> LENGTH: 17
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 13

Cys Ala Ser Cys Pro Tyr Leu Gly Met Pro Ala Phe Lys Pro Gly Glu
1               5                   10                  15

Lys

<210> SEQ ID NO 14
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 14

Gly Gly Gly Asp Pro Tyr Ser Asp Leu Ser Lys
1               5                   10

<210> SEQ ID NO 15
<211> LENGTH: 29
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: Phosphorylated-Thr

<400> SEQUENCE: 15

Thr Pro Glu Thr Val Val Pro Ala Ala Pro Glu Leu Gln Pro Ser Thr
1               5                   10                  15

Ser Thr Asp Gln Pro Val Thr Pro Glu Pro Thr Ser Arg
            20                  25

<210> SEQ ID NO 16
<211> LENGTH: 8
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 16

Thr Asp Leu Tyr His Leu Gln Lys
1               5

<210> SEQ ID NO 17
<211> LENGTH: 18
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Ser

<400> SEQUENCE: 17

Met Glu Thr Val Ser Asn Ala Ser Ser Ser Asn Pro Ser Ser Pro
1               5                   10                  15
```

Gly Arg

```
<210> SEQ ID NO 18
<211> LENGTH: 18
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Ser

<400> SEQUENCE: 18

Met Glu Thr Val Ser Asn Ala Ser Ser Ser Ser Asn Pro Ser Ser Pro
1               5                   10                  15

Gly Arg

<210> SEQ ID NO 19
<211> LENGTH: 18
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Ser

<400> SEQUENCE: 19

Met Glu Thr Val Ser Asn Ala Ser Ser Ser Ser Asn Pro Ser Ser Pro
1               5                   10                  15

Gly Arg

<210> SEQ ID NO 20
<211> LENGTH: 20
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Ser

<400> SEQUENCE: 20

Ser Ser Phe Thr Pro Ser Ser Pro Glu Asn Val Ile Gly Asp Phe Leu
1               5                   10                  15

Leu Gln Asp Arg
            20

<210> SEQ ID NO 21
<211> LENGTH: 24
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 21

Arg Val Glu His Asn Gln Ser Tyr Ser Gln Ala Gly Ile Thr Glu Thr
1               5                   10                  15

Glu Trp Thr Ser Gly Ser Ser Lys
            20

<210> SEQ ID NO 22
<211> LENGTH: 25
<212> TYPE: PRT
<213> ORGANISM: Homo sapiens
<220> FEATURE:
<221> NAME/KEY: MOD_RES
```

```
<222> LOCATION: (17)..(17)
<223> OTHER INFORMATION: Phosphorylated-Tyr

<400> SEQUENCE: 22

Ser Gly Cys Arg Asn Pro Pro Gln Pro Val Asp Trp Asn Asn Asp
1               5                   10                  15

Tyr Cys Ser Ser Gly Gly Met Gln Arg
            20                  25

<210> SEQ ID NO 23
<211> LENGTH: 14
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 23

Arg Pro Thr Phe Val Pro Gln Trp Tyr Val Gln Gln Met Lys
1               5                   10

<210> SEQ ID NO 24
<211> LENGTH: 16
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Phosphorylated-Tyr

<400> SEQUENCE: 24

Ser Pro Gln His Phe His Arg Pro Asp Gln Gly Ile Asn Ile Tyr Arg
1               5                   10                  15

<210> SEQ ID NO 25
<211> LENGTH: 18
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Thr

<400> SEQUENCE: 25

Asn Glu Pro Thr Thr Pro Ser Trp Leu Ala Asp Ile Pro Pro Trp Val
1               5                   10                  15

Pro Lys

<210> SEQ ID NO 26
<211> LENGTH: 16
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Thr

<400> SEQUENCE: 26

Gly Leu Asp Asp Ser Thr Gly Gly Thr Pro Leu Thr Pro Ala Ala Arg
1               5                   10                  15

<210> SEQ ID NO 27
<211> LENGTH: 12
<212> TYPE: PRT
<213> ORGANISM: Homo sapiens
<220> FEATURE:
<221> NAME/KEY: MOD_RES
```

```
<222> LOCATION: (8)..(8)
<223> OTHER INFORMATION: Phosphorylated-Ser

<400> SEQUENCE: 27

Arg Pro Pro Ser Pro Arg Arg Ser His His Pro Arg
1               5                   10

<210> SEQ ID NO 28
<211> LENGTH: 12
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Ser

<400> SEQUENCE: 28

Arg Pro Pro Ser Pro Arg Arg Ser His His Pro Arg
1               5                   10

<210> SEQ ID NO 29
<211> LENGTH: 36
<212> TYPE: PRT
<213> ORGANISM: Homo sapiens
<220> FEATURE:
<221> NAME/KEY: MOD_RES
<222> LOCATION: (35)..(35)
<223> OTHER INFORMATION: Phosphorylated-Ser

<400> SEQUENCE: 29

Ser Gly Pro Gln Ser Pro Ala Pro Ala Ala Pro Ala Gln Pro Gly Ala
1               5                   10                  15

Thr Leu Ala Pro Pro Thr Pro Pro Arg Pro Arg Asp Gly Gly Thr Pro
            20                  25                  30

Arg His Ser Arg
        35

<210> SEQ ID NO 30
<211> LENGTH: 36
<212> TYPE: PRT
<213> ORGANISM: Homo sapiens
<220> FEATURE:
<221> NAME/KEY: MOD_RES
<222> LOCATION: (22)..(22)
<223> OTHER INFORMATION: Phosphorylated-Thr

<400> SEQUENCE: 30

Ser Gly Pro Gln Ser Pro Ala Pro Ala Ala Pro Ala Gln Pro Gly Ala
1               5                   10                  15

Thr Leu Ala Pro Pro Thr Pro Pro Arg Pro Arg Asp Gly Gly Thr Pro
            20                  25                  30

Arg His Ser Arg
        35

<210> SEQ ID NO 31
<211> LENGTH: 36
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Ser

<400> SEQUENCE: 31

Ser Gly Pro Gln Ser Pro Ala Pro Ala Ala Pro Ala Gln Pro Gly Ala
1               5                   10                  15
```

```
Thr Leu Ala Pro Pro Thr Pro Pro Arg Pro Arg Asp Gly Gly Thr Pro
            20                  25                  30

Arg His Ser Arg
            35

<210> SEQ ID NO 32
<211> LENGTH: 18
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 32

Trp Ser Pro Ala Tyr Ser Phe Ser Ser Asp Ser Pro Leu Asp Ser Ser
1               5                   10                  15

Pro Lys

<210> SEQ ID NO 33
<211> LENGTH: 16
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Ser

<400> SEQUENCE: 33

Asn Ser Leu Pro Ala Ser Pro Ala His Gln Leu Ser Ser Ser Pro Arg
1               5                   10                  15

<210> SEQ ID NO 34
<211> LENGTH: 19
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Thr

<400> SEQUENCE: 34

Leu Pro Asn Asn Ser Ser Arg Pro Ser Thr Pro Thr Ile Asn Val Leu
1               5                   10                  15

Glu Ser Lys

<210> SEQ ID NO 35
<211> LENGTH: 19
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Ser

<400> SEQUENCE: 35

Leu Pro Asn Asn Ser Ser Arg Pro Ser Thr Pro Thr Ile Asn Val Leu
1               5                   10                  15

Glu Ser Lys

<210> SEQ ID NO 36
<211> LENGTH: 19
<212> TYPE: PRT
<213> ORGANISM: Homo sapiens
<220> FEATURE:
<221> NAME/KEY: MOD_RES
<222> LOCATION: (9)..(9)
```

```
<223> OTHER INFORMATION: Phosphorylated-Ser

<400> SEQUENCE: 36

Ala Pro Leu Lys Pro Tyr Pro Val Ser Pro Ser Asp Lys Val Leu Ile
1               5                   10                  15

Gln Glu Lys

<210> SEQ ID NO 37
<211> LENGTH: 33
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Phosphorylated-Thr

<400> SEQUENCE: 37

Asp Leu Leu His Ser Gly Pro Gly Lys Leu Pro Gln Thr Pro Leu Asp
1               5                   10                  15

Thr Gly Ile Pro Phe Pro Pro Val Phe Ser Thr Ser Ser Ala Gly Val
            20                  25                  30

Lys

<210> SEQ ID NO 38
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 38

Tyr Gln Thr Asp Leu Tyr Glu Arg Glu Arg
1               5                   10

<210> SEQ ID NO 39
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Thr

<400> SEQUENCE: 39

Ser Leu Glu Asn Pro Thr Pro Pro Phe Thr Pro Lys
1               5                   10

<210> SEQ ID NO 40
<211> LENGTH: 12
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Thr

<400> SEQUENCE: 40

Ser Leu Glu Asn Pro Thr Pro Pro Phe Thr Pro Lys
1               5                   10

<210> SEQ ID NO 41
<211> LENGTH: 24
<212> TYPE: PRT
<213> ORGANISM: Homo sapiens
<220> FEATURE:
```

```
<221> NAME/KEY: MOD_RES
<222> LOCATION: (14)..(14)
<223> OTHER INFORMATION: Phosphorylated-Tyr

<400> SEQUENCE: 41

Gln Val Phe Glu Ser Asp Glu Ala Pro Asp Gly Asn Ser Tyr Gln Asp
1               5                   10                  15

Asp Gln Asp Asp Leu Lys Arg Arg
            20

<210> SEQ ID NO 42
<211> LENGTH: 24
<212> TYPE: PRT
<213> ORGANISM: Homo sapiens
<220> FEATURE:
<221> NAME/KEY: MOD_RES
<222> LOCATION: (21)..(21)
<223> OTHER INFORMATION: Phosphorylated-Ser

<400> SEQUENCE: 42

Thr Leu Val Ile Thr Ser Thr Pro Ala Ser Pro Asn Arg Glu Leu His
1               5                   10                  15

Pro Gln Leu Leu Ser Pro Thr Lys
            20

<210> SEQ ID NO 43
<211> LENGTH: 13
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Ser

<400> SEQUENCE: 43

Thr Leu Val Ile Thr Ser Thr Pro Ala Ser Pro Asn Arg
1               5                   10

<210> SEQ ID NO 44
<211> LENGTH: 11
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 44

Gly Leu Ile Val Tyr Cys Val Thr Ser Pro Lys
1               5                   10

<210> SEQ ID NO 45
<211> LENGTH: 12
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Ser

<400> SEQUENCE: 45

Phe Leu Met Pro Glu Ala Tyr Pro Ser Ser Pro Arg
1               5                   10

<210> SEQ ID NO 46
<211> LENGTH: 14
<212> TYPE: PRT
<213> ORGANISM: Homo sapiens
```

```
<220> FEATURE:
<221> NAME/KEY: MOD_RES
<222> LOCATION: (9)..(9)
<223> OTHER INFORMATION: Phosphorylated-Tyr

<400> SEQUENCE: 46

His Tyr Arg Pro Pro Glu Gly Thr Tyr Gly Lys Val Glu Thr
1               5                   10

<210> SEQ ID NO 47
<211> LENGTH: 19
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Phosphorylated-Ser

<400> SEQUENCE: 47

Val Gln Leu Ser Pro Asp Leu Leu Ala Thr Leu Pro Glu Pro Ala Ser
1               5                   10                  15

Pro Gly Arg

<210> SEQ ID NO 48
<211> LENGTH: 19
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Ser

<400> SEQUENCE: 48

Val Gln Leu Ser Pro Asp Leu Leu Ala Thr Leu Pro Glu Pro Ala Ser
1               5                   10                  15

Pro Gly Arg

<210> SEQ ID NO 49
<211> LENGTH: 31
<212> TYPE: PRT
<213> ORGANISM: Homo sapiens
<220> FEATURE:
<221> NAME/KEY: MOD_RES
<222> LOCATION: (26)..(26)
<223> OTHER INFORMATION: Phosphorylated-Thr

<400> SEQUENCE: 49

Arg Ser Asp Ala Glu Glu Val Asp Phe Ala Gly Trp Leu Cys Ser Thr
1               5                   10                  15

Ile Gly Leu Asn Gln Pro Ser Thr Pro Thr His Ala Ala Gly Val
            20                  25                  30

<210> SEQ ID NO 50
<211> LENGTH: 12
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Thr

<400> SEQUENCE: 50

Ala Tyr Gly Val Pro Val Lys Pro Met Thr Pro Lys
1               5                   10

<210> SEQ ID NO 51
<211> LENGTH: 14
```

```
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Ser

<400> SEQUENCE: 51

Ser Pro Ser Pro Ser Pro Thr Ser Pro Gly Ser Leu Arg Lys
1               5                   10

<210> SEQ ID NO 52
<211> LENGTH: 14
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Ser

<400> SEQUENCE: 52

Ser Pro Ser Pro Ser Pro Thr Ser Pro Gly Ser Leu Arg Lys
1               5                   10

<210> SEQ ID NO 53
<211> LENGTH: 14
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Ser

<400> SEQUENCE: 53

Ser Pro Ser Pro Ser Pro Thr Ser Pro Gly Ser Leu Arg Lys
1               5                   10

<210> SEQ ID NO 54
<211> LENGTH: 14
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Ser

<400> SEQUENCE: 54

Gly Ser Thr Ile Tyr Thr Gly Tyr Pro Leu Ser Pro Thr Lys
1               5                   10

<210> SEQ ID NO 55
<211> LENGTH: 16
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 55

Gly Leu Asp Ile Glu Ser Tyr Asp Ser Leu Glu Arg Pro Leu Arg Lys
1               5                   10                  15

<210> SEQ ID NO 56
<211> LENGTH: 18
<212> TYPE: PRT
<213> ORGANISM: Homo sapiens
<220> FEATURE:
<221> NAME/KEY: MOD_RES
<222> LOCATION: (14)..(14)
```

<223> OTHER INFORMATION: Phosphorylated-Thr

<400> SEQUENCE: 56

Gly Ser Ala Leu Gly Thr Pro Ala Ala Ala Glu Pro Val Thr Pro Thr
1               5                   10                  15

Ser Lys

<210> SEQ ID NO 57
<211> LENGTH: 24
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 57

Ala His Cys Gly Pro Ala Glu Leu Cys Glu Phe Tyr Ser Arg Asp Pro
1               5                   10                  15

Asp Gly Leu Pro Cys Asn Leu Arg
            20

<210> SEQ ID NO 58
<211> LENGTH: 19
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Ser

<400> SEQUENCE: 58

Asn Ser Val Pro Gln Arg Pro Gly Pro Pro Ala Ser Pro Ala Ser Asp
1               5                   10                  15

Pro Ser Arg

<210> SEQ ID NO 59
<211> LENGTH: 19
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Ser

<400> SEQUENCE: 59

Asn Ser Val Pro Gln Arg Pro Gly Pro Pro Ala Ser Pro Ala Ser Asp
1               5                   10                  15

Pro Ser Arg

<210> SEQ ID NO 60
<211> LENGTH: 19
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: Phosphorylated-Ser

<400> SEQUENCE: 60

Asn Ser Val Pro Gln Arg Pro Gly Pro Pro Ala Ser Pro Ala Ser Asp
1               5                   10                  15

Pro Ser Arg

<210> SEQ ID NO 61

```
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 61

Lys Ser Gly Asn Tyr Phe Phe Leu Asp Asp
1               5                   10

<210> SEQ ID NO 62
<211> LENGTH: 17
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 62

Ile Thr Glu Asn Tyr Asp Cys Gly Thr Lys Leu Pro Gly Leu Leu Lys
1               5                   10                  15

Arg

<210> SEQ ID NO 63
<211> LENGTH: 21
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Thr

<400> SEQUENCE: 63

Arg Gln Leu Pro Gln Thr Pro Ser Thr Pro Arg Pro His Val Ser Tyr
1               5                   10                  15

Ser Pro Val Ile Arg
            20

<210> SEQ ID NO 64
<211> LENGTH: 21
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Phosphorylated-Ser

<400> SEQUENCE: 64

Arg Gln Leu Pro Gln Thr Pro Ser Thr Pro Arg Pro His Val Ser Tyr
1               5                   10                  15

Ser Pro Val Ile Arg
            20

<210> SEQ ID NO 65
<211> LENGTH: 19
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Ser

<400> SEQUENCE: 65

Cys Thr Phe Ser Ala Thr Gly Cys Pro Ser Glu Gln Pro Thr Cys Leu
1               5                   10                  15
```

Trp Phe Arg

<210> SEQ ID NO 66
<211> LENGTH: 19
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Thr

<400> SEQUENCE: 66

Cys Thr Phe Ser Ala Thr Gly Cys Pro Ser Glu Gln Pro Thr Cys Leu
1               5                   10                  15

Trp Phe Arg

<210> SEQ ID NO 67
<211> LENGTH: 19
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Thr

<400> SEQUENCE: 67

Cys Thr Phe Ser Ala Thr Gly Cys Pro Ser Glu Gln Pro Thr Cys Leu
1               5                   10                  15

Trp Phe Arg

<210> SEQ ID NO 68
<211> LENGTH: 14
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Thr

<400> SEQUENCE: 68

Ile Phe Val Gly Gly Leu Ser Pro Asp Thr Pro Glu Glu Lys
1               5                   10

<210> SEQ ID NO 69
<211> LENGTH: 16
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Ser

<400> SEQUENCE: 69

His Thr Gly Pro Asn Ser Pro Asp Thr Ala Asn Asp Gly Phe Val Arg
1               5                   10                  15

<210> SEQ ID NO 70
<211> LENGTH: 23
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 70

Val Met Thr Ile Pro Tyr Gln Pro Met Pro Ala Ser Ser Pro Val Ile

Cys Ala Gly Gly Gln Asp Arg
            20

<210> SEQ ID NO 71
<211> LENGTH: 27
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Phosphorylated-Thr

<400> SEQUENCE: 71

Thr Ala Val Ala Pro Ser Ala Val Asn Leu Ala Asp Pro Arg Thr Pro
1               5                   10                  15

Thr Ala Pro Ala Val Asn Leu Ala Gly Ala Arg
            20                  25

<210> SEQ ID NO 72
<211> LENGTH: 18
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 72

Ser Ser Thr Pro Pro Gly Glu Ser Tyr Phe Gly Val Ser Ser Leu Gln
1               5                   10                  15

Leu Lys

<210> SEQ ID NO 73
<211> LENGTH: 30
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Ser

<400> SEQUENCE: 73

Ser Pro Pro Met Glu Leu Gln Pro Pro Val Ser Pro Gln Gln Ser Glu
1               5                   10                  15

Cys Asn Pro Val Gly Ala Leu Gln Glu Leu Val Val Gln Lys
            20                  25                  30

<210> SEQ ID NO 74
<211> LENGTH: 17
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Ser

<400> SEQUENCE: 74

Ala Ala Ala Gly Pro Leu Asp Met Ser Leu Pro Ser Thr Pro Asp Ile
1               5                   10                  15

Lys

<210> SEQ ID NO 75
<211> LENGTH: 17
<212> TYPE: PRT
<213> ORGANISM: Homo sapiens

```
<220> FEATURE:
<221> NAME/KEY: MOD_RES
<222> LOCATION: (13)..(13)
<223> OTHER INFORMATION: Phosphorylated-Thr

<400> SEQUENCE: 75

Ala Ala Ala Gly Pro Leu Asp Met Ser Leu Pro Ser Thr Pro Asp Ile
1               5                   10                  15

Lys

<210> SEQ ID NO 76
<211> LENGTH: 18
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Ser

<400> SEQUENCE: 76

Ala Pro Gly Tyr Pro Ser Ser Pro Val Thr Thr Ala Ser Gly Thr Thr
1               5                   10                  15

Leu Arg

<210> SEQ ID NO 77
<211> LENGTH: 33
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Thr

<400> SEQUENCE: 77

Ala Gly Val Leu Gly Gly Pro Ala Thr Pro Ala Ser Gly Pro Gly Pro
1               5                   10                  15

Ala Ser Ala Glu Pro Ala Val Thr Glu Pro Gly Leu Gly Pro Asp Pro
            20                  25                  30

Lys

<210> SEQ ID NO 78
<211> LENGTH: 33
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Ser

<400> SEQUENCE: 78

Ala Gly Val Leu Gly Gly Pro Ala Thr Pro Ala Ser Gly Pro Gly Pro
1               5                   10                  15

Ala Ser Ala Glu Pro Ala Val Thr Glu Pro Gly Leu Gly Pro Asp Pro
            20                  25                  30

Lys

<210> SEQ ID NO 79
<211> LENGTH: 24
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Tyr

<400> SEQUENCE: 79
```

```
Glu Ser Glu Ser Val Ser Lys Glu Lys Glu Gln Asn Tyr Asp Leu
1               5                   10                  15

Thr Glu Val Ser Glu Ser Met Lys
            20
```

<210> SEQ ID NO 80
<211> LENGTH: 18
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 80

```
Glu Gly Tyr Asn Asn Pro Pro Ile Ser Gly Glu Asn Leu Ile Gly Leu
1               5                   10                  15

Ser Arg
```

<210> SEQ ID NO 81
<211> LENGTH: 26
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Thr

<400> SEQUENCE: 81

```
Thr Ser Gly Ala Pro Gly Ser Pro Gln Thr Pro Pro Glu Arg His Asp
1               5                   10                  15

Ser Gly Gly Ser Leu Pro Leu Thr Pro Arg
            20                  25
```

<210> SEQ ID NO 82
<211> LENGTH: 26
<212> TYPE: PRT
<213> ORGANISM: Homo sapiens
<220> FEATURE:
<221> NAME/KEY: MOD_RES
<222> LOCATION: (24)..(24)
<223> OTHER INFORMATION: Phosphorylated-Thr

<400> SEQUENCE: 82

```
Thr Ser Gly Ala Pro Gly Ser Pro Gln Thr Pro Pro Glu Arg His Asp
1               5                   10                  15

Ser Gly Gly Ser Leu Pro Leu Thr Pro Arg
            20                  25
```

<210> SEQ ID NO 83
<211> LENGTH: 15
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Ser

<400> SEQUENCE: 83

```
Ile Pro Asn Ser Tyr Glu Val Leu Phe Pro Glu Ser Pro Ala Arg
1               5                   10                  15
```

<210> SEQ ID NO 84
<211> LENGTH: 15
<212> TYPE: PRT
<213> ORGANISM: Homo sapiens

```
<220> FEATURE:
<221> NAME/KEY: MOD_RES
<222> LOCATION: (4)..(4)
<223> OTHER INFORMATION: Phosphorylated-Tyr

<400> SEQUENCE: 84

Thr Pro Leu Tyr Leu Gln Pro Asp Ala Tyr Gly Ser Leu Asp Arg
1               5                   10                  15

<210> SEQ ID NO 85
<211> LENGTH: 11
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Ser

<400> SEQUENCE: 85

Ser Pro Tyr Lys Phe Pro Ser Ser Pro Leu Arg
1               5                   10

<210> SEQ ID NO 86
<211> LENGTH: 16
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Thr

<400> SEQUENCE: 86

Leu Gly Leu Pro Pro Leu Thr Pro Glu Gln Gln Glu Ala Leu Gln Lys
1               5                   10                  15

<210> SEQ ID NO 87
<211> LENGTH: 19
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Phosphorylated-Thr

<400> SEQUENCE: 87

Val Val Ser Ile Ser Ser Glu His Leu Glu Pro Ile Thr Pro Thr Lys
1               5                   10                  15

Asn Asn Lys

<210> SEQ ID NO 88
<211> LENGTH: 19
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Phosphorylated-Thr

<400> SEQUENCE: 88

Val Val Ser Ile Ser Ser Glu His Leu Glu Pro Ile Thr Pro Thr Lys
1               5                   10                  15

Asn Asn Lys

<210> SEQ ID NO 89
<211> LENGTH: 35
<212> TYPE: PRT
<213> ORGANISM: Homo sapiens
<220> FEATURE:
```

-continued

```
<221> NAME/KEY: MOD_RES
<222> LOCATION: (34)..(34)
<223> OTHER INFORMATION: Phosphorylated-Tyr

<400> SEQUENCE: 89
```

Arg Pro Gln Tyr Ser Asn Pro Pro Val Gln Gly Glu Val Met Glu Gly
1               5                   10                  15

Ala Asp Asn Gln Gly Ala Gly Glu Gln Gly Arg Pro Val Arg Gln Asn
            20                  25                  30

Met Tyr Arg
        35

```
<210> SEQ ID NO 90
<211> LENGTH: 15
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 90
```

Ser Gly Leu Ile Tyr Leu Thr Asn His Ile Ala Pro His Ala Arg
1               5                   10                  15

```
<210> SEQ ID NO 91
<211> LENGTH: 22
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Ser

<400> SEQUENCE: 91
```

Gly Gln Glu Leu Ala Phe Pro Leu Ser Pro Asp Trp Gln Val Asp Tyr
1               5                   10                  15

Glu Ser Tyr Thr Trp Arg
            20

```
<210> SEQ ID NO 92
<211> LENGTH: 18
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Ser

<400> SEQUENCE: 92
```

Arg Leu Gly Gly Leu Arg Pro Glu Ser Pro Glu Ser Leu Thr Ser Val
1               5                   10                  15

Ser Arg

```
<210> SEQ ID NO 93
<211> LENGTH: 24
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Phosphorylated-Tyr

<400> SEQUENCE: 93
```

Gln Val Gln His Glu Glu Ser Thr Glu Gly Glu Ala Asp His Ser Gly
1               5                   10                  15

```
Tyr Ala Gly Glu Leu Gly Phe Arg
            20

<210> SEQ ID NO 94
<211> LENGTH: 29
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Ser

<400> SEQUENCE: 94

Arg Leu Leu Ser Pro Ala Gly Ser Ser Gly Ala Pro Ala Ser Pro Ala
1               5                   10                  15

Cys Ser Ser Pro Pro Ser Ser Glu Phe Met Asp Val Asn
            20                  25

<210> SEQ ID NO 95
<211> LENGTH: 29
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Ser

<400> SEQUENCE: 95

Arg Leu Leu Ser Pro Ala Gly Ser Ser Gly Ala Pro Ala Ser Pro Ala
1               5                   10                  15

Cys Ser Ser Pro Pro Ser Ser Glu Phe Met Asp Val Asn
             20                  25

<210> SEQ ID NO 96
<211> LENGTH: 18
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Ser

<400> SEQUENCE: 96

Gly Pro Ser Thr Pro Lys Ser Pro Gly Ala Ser Asn Phe Ser Thr Leu
1               5                   10                  15

Pro Lys

<210> SEQ ID NO 97
<211> LENGTH: 12
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 97

Val Leu Glu Tyr Glu Met Thr Gln Phe Asp Arg Arg
1               5                   10

<210> SEQ ID NO 98
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Thr
```

```
<400> SEQUENCE: 98

Tyr Pro Asn Thr Pro Met Ser His Lys
1               5

<210> SEQ ID NO 99
<211> LENGTH: 11
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Ser

<400> SEQUENCE: 99

Ser Thr Ser Thr Pro Thr Ser Pro Gly Pro Arg
1               5                   10

<210> SEQ ID NO 100
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Thr

<400> SEQUENCE: 100

Ser Thr Ser Thr Pro Thr Ser Pro Gly Pro Arg
1               5                   10

<210> SEQ ID NO 101
<211> LENGTH: 15
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Thr

<400> SEQUENCE: 101

Ser Pro Thr Pro Val Lys Pro Thr Glu Pro Cys Thr Pro Ser Lys
1               5                   10                  15

<210> SEQ ID NO 102
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 102

Thr Phe Ser Val Tyr Ser Ser Ser Arg
1               5

<210> SEQ ID NO 103
<211> LENGTH: 20
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: Phosphorylated-Ser

<400> SEQUENCE: 103

Ser Ser Ser Val Ser Pro Ser Ser Trp Lys Ser Pro Pro Ala Ser Pro
1               5                   10                  15
```

```
Glu Ser Trp Lys
        20

<210> SEQ ID NO 104
<211> LENGTH: 20
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Ser

<400> SEQUENCE: 104

Ser Ser Ser Val Ser Pro Ser Ser Trp Lys Ser Pro Pro Ala Ser Pro
1               5                   10                  15

Glu Ser Trp Lys
        20

<210> SEQ ID NO 105
<211> LENGTH: 19
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: Phosphorylated-Ser

<400> SEQUENCE: 105

Asp Ala Leu Val Leu Thr Pro Ala Ser Leu Trp Lys Pro Ser Ser Pro
1               5                   10                  15

Val Ser Gln

<210> SEQ ID NO 106
<211> LENGTH: 19
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Ser

<400> SEQUENCE: 106

Asp Ala Leu Val Leu Thr Pro Ala Ser Leu Trp Lys Pro Ser Ser Pro
1               5                   10                  15

Val Ser Gln

<210> SEQ ID NO 107
<211> LENGTH: 19
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Ser

<400> SEQUENCE: 107

Asp Ala Leu Val Leu Thr Pro Ala Ser Leu Trp Lys Pro Ser Ser Pro
1               5                   10                  15

Val Ser Gln

<210> SEQ ID NO 108
<211> LENGTH: 13
<212> TYPE: PRT
<213> ORGANISM: Homo sapiens
<220> FEATURE:
<221> NAME/KEY: MOD_RES
```

```
<222> LOCATION: (3)..(3)
<223> OTHER INFORMATION: Phosphorylated-Ser

<400> SEQUENCE: 108

Arg Ser Ser Ser Gly Ser Pro Pro Ser Pro Gln Ser Arg
1               5                   10

<210> SEQ ID NO 109
<211> LENGTH: 13
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Ser

<400> SEQUENCE: 109

Arg Ser Ser Ser Gly Ser Pro Pro Ser Pro Gln Ser Arg
1               5                   10

<210> SEQ ID NO 110
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Ser

<400> SEQUENCE: 110

Arg Ser Ser Ser Gly Ser Pro Pro Ser Pro Gln Ser Arg
1               5                   10

<210> SEQ ID NO 111
<211> LENGTH: 15
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Ser

<400> SEQUENCE: 111

Glu Trp Pro Val Ser Ser Phe Asn Arg Pro Phe Pro Asn Ser Pro
1               5                   10                  15

<210> SEQ ID NO 112
<211> LENGTH: 16
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 112

Gly Gly Phe Asp Gly Glu Tyr Gln Asp Asp Ser Leu Asp Leu Leu Arg
1               5                   10                  15

<210> SEQ ID NO 113
<211> LENGTH: 7
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 113
```

```
His Thr Pro Leu Tyr Glu Arg
1               5

<210> SEQ ID NO 114
<211> LENGTH: 11
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Ser

<400> SEQUENCE: 114

His Gly Leu Leu Leu Pro Ala Ser Pro Val Arg
1               5                   10

<210> SEQ ID NO 115
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Ser

<400> SEQUENCE: 115

Arg Ile Asp Phe Thr Pro Val Ser Pro Ala Pro Ser Pro Thr Arg
1               5                   10                  15

<210> SEQ ID NO 116
<211> LENGTH: 15
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Ser

<400> SEQUENCE: 116

Arg Ile Asp Phe Thr Pro Val Ser Pro Ala Pro Ser Pro Thr Arg
1               5                   10                  15

<210> SEQ ID NO 117
<211> LENGTH: 17
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Ser

<400> SEQUENCE: 117

Met Phe Val Ser Ser Ser Gly Leu Pro Pro Ser Pro Val Pro Ser Pro
1               5                   10                  15

Arg

<210> SEQ ID NO 118
<211> LENGTH: 17
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Phosphorylated-Ser

<400> SEQUENCE: 118

Met Phe Val Ser Ser Ser Gly Leu Pro Pro Ser Pro Val Pro Ser Pro
1               5                   10                  15
```

Arg

```
<210> SEQ ID NO 119
<211> LENGTH: 18
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Thr

<400> SEQUENCE: 119

Val His Ala Tyr Phe Ala Pro Val Thr Pro Pro Ser Val Gly Gly
1               5                   10                  15

Ser Arg

<210> SEQ ID NO 120
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 120

Gly Gly His Ser Asp Asp Leu Tyr Ala Val Pro His Arg
1               5                   10

<210> SEQ ID NO 121
<211> LENGTH: 11
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 121

Gly Ile Cys Asp Tyr Phe Pro Ser Pro Ser Lys
1               5                   10

<210> SEQ ID NO 122
<211> LENGTH: 29
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: Phosphorylated-Ser

<400> SEQUENCE: 122

Arg Pro Glu Phe Phe Thr Phe Gly Gly Asn Thr Ala Val Leu Thr Pro
1               5                   10                  15

Leu Ser Pro Ser Ala Ser Glu Asn Cys Ser Ala Tyr Lys
            20                  25

<210> SEQ ID NO 123
<211> LENGTH: 33
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Ser

<400> SEQUENCE: 123

Ser Ser Asp Arg Asn Pro Pro Leu Ser Pro Gln Ser Ser Ile Asp Ser
```

```
                1               5                  10                 15
Glu Leu Ser Ala Ser Glu Leu Asp Glu Asp Ser Ile Gly Ser Asn Tyr
                20                 25                 30

Lys

<210> SEQ ID NO 124
<211> LENGTH: 13
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Ser

<400> SEQUENCE: 124

Val Pro Lys Ser Pro Glu His Ser Ala Glu Pro Ile Arg
1               5                  10

<210> SEQ ID NO 125
<211> LENGTH: 20
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 125

Phe Ser Thr Tyr Thr Ser Asp Lys Asp Glu Asn Lys Leu Ser Glu Ala
1               5                  10                 15

Ser Gly Gly Arg
            20

<210> SEQ ID NO 126
<211> LENGTH: 16
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 126

Ser Trp Ala Ser Pro Val Tyr Thr Glu Ala Asp Gly Thr Phe Ser Arg
1               5                  10                 15

<210> SEQ ID NO 127
<211> LENGTH: 24
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Ser

<400> SEQUENCE: 127

Gln Ile Pro Pro Pro Gln Thr Pro Ser Thr Asp Pro Gln Thr Leu Pro
1               5                  10                 15

Leu Ser Phe Arg Ser Leu Leu Arg
            20

<210> SEQ ID NO 128
<211> LENGTH: 24
<212> TYPE: PRT
<213> ORGANISM: Homo sapiens
<220> FEATURE:
<221> NAME/KEY: MOD_RES
```

```
<222> LOCATION: (21)..(21)
<223> OTHER INFORMATION: Phosphorylated-Ser

<400> SEQUENCE: 128

Gln Ile Pro Pro Pro Gln Thr Pro Ser Thr Asp Pro Gln Thr Leu Pro
1               5                   10                  15

Leu Ser Phe Arg Ser Leu Leu Arg
            20

<210> SEQ ID NO 129
<211> LENGTH: 24
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Thr

<400> SEQUENCE: 129

Gln Ile Pro Pro Pro Gln Thr Pro Ser Thr Asp Pro Gln Thr Leu Pro
1               5                   10                  15

Leu Ser Phe Arg Ser Leu Leu Arg
            20

<210> SEQ ID NO 130
<211> LENGTH: 24
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Ser

<400> SEQUENCE: 130

Lys Gln Ser Ala Gly Pro Asn Ser Pro Thr Gly Gly Gly Gly Gly Gly
1               5                   10                  15

Gly Ser Gly Gly Thr Arg Met Arg
            20

<210> SEQ ID NO 131
<211> LENGTH: 10
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 131

Leu Glu Asn Leu His Gly Ala Met Tyr Thr
1               5                   10

<210> SEQ ID NO 132
<211> LENGTH: 27
<212> TYPE: PRT
<213> ORGANISM: Homo sapiens
<220> FEATURE:
<221> NAME/KEY: MOD_RES
<222> LOCATION: (22)..(22)
<223> OTHER INFORMATION: Phosphorylated-Ser

<400> SEQUENCE: 132

Cys Leu Asp Pro His Ser Ser Phe Gln Pro Pro Thr Pro Ser Pro
1               5                   10                  15

Gly Ser Ser Gly Leu Ser Met Asp Leu Val Lys
            20                  25
```

```
<210> SEQ ID NO 133
<211> LENGTH: 27
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: Phosphorylated-Ser

<400> SEQUENCE: 133

Cys Leu Asp Pro His Ser Ser Phe Gln Pro Pro Thr Pro Ser Pro
1               5                   10                  15

Gly Ser Ser Gly Leu Ser Met Asp Leu Val Lys
            20                  25

<210> SEQ ID NO 134
<211> LENGTH: 12
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 134

Phe Thr Glu Tyr Ser Met Thr Ser Ser Val Met Arg
1               5                   10

<210> SEQ ID NO 135
<211> LENGTH: 19
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Ser

<400> SEQUENCE: 135

Thr Gln Ser Thr Phe Glu Gly Phe Pro Gln Ser Pro Leu Gln Ile Pro
1               5                   10                  15

Val Ser Arg

<210> SEQ ID NO 136
<211> LENGTH: 25
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Ser

<400> SEQUENCE: 136

Leu Thr Pro Pro Ser Pro Val Arg Ser Glu Pro Gln Pro Ala Val Pro
1               5                   10                  15

Gln Glu Leu Glu Met Pro Val Leu Lys
            20                  25

<210> SEQ ID NO 137
<211> LENGTH: 18
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 137
```

Asn Lys Gly Val Tyr Ser Ser Thr Asn Glu Leu Thr Thr Asp Ser Thr
1               5                   10                  15

Pro Lys

<210> SEQ ID NO 138
<211> LENGTH: 22
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Thr

<400> SEQUENCE: 138

Asp Asn Leu Gly Glu Val Pro Leu Thr Pro Thr Glu Glu Ala Ser Leu
1               5                   10                  15

Pro Leu Ala Val Thr Lys
            20

<210> SEQ ID NO 139
<211> LENGTH: 27
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Phosphorylated-Ser

<400> SEQUENCE: 139

Met Ala Ile Gln Val Asp Lys Phe Asn Phe Glu Ser Phe Pro Glu Ser
1               5                   10                  15

Pro Gly Glu Lys Gly Gln Phe Ala Asn Pro Lys
            20                  25

<210> SEQ ID NO 140
<211> LENGTH: 20
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Thr

<400> SEQUENCE: 140

Ile Gln Gln Ala Leu Thr Ser Pro Leu Pro Met Thr Pro Ile Leu Glu
1               5                   10                  15

Gly Ser His Arg
            20

<210> SEQ ID NO 141
<211> LENGTH: 19
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Ser

<400> SEQUENCE: 141

Ala Met Val Ser Pro Phe His Ser Pro Pro Ser Thr Pro Ser Ser Pro
1               5                   10                  15

Gly Val Arg

<210> SEQ ID NO 142
<211> LENGTH: 19
<212> TYPE: PRT

```
<213> ORGANISM: Homo sapiens
<220> FEATURE:
<221> NAME/KEY: MOD_RES
<222> LOCATION: (8)..(8)
<223> OTHER INFORMATION: Phosphorylated-Ser

<400> SEQUENCE: 142

Ala Met Val Ser Pro Phe His Ser Pro Pro Ser Thr Pro Ser Ser Pro
1               5                   10                  15

Gly Val Arg

<210> SEQ ID NO 143
<211> LENGTH: 19
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Phosphorylated-Ser

<400> SEQUENCE: 143

Ala Met Val Ser Pro Phe His Ser Pro Pro Ser Thr Pro Ser Ser Pro
1               5                   10                  15

Gly Val Arg

<210> SEQ ID NO 144
<211> LENGTH: 17
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Phosphorylated-Tyr

<400> SEQUENCE: 144

Ala Ser Gly Gln Glu Ser Glu Glu Val Ala Asp Asp Tyr Gln Pro Val
1               5                   10                  15

Arg

<210> SEQ ID NO 145
<211> LENGTH: 23
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 145

Thr Ser Gln Pro Glu Asp Leu Thr Asp Gly Ser Tyr Asp Asp Val Leu
1               5                   10                  15

Asn Ala Glu Gln Leu Gln Lys
            20

<210> SEQ ID NO 146
<211> LENGTH: 14
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Thr

<400> SEQUENCE: 146

Lys Gly Pro Lys Thr Pro Gln Asp Gly Phe Gly Phe Arg Arg
1               5                   10
```

```
<210> SEQ ID NO 147
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 147

Asp Thr Asn Asp Tyr Phe Asn Gln Ala Lys
1               5                   10

<210> SEQ ID NO 148
<211> LENGTH: 12
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 148

Leu Asn Met Gly Glu Ile Glu Thr Leu Asp Asp Tyr
1               5                   10

<210> SEQ ID NO 149
<211> LENGTH: 21
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Ser

<400> SEQUENCE: 149

Glu Val Gln Asp Lys Asp Tyr Pro Leu Thr Pro Pro Ser Pro Thr
1               5                   10                  15

Val Asp Glu Pro Lys
            20

<210> SEQ ID NO 150
<211> LENGTH: 21
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Thr

<400> SEQUENCE: 150

Glu Val Gln Asp Lys Asp Tyr Pro Leu Thr Pro Pro Ser Pro Thr
1               5                   10                  15

Val Asp Glu Pro Lys
            20

<210> SEQ ID NO 151
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Ser

<400> SEQUENCE: 151

Phe Pro Asn Ser Pro Val Lys Ala Glu Lys
1               5                   10
```

```
<210> SEQ ID NO 152
<211> LENGTH: 27
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Thr

<400> SEQUENCE: 152

Leu Glu Asn Thr Thr Pro Thr Gln Pro Leu Thr Pro Leu His Val Val
1               5                   10                  15

Thr Gln Asn Gly Ala Glu Ala Ser Ser Val Lys
            20                  25

<210> SEQ ID NO 153
<211> LENGTH: 28
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: Phosphorylated-Ser

<400> SEQUENCE: 153

Met Gln Asn Gly Phe Gly Ser Pro Glu Pro Ser Leu Pro Gly Thr Pro
1               5                   10                  15

His Ser Pro Ala Pro Pro Ser Gly Gly Thr Trp Lys
            20                  25

<210> SEQ ID NO 154
<211> LENGTH: 24
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: Phosphorylated-Tyr

<400> SEQUENCE: 154

Gln Ala Ser Pro Glu Thr Ser Ala Ser Pro Asp Gly Ser Gln Asn Leu
1               5                   10                  15

Val Tyr Glu Thr Glu Leu Leu Arg
            20

<210> SEQ ID NO 155
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 155

Met Glu Asn Tyr Glu Leu Ile His Ser Ser Arg
1               5                   10
```